United States Patent
Kurn et al.

(10) Patent No.: US 8,034,568 B2
(45) Date of Patent: Oct. 11, 2011

(54) ISOTHERMAL NUCLEIC ACID AMPLIFICATION METHODS AND COMPOSITIONS

(75) Inventors: Nurith Kurn, Palo Alto, CA (US); Shenglong Wang, San Ramon, CA (US)

(73) Assignee: NuGEN Technologies, Inc., San Carlos, CA (US)

( * ) Notice: Subject to any disclaimer, the term of this patent is extended or adjusted under 35 U.S.C. 154(b) by 0 days.

(21) Appl. No.: 12/370,534

(22) Filed: Feb. 12, 2009

(65) Prior Publication Data

US 2009/0203085 A1 Aug. 13, 2009

Related U.S. Application Data

(60) Provisional application No. 61/028,146, filed on Feb. 12, 2008, provisional application No. 61/074,991, filed on Jun. 23, 2008, provisional application No. 61/085,811, filed on Aug. 1, 2008.

(51) Int. Cl.
C12P 19/34 (2006.01)
C12Q 1/68 (2006.01)

(52) U.S. Cl. ........................ 435/6.12; 435/91.2; 435/91.1

(58) Field of Classification Search ............. 435/6, 91.2, 435/91.1, 6.12
See application file for complete search history.

(56) References Cited

U.S. PATENT DOCUMENTS

| | | |
|---|---|---|
| 3,996,345 A | 12/1976 | Ullman et al. |
| 3,999,345 A | 12/1976 | McKelvey |
| 4,174,384 A | 11/1979 | Ullman et al. |
| 4,261,968 A | 4/1981 | Ullman et al. |
| 4,362,867 A | 12/1982 | Paddock |
| 4,458,066 A | 7/1984 | Caruthers et al. |
| 4,582,788 A | 4/1986 | Erlich |
| 4,683,194 A | 7/1987 | Saiki et al. |
| 4,786,600 A | 11/1988 | Kramer et al. |
| 4,876,187 A | 10/1989 | Duck et al. |
| 4,908,385 A | 3/1990 | Bar-Tana et al. |
| 4,996,143 A | 2/1991 | Heller et al. |
| 5,011,769 A | 4/1991 | Duck et al. |
| 5,043,272 A | 8/1991 | Hartley |
| 5,090,591 A | 2/1992 | Long |
| 5,106,727 A | 4/1992 | Hartley et al. |
| 5,130,238 A | 7/1992 | Malek et al. |
| 5,169,766 A | 12/1992 | Schuster et al. |
| 5,175,243 A | 12/1992 | Ash |
| 5,185,243 A | 2/1993 | Ullman et al. |
| 5,194,370 A | 3/1993 | Berninger et al. |
| 5,262,311 A | 11/1993 | Pardee et al. |
| 5,270,184 A | 12/1993 | Walker et al. |
| 5,328,985 A | 7/1994 | Sano et al. |
| 5,340,716 A | 8/1994 | Ullman et al. |
| 5,399,491 A | 3/1995 | Kacian et al. |
| 5,403,711 A | 4/1995 | Walder et al. |
| 5,409,818 A | 4/1995 | Davey et al. |
| 5,427,911 A | 6/1995 | Ruano |
| 5,427,929 A | 6/1995 | Richards et al. |
| 5,427,930 A | 6/1995 | Birkenmeyer et al. |
| 5,437,990 A | 8/1995 | Burg et al. |
| 5,455,166 A | 10/1995 | Walker |
| 5,480,784 A | 1/1996 | Kacian et al. |
| 5,491,063 A | 2/1996 | Fisher et al. |
| 5,508,178 A | 4/1996 | Rose et al. |
| 5,510,270 A | 4/1996 | Fodor et al. |
| 5,545,522 A | 8/1996 | Van Gelder et al. |
| 5,554,516 A | 9/1996 | Kacian et al. |
| 5,554,517 A | 9/1996 | Davey et al. |
| 5,556,752 A | 9/1996 | Lockhart et al. |
| 5,556,771 A | 9/1996 | Shen et al. |
| 5,565,322 A | 10/1996 | Heller |
| 5,578,832 A | 11/1996 | Trulson et al. |
| 5,589,339 A | 12/1996 | Hampson et al. |
| 5,595,891 A | 1/1997 | Rose et al. |
| 5,616,478 A | 4/1997 | Chetverin et al. |
| 5,627,275 A | 5/1997 | Roll |
| 5,641,658 A | 6/1997 | Adams et al. |
| 5,648,211 A | 7/1997 | Fraiser et al. |
| 5,654,142 A | 8/1997 | Kievits et al. |
| 5,660,988 A | 8/1997 | Duck et al. |
| 5,665,539 A | 9/1997 | Sano et al. |
| 5,665,545 A | 9/1997 | Malek et al. |
| 5,665,845 A | 9/1997 | Allman |
| 5,679,512 A | 10/1997 | Laney et al. |
| 5,679,524 A | 10/1997 | Nikiforov et al. |
| 5,683,879 A | 11/1997 | Laney et al. |
| 5,686,272 A | 11/1997 | Marshall et al. |
| 5,688,648 A | 11/1997 | Mathies et al. |
| 5,693,502 A | 12/1997 | Gold et al. |
| 5,700,642 A | 12/1997 | Monforte et al. |
| 5,708,154 A | 1/1998 | Smith et al. |

(Continued)

FOREIGN PATENT DOCUMENTS

EP 0050424 A1 4/1982

(Continued)

OTHER PUBLICATIONS

Bing, et al. Bridge Amplification: A Solid Phase PCR System for the Amplification and Detection of Allelic Differences in Single Copy Genes. Genetic Identity Conference Proceedings. 1996. Available at http://www.promega.com/geneticidproc/ussymp7proc/0726.html. Accessed Dec. 22, 2009.

(Continued)

Primary Examiner — Kenneth R. Horlick
Assistant Examiner — Joyce Tung
(74) Attorney, Agent, or Firm — Wilson Sonsini Goodrich & Rosati

(57) ABSTRACT

Methods and compositions are provided related to the amplification of target polynucleotide sequences as well as total RNA and total DNA amplification. In some embodiments, the methods and compositions also allow for the immobilization and capture of target polynucleotides with defined 3' and or 5' sequences to solid surfaces. The polynucleotides attached to the solid surfaces can be amplified or eluted for downstream processing. In some cases, nucleotides attached to solid surfaces can be used for high throughput sequencing of nucleotide sequences related to target DNA or target RNA.

40 Claims, 22 Drawing Sheets

U.S. PATENT DOCUMENTS

| | | | |
|---|---|---|---|
| 5,709,994 A | 1/1998 | Pease et al. |
| 5,710,028 A | 1/1998 | Eyal et al. |
| 5,712,124 A | 1/1998 | Walker |
| 5,712,127 A | 1/1998 | Malek et al. |
| 5,716,785 A | 2/1998 | Van Gelder et al. |
| 5,731,146 A | 3/1998 | Duck et al. |
| 5,731,171 A | 3/1998 | Bohlander |
| 5,744,308 A | 4/1998 | Guillou-Bonnici et al. |
| 5,744,312 A | 4/1998 | Mamone et al. |
| 5,747,255 A | 5/1998 | Brenner |
| 5,763,178 A | 6/1998 | Chirikjian et al. |
| 5,766,846 A | 6/1998 | Schlossmacher et al. |
| 5,766,849 A | 6/1998 | McDonough et al. |
| 5,773,601 A | 6/1998 | Agrawal |
| 5,811,238 A | 9/1998 | Stemmer et al. |
| 5,824,517 A | 10/1998 | Cleuziat et al. |
| 5,824,518 A | 10/1998 | Kacian et al. |
| 5,829,547 A | 11/1998 | Fujii et al. |
| 5,830,655 A | 11/1998 | Monforte et al. |
| 5,830,721 A | 11/1998 | Stemmer et al. |
| 5,837,832 A | 11/1998 | Chee et al. |
| 5,846,710 A | 12/1998 | Bajaj |
| 5,849,478 A | 12/1998 | Cashman |
| 5,849,542 A | 12/1998 | Reeve et al. |
| 5,849,547 A | 12/1998 | Cleuziat et al. |
| 5,854,033 A | 12/1998 | Lizardi et al. |
| 5,858,665 A | 1/1999 | Hepp et al. |
| 5,871,697 A | 2/1999 | Rothberg et al. |
| 5,876,976 A | 3/1999 | Richards et al. |
| 5,882,867 A | 3/1999 | Ullman et al. |
| 5,888,779 A | 3/1999 | Kacian et al. |
| 5,888,819 A | 3/1999 | Goelet et al. |
| 5,916,777 A | 6/1999 | Kacian et al. |
| 5,925,517 A | 7/1999 | Tyagi et al. |
| 5,932,449 A | 8/1999 | Emanuel et al. |
| 5,932,450 A | 8/1999 | Dattagupta et al. |
| 5,932,451 A | 8/1999 | Wang et al. |
| 5,958,681 A | 9/1999 | Wetmur et al. |
| 5,962,271 A | 10/1999 | Chenchik et al. |
| 5,962,272 A | 10/1999 | Chenchik et al. |
| 5,965,409 A | 10/1999 | Pardee et al. |
| 5,985,548 A | 11/1999 | Collier et al. |
| 6,004,744 A | 12/1999 | Goelet et al. |
| 6,004,745 A | 12/1999 | Arnold, Jr. et al. |
| 6,013,431 A | 1/2000 | Soderlund et al. |
| 6,027,889 A | 2/2000 | Barany et al. |
| 6,027,923 A | 2/2000 | Wallace |
| 6,030,774 A | 2/2000 | Laney et al. |
| 6,037,152 A | 3/2000 | Richards et al. |
| 6,040,138 A | 3/2000 | Lockhart et al. |
| 6,060,288 A | 5/2000 | Adams et al. |
| 6,083,689 A | 7/2000 | Martinelli et al. |
| 6,087,103 A | 7/2000 | Burmer |
| 6,090,591 A | 7/2000 | Burg et al. |
| 6,096,715 A | 8/2000 | Rossi et al. |
| 6,107,032 A | 8/2000 | Kilger et al. |
| 6,107,061 A | 8/2000 | Johnson |
| 6,124,120 A | 9/2000 | Lizardi |
| 6,132,997 A | 10/2000 | Shannon |
| 6,136,533 A | 10/2000 | Bekkaoui et al. |
| 6,140,086 A | 10/2000 | Fox et al. |
| 6,143,495 A | 11/2000 | Lizardi et al. |
| 6,159,685 A | 12/2000 | Pinkel et al. |
| 6,183,960 B1 | 2/2001 | Lizardi |
| 6,210,884 B1 | 4/2001 | Lizardi |
| 6,218,105 B1 | 4/2001 | Hall et al. |
| 6,218,151 B1 | 4/2001 | Cleuziat et al. |
| 6,251,600 B1 | 6/2001 | Winger et al. |
| 6,251,639 B1 | 6/2001 | Kurn |
| 6,255,060 B1 | 7/2001 | Eberwine et al. |
| 6,270,961 B1 | 8/2001 | Drmanac |
| 6,271,002 B1 | 8/2001 | Linsley et al. |
| 6,280,935 B1 | 8/2001 | Macevicz |
| 6,280,949 B1 | 8/2001 | Lizardi |
| 6,291,166 B1 | 9/2001 | Gerdes et al. |
| 6,291,170 B1 | 9/2001 | Van Gelder et al. |
| 6,300,073 B1 | 10/2001 | Zhao et al. |
| 6,306,365 B1 | 10/2001 | Ruoslahti et al. |
| 6,309,842 B1 | 10/2001 | Dower et al. |
| 6,309,843 B1 | 10/2001 | Timms |
| 6,316,229 B1 | 11/2001 | Lizardi et al. |
| 6,319,714 B1 | 11/2001 | Crameri et al. |
| 6,326,142 B1 | 12/2001 | Royer |
| 6,335,160 B1 | 1/2002 | Patten et al. |
| 6,344,356 B1 | 2/2002 | Stemmer |
| 6,358,712 B1 | 3/2002 | Jarrell et al. |
| 6,365,375 B1 | 4/2002 | Dietmaier et al. |
| 6,410,278 B1 | 6/2002 | Notomi et al. |
| 6,485,944 B1 | 11/2002 | Church et al. |
| 6,617,137 B2 | 9/2003 | Dean et al. |
| 6,642,034 B2 * | 11/2003 | Lizardi ............... 435/91.1 |
| 6,673,549 B1 | 1/2004 | Furness et al. |
| 6,686,156 B2 | 2/2004 | Kurn |
| 6,692,918 B2 | 2/2004 | Kurn |
| 6,794,138 B1 | 9/2004 | Cao et al. |
| 6,815,164 B2 | 11/2004 | Kurn |
| 6,858,413 B2 | 2/2005 | Kurn |
| 6,927,024 B2 | 8/2005 | Dodge et al. |
| 6,946,251 B2 | 9/2005 | Kurn |
| 6,949,633 B1 * | 9/2005 | Monforte et al. ............ 536/22.1 |
| 6,951,722 B2 | 10/2005 | Mukai et al. |
| 7,056,671 B2 | 6/2006 | Enoki et al. |
| 7,094,536 B2 | 8/2006 | Kurn |
| 7,176,025 B2 | 2/2007 | Kurn |
| 7,294,461 B2 | 11/2007 | Kurn |
| 7,351,557 B2 | 4/2008 | Kurn |
| 7,354,717 B2 | 4/2008 | Kurn |
| 7,402,386 B2 | 7/2008 | Kurn et al. |
| 7,534,569 B2 | 5/2009 | Chang et al. |
| 7,824,890 B2 | 11/2010 | Hoser et al. |
| 2001/0000077 A1 | 3/2001 | Engelhardt et al. |
| 2001/0034048 A1 | 10/2001 | Kurn |
| 2001/0041334 A1 | 11/2001 | Rashtchian et al. |
| 2002/0028447 A1 | 3/2002 | Li et al. |
| 2002/0058270 A1 | 5/2002 | Kurn |
| 2002/0064837 A1 | 5/2002 | Trinh et al. |
| 2002/0115088 A1 | 8/2002 | Kurn |
| 2002/0127575 A1 | 9/2002 | Hoke et al. |
| 2002/0142309 A1 | 10/2002 | Dattagupta |
| 2002/0164628 A1 | 11/2002 | Kurn |
| 2002/0177141 A1 | 11/2002 | Chee et al. |
| 2003/0017591 A1 | 1/2003 | Kurn |
| 2003/0049657 A1 | 3/2003 | Cherry |
| 2003/0073081 A1 | 4/2003 | Mukai et al. |
| 2003/0087251 A1 | 5/2003 | Kurn |
| 2003/0104460 A1 | 6/2003 | Rabbani et al. |
| 2003/0186234 A1 | 10/2003 | Kurn |
| 2003/0204331 A1 | 10/2003 | Whitney et al. |
| 2003/0215926 A1 | 11/2003 | Kurn et al. |
| 2004/0005614 A1 | 1/2004 | Kurn et al. |
| 2004/0023271 A1 | 2/2004 | Kurn et al. |
| 2004/0033499 A1 | 2/2004 | Ilsley |
| 2004/0096853 A1 | 5/2004 | Mayer |
| 2004/0203019 A1 | 10/2004 | Kurn et al. |
| 2004/0203025 A1 | 10/2004 | Kurn |
| 2005/0003441 A1 | 1/2005 | Kurn |
| 2005/0014192 A1 | 1/2005 | Kurn |
| 2005/0019793 A1 | 1/2005 | Kurn et al. |
| 2005/0064456 A1 | 3/2005 | Kurn |
| 2005/0079510 A1 | 4/2005 | Berka et al. |
| 2005/0123950 A1 | 6/2005 | Mukai et al. |
| 2005/0130173 A1 | 6/2005 | Leamon et al. |
| 2005/0208538 A1 | 9/2005 | Kurn et al. |
| 2006/0008824 A1 | 1/2006 | Ronaghi et al. |
| 2006/0014182 A1 | 1/2006 | Kurn |
| 2006/0246434 A1 * | 11/2006 | Erlander et al. ............... 435/6 |
| 2006/0269934 A1 | 11/2006 | Woudenberg et al. |
| 2007/0054301 A1 | 3/2007 | Becker et al. |
| 2008/0176311 A1 | 7/2008 | Kurn |
| 2008/0182300 A1 | 7/2008 | Kurn |
| 2009/0036663 A1 | 2/2009 | Kurn |
| 2009/0068709 A1 | 3/2009 | Kurn et al. |
| 2009/0130721 A1 | 5/2009 | Kurn et al. |
| 2009/0203085 A1 * | 8/2009 | Kurn et al. ............... 435/91.2 |
| 2009/0203531 A1 | 8/2009 | Kurn et al. |
| 2009/0233804 A1 | 9/2009 | Kurn et al. |
| 2009/0239232 A1 | 9/2009 | Kurn et al. |

| | | | |
|---|---|---|---|
| 2009/0275486 A1 | 11/2009 | Kurn et al. | |
| 2010/0022403 A1 | 1/2010 | Kurn et al. | |
| 2010/0311066 A1 | 12/2010 | Kurn | |

FOREIGN PATENT DOCUMENTS

| | | | |
|---|---|---|---|
| EP | 0084796 B1 | 8/1983 | |
| EP | 0201184 B1 | 11/1986 | |
| EP | 0237362 B1 | 9/1987 | |
| EP | 0258017 B1 | 3/1988 | |
| EP | 0320308 B1 | 6/1989 | |
| EP | 0365627 B1 | 5/1990 | |
| EP | 0395398 A2 | 10/1990 | |
| EP | 0395398 A3 | 10/1990 | |
| EP | 0497272 B1 | 8/1992 | |
| EP | 0500224 A2 | 8/1992 | |
| EP | 0505012 B1 | 9/1992 | |
| EP | 0543612 B1 | 5/1993 | |
| EP | 0329822 B1 | 6/1994 | |
| EP | 0667393 A2 | 8/1995 | |
| EP | 0667393 A3 | 8/1995 | |
| EP | 0497271 B1 | 10/1996 | |
| EP | 0878553 B1 | 11/1998 | |
| EP | 0971039 A2 | 1/2000 | |
| EP | 0971039 A3 | 1/2000 | |
| EP | 1055736 A1 | 11/2000 | |
| EP | 1167524 A1 | 1/2002 | |
| EP | 1273737 A2 | 1/2003 | |
| EP | 1275737 A2 | 1/2003 | |
| EP | 1281757 A1 | 2/2003 | |
| EP | 1312682 A1 | 5/2003 | |
| JP | 6327500 A | 11/1994 | |
| JP | 7023799 A | 1/1995 | |
| WO | WO 88/02746 A1 | 4/1988 | |
| WO | WO 88/10315 A1 | 12/1988 | |
| WO | WO 89/01050 A1 | 2/1989 | |
| WO | WO 90/01069 A1 | 2/1990 | |
| WO | WO 92/15712 A1 | 9/1992 | |
| WO | WO 92/18521 A1 | 10/1992 | |
| WO | WO 93/15229 A2 | 8/1993 | |
| WO | WO 95/03426 A2 | 2/1995 | |
| WO | WO 93/15229 A3 | 3/1995 | |
| WO | WO 95/21271 A1 | 8/1995 | |
| WO | WO 97/03207 A1 | 1/1997 | |
| WO | WO 97/04123 A1 | 2/1997 | |
| WO | WO 97/04126 A1 | 2/1997 | |
| WO | WO 97/32040 A2 | 9/1997 | |
| WO | WO 97/32040 A3 | 10/1997 | |
| WO | WO 98/01050 A1 | 1/1998 | |
| WO | WO 98/06736 A1 | 2/1998 | |
| WO | WO 98/28443 A1 | 7/1998 | |
| WO | WO 98/44151 A1 | 10/1998 | |
| WO | WO 98/59066 A1 | 12/1998 | |
| WO | WO 99/18241 A1 | 4/1999 | |
| WO | WO 99/23256 A1 | 5/1999 | |
| WO | WO 99/25873 A1 | 5/1999 | |
| WO | WO 99/29901 A1 | 6/1999 | |
| WO | WO 99/37808 A1 | 7/1999 | |
| WO | WO 99/40219 A1 | 8/1999 | |
| WO | WO 99/42618 A1 | 8/1999 | |
| WO | WO 99/55912 A1 | 11/1999 | |
| WO | WO 00/08208 A2 | 2/2000 | |
| WO | WO 00/09745 A1 | 2/2000 | |
| WO | WO 00/08208 A3 | 5/2000 | |
| WO | WO 00/28082 A1 | 5/2000 | |
| WO | WO 00/40715 A2 | 7/2000 | |
| WO | WO 00/52191 A1 | 9/2000 | |
| WO | WO 00/56877 A1 | 9/2000 | |
| WO | WO 00/56925 A2 | 9/2000 | |
| WO | WO 00/56925 A3 | 9/2000 | |
| WO | WO 00/70095 A2 | 11/2000 | |
| WO | WO 01/20035 A2 | 3/2001 | |
| WO | WO 01/20035 A3 | 3/2001 | |
| WO | WO 01/23613 A1 | 4/2001 | |
| WO | WO 00/70095 A3 | 8/2001 | |
| WO | WO 01/64952 A2 | 9/2001 | |
| WO | WO 01/73134 A2 | 10/2001 | |
| WO | WO 02/00938 A2 | 1/2002 | |
| WO | WO 02/06533 A2 | 1/2002 | |
| WO | WO 02/28876 A2 | 4/2002 | |
| WO | WO 02/29117 A2 | 4/2002 | |
| WO | WO 02/48402 A2 | 6/2002 | |
| WO | WO 02/057487 A2 | 7/2002 | |
| WO | WO 02/057487 A3 | 7/2002 | |
| WO | WO 02/28876 A3 | 8/2002 | |
| WO | WO 02/072772 A2 | 9/2002 | |
| WO | WO 02/072773 A2 | 9/2002 | |
| WO | WO 01/64952 A3 | 12/2002 | |
| WO | WO 02/103013 A2 | 12/2002 | |
| WO | WO 01/73134 A3 | 1/2003 | |
| WO | WO 03/012100 A2 | 2/2003 | |
| WO | WO 03/012100 A3 | 2/2003 | |
| WO | WO 03/012142 A1 | 2/2003 | |
| WO | WO 02/103013 A3 | 3/2003 | |
| WO | WO 02/06533 A3 | 4/2003 | |
| WO | WO 02/000938 A3 | 8/2003 | |
| WO | WO 02/29117 A3 | 8/2003 | |
| WO | WO 02/072772 A3 | 9/2003 | |
| WO | WO 03/078645 A2 | 9/2003 | |
| WO | WO 03/078645 A3 | 9/2003 | |
| WO | WO 03/083435 A2 | 10/2003 | |
| WO | WO 03/083435 A3 | 10/2003 | |
| WO | WO 2004/011665 A2 | 2/2004 | |
| WO | WO 02/48402 A3 | 4/2004 | |
| WO | WO 2004/069849 A2 | 8/2004 | |
| WO | WO 2004/092418 A2 | 10/2004 | |
| WO | WO 2004/092418 A3 | 12/2004 | |
| WO | WO 2004/069849 A3 | 3/2005 | |
| WO | WO 2004/011665 A3 | 7/2005 | |
| WO | WO 2005/065321 A2 | 7/2005 | |
| WO | WO 2006/138257 A2 | 12/2006 | |
| WO | WO 2007/030759 A2 | 3/2007 | |
| WO | WO 2004/069849 A3 | 4/2007 | |
| WO | WO 2007/041201 A2 | 4/2007 | |
| WO | WO 2007/030759 A3 | 6/2007 | |
| WO | WO 2007/041201 A3 | 11/2007 | |
| WO | WO 2007/136717 A1 | 11/2007 | |
| WO | WO 2008/005459 A2 | 1/2008 | |
| WO | WO 2008/005459 A3 | 2/2008 | |
| WO | WO 2006/138257 A3 | 12/2008 | |

OTHER PUBLICATIONS

Hatch, et al. Rolling circle amplification of DNA immobilized on solid surfaces and its application to multiplex detection. Genet Anal. Apr. 1999;15(2):35-40.

International search report dated Nov. 20, 2009 for PCT Application No. US2009/33936.

Westin, et al. Anchored multiplex amplification on a microelectronic chip array. Nat Biotechnol. Feb. 2000;18(2):199-204.

U.S. Appl. No. 60/255,638, filed Dec. 13, 2000, Kurn.

U.S. Appl. No. 60/381,457, filed May 17, 2002, Kurn.

U.S. Appl. No. 60/533,381, filed Dec. 29, 2003, Kurn et al.

Abravaya et al. Detection of point mutations with a modified ligase chain reaction (Gap-LCR). Nucleic Acids Research. 1995;23(4):675-682.

Adessi et al. Solid phase DNA amplification: characterisation of primer attachment and amplification mechanisms. Nucleic Acids Research. 2000;28(20):E87.

Agrawal et al. Site Specific Functionalization of Oligonucleotides for Attaching Two Different Reporter Groups. Nucleic Acids Research. 1990;18(18):5419-5423.

Akhras et al. Connector inversion probe technology: a powerful one-primer multiplex DNA amplification system for numerous scientific applications. PLoS ONE. 2007;2(9):e915.

Arashi-Heese et al. XcmI site-containing vector for direct cloning and in vitro transcription of PCR product. Molecular Biotechnology. 1999;12(3):281-3.

Ausubel et al. (eds.) Current Protocols in Molecular Biology. John Wiley & Sons, Inc.; 1995:iii-xii (Table of Contents Only.).

Baner et al. Parallel gene analysis with allele-Specific padlock probes and tag microarrays. Nucleic Acids Research. 2003;31(17):e103.

Barbas III et al. In Vitro Evolution of a Neutralizing Human Antibody to Human Immunodeficiency Virus Type I to Enhance Affinity and Broaden Strain Cross-Reactivity. Proc. Natl. Acad. Sci. USA. 1994;91:3809-3813.

Barker et al. Increased DNA microarray hybridization specificity using sscDNA targets. BMC Genomics. 2005;6(1):57.
Barth et al. Combining Phage Display and Screening of cDNA Expression Libraries: A New Approach for Identifying the Target Antigen of an scFv Preselected by Phage Display. Journal of Molecular Biology. 2000;301:751-757.
Beaucage et al. Deoxynucleoside Phosphoramidites—A New Class of Key Intermediates for Deoxypolynucleotide Synthesis. Tetrahedron Letters. 1981;22(20):1859-1862.
Beggs, et al. Characterization of *Mycobacterium tuberculosis* complex direct repeat sequence for use in cycling probe reaction. J Clin Microbiol. Dec. 1996;34(12):2985-9.
Bekkaoui et al. Rapid detection of the mecA gene in methicillin resistant staphylococci using a colorimetric cycling probe technology. Diagnostic Microbiology and Infectious Disease. 1999;34(2):83-90.
Ben-Artzi, et al. Double-stranded RNA-dependent RNase activity associated with human immunodeficiency virus type 1 reverse transcriptase. Proc Natl Acad Sci U S A. Feb. 1, 1992;89(3):927-31.
Blanchard et al. High-density oligonucleotide arrays. Biosensors & Bioelectronics. 1996;11(6/7):687-690.
Brenner et al. Gene expression analysis by massively parallel signature sequencing (MPSS) on microbead arrays. Nature Biotechnology. 2000;18(6):630-634.
Brown et al. Chemical Synthesis and Cloning of a Tyrosine tRNA Gene. Methods In Enzymology. 1979;68:109-151.
Brown, T.A. Ed. Molecular Biology, LabFax. Bios Scientific Publishers. Academic Press. 1991; pp. 147-148.
Caruthers et al. Chemical synthesis of deoxyoligonucleotides by the phosphoramidite method. Methods in Enzymology. 1987;154:287-313.
Chetverin et al. On the nature of spontaneous RNA synthesis by Q beta replicase. Journal of Molecular Biology. 1991;222(1):3-9.
Church. Genomes for All. Scientific American. 2006;294(1):46-54.
Coco et al. DNA Shuffling Method for Generating Highly Recombined Genes and Evolved Enzymes. Nature Biotechnology. 2001;19:354-359.
Cohen et al. Construction of biologically functional bacterial plasmids in vitro. Proc. Natl. Acad. Sci. USA. 1973;70(11):3240-4.
Coljee et al. Seamless Gene Engineering Using RNA- and DNA-Overhang Cloning. Nature Biotechnology. 2000;18:789-791.
Crameri et al. Molecular Evolution of an Arsenate Detoxification Pathway by DNA Shuffling. Nature Biotechnology. 1997;15:436-438.
Dafforn et al. Linear mRNA amplification from as little as 5 ng total RNA for global gene expression analysis. Biotechniques. 2004;37(5):854-857.
Dahl et al. Multigene amplification and massively parallel sequencing for cancer mutation discovery. Proc. Natl. Acad. Sci. USA. 2007;104(22):9387-9392.
Daigo et al. Degenerate Oligonucleotide Primed-Polymerase Chain Reaction-Based Array Comparative Genomic Hybridization for Extensive Amplicon Profiling of Breast Cancers. American Journal of Pathology. 2001;158(5):1623-1631.
Database WPI, Section Ch, Week 199507, Derwent Publications Ltd., London, GB; AN 1995-047919, XP002276586 & JP 06 327500 A (Toyobo KK), Nov. 29, 1994. (Abstract Only). 1 page total.
Dean et al. Comprehensive Human Genome Amplification Using Multiple Displacement Amplification. Proc. Natl. Acad. USA. 202;(8):5261-5266.
Derisi et al. Use of cDNA microarray to analyse gene expression patterns in human cancer. Nature Genetics. 1996;14:457-460.
Dietmaier et al. Multiple Mutation Analyses in Single Tumor Cells with Improved Whole Genome Amplification. American Journal of Pathology. 1999;154(1):83-95.
Dressman et al. Transforming single DNA molecules into fluorescent magnetic particles for detection and enumeration of genetic variations. Proc. Natl. Acad. Sci. USA. 2003;100(15):8817-8822.
European Search Report (Supplementary partial) mailed Dec. 22, 2005 for European Patent Application No. 02731119.0.
European search report dated Mar. 13, 2006 for Application No. 02731119.
European search report dated Sep. 17, 2009 for Application No. 04002084.4.
European search report dated Nov. 13, 2006 for Application No. 03717952.
European Search Report mailed on May 13, 2004 for patent application No. 02721342.0-2402.
Fan et al. Highly parallel genomic assays. Nature Reviews Genetics. 2006;7(8):632-644.
Flanagan et al. A Cytosine Analog That Confers Enhanced Potency to Antisense Oligonucleotides. Proc. Natl. Acad. Sci. USA. 1999;96(7):3513-3518.
Fodor et al. Light-Directed, spatially addressable parallel chemical synthesis. Science. 1991;251:767-773.
Freier et al. Improved Free-Energy Parameters for Predictions of RNA Duplex Stability. Proc. Natl. Acad. Sci. USA. 1986;83:9373-9377.
Freshney. ed. Animal Cell Culture. IRL Press: Oxford; 1987: vii-xii (Table of Contents Only.).
Fu et al. Sequencing Double-Stranded DNA by Strand Displacement. Nucleic Acids Research. 1997;25(3):677-679.
Gait. Oligonucleotide Synthesis: A Practical Approach. ed. IRL Press: Oxford; 1984:vii-xii (Table of Contents).
Gasparini et al. Scanning the First Part of the Neurofibromatosis Type 1 Gene by RNA-SSCP: Identification of Three Novel Mutations and of Two New Polymorphisms. Human Genetics. 1996;97:492-495.
Ghadessy et al. Directed evolution of polymerase function by compartmentalized self-replication. Proc. Natl. Acad. Sci. USA. 2001;98(8):4552-4557.
Go. Protein Structures and Split Genes. Advances in Biophysics. 1985;19:91-131.
Goodchild. Conjugates of Oligonucleotides and Modified Oligonucleotides: A Review of Their Synthesis and Properties. Bioconjugate Chemistry. 1990;1(3):165-187.
Guatelli et al. Isothermal, In Vitro Amplification of Nucleic Acids by a Multienzyme Reaction Modeled After Retroviral Replication. Proc. Natl. Acad. Sci. USA. 1990;87:1874-1878.
Gubler et al. A simple and very efficient method for generating cDNA libraries. Gene. 1983;25:263-269.
Gulick et al. Forced Evolution of Glutathione S-Transferase to Create a More Efficient Drug Detoxication Enzyme. Proc. Natl. Acad. Sci. USA. 1995;92:8140-8144.
Habermann et al. Clostridial Neurotoxins: Handling and Action at the Cellular and Molecular Level. Current Topics in Microbiology and Immunology. 1986;129:93-179.
Heim et al. Engineering Green Fluorescent Protein for Imporved Brightness, Longer Wavelengths and Fluorescence Resonance Energy Transfer. Current Biology. 1996;6:178-182.
Hendrickson et al. High sensitivity multianalyte immunoassay using covalent DNA-labeled antibodies and polymerase chain reaction. Nucleic Acids Research. 1995;23: 522-529.
Hottiger, et al. Strand displacement activity of the human immunodeficiency virus type 1 reverse transcriptase heterodimer and its individual subunits. J Biol Chem. Jan. 14, 1994;269(2):986-91.
Huber, et al. Processing of the primer for plus strand DNA synthesis by human immunodeficiency virus 1 reverse transcriptase. J Biol Chem. Jun. 25, 1990;265(18):10565-73.
Hutchison et al. Cell-free cloning using phi29 DNA polymerase. Proc. Natl. Acad. Sci. USA. 2005;102(48):17332-17336.
Innis et al. PCR Protocols: A Guide to Methods and Applications. Eds. Academic Press. 1990:v-x (Table of Contents).
International search report dated Feb. 3, 2003 for PCT Application No. US2001/047775.
International search report dated Mar. 9, 2007 for PCT Application No. US2006/035154.
International search report dated Mar. 18, 2003 for PCT Application No. US01/20660.
International search report dated Jun. 23, 2003 for PCT Application No. US02/07306.
International search report dated Jul. 3, 2001 for PCT Application No. US00/25104.
International search report dated Sep. 28, 2009 for PCT Application No. US2009/033964.

International search report dated Oct. 20, 2009 for PCT Application No. US2009/037870.
International Search Report mailed Aug. 8, 2003 for PCT Application No. PCT/US02/07377.
International Search Report mailed on Jan. 8, 2004, for PCT patent application No. PCT/US03/07425 filed on Mar. 11, 2003.
International Search Report mailed on Oct. 15, 2004 for PCT Application No. PCT/US2004/012779 filed on Apr. 14, 2004.
International Search Report mailed on Oct. 30, 2003, for PCT patent application No. PCT/US03/10148 filed on Mar. 31, 2003.
Joyce. Directed Molecular Evolution. Scientific American. 1992;267(6):90-97.
Kass et al. Inter-alu polymerase chain reaction: advancements and applications. Analytical Biochemistry. 1955;228(2):185-193.
Khrapko et al. A method for DNA sequencing by hybridization with oligonucleotide matrix. DNA Sequence. 1991;1:375-388.
Kikuchi et al. An Effective Family Shuffling Method Using Single-Stranded DNA. Gene. 2000;243:133-137.
Kikuchi et al. Novel Family Shuffling Methods for the in vitro Evolution of Enzymes. Gene. 1999;236:159-167.
Kojima et al. PCR amplification from single DNA molecules on magnetic beads in emulsion: application for high-throughput screening of transcription factor targets. Nucleic Acids Research. 2005;33(17):e150.
Kolkman et al. Directed Evolution of Proteins by Exon Shuffling. Nature Biotechnology. 2001;19:423-428.
Kricka. Nonisotopic DNA Probe Techniques. Academic Press. 1992. (Table of Contents only).
Kumar et al. The First Analogues of LNA (Locked Nucleic Acids): Phosphorothioate LNA and 2'-Thio-LNA. Bioorganic & Medicinal Chemistry Letters. 1998;8:2219-2222.
Kurn et al. Novel isothermal, linear nucleic acid amplification systems for highly multiplexed applications. Clinical Chemistry. 2005;51(10):1973-1981.
Kurtzman et al. Advances in Directed Protein Evolution by Recursive Genetic Recombination: Applications to Therapeutic Proteins. Current Opinion in Biotechnology. 2001;12:361-370.
Kwoh et al. Transcription-Based Amplification System and Detection of Amplified Human Immunodeficiency Virus Type 1 with a Bead-Based Sandwich Hybridization Format. Proc. Natl. Acad. Sci. USA. 1989;86:1173-1177.
Li et al. Amplification and analysis of DNA sequences in single human sperm and diploid cells. Nature. 1988;335(6189):414-417.
Lishanski et al. Branch Migration Inhibition in PCR-Amplified DNA: Homogeneous Mutation Detection. Nucleic Acids Research. 2000;28(9):E42, pp. i-vii.
Lizardi et al. Mutation detection and single-molecule counting using isothermal rolling-circle amplification. Nature Genetics. 1998;19(3):225-232.
Lockhart et al. Expression monitoring by hybridization to high-density oligonucleotide arrays. Nature Biotechnology. 1996;14:1675-1680.
MacMillan et al. Synthesis of Functionally Tethered Oligodeoxynucleotides by the Convertible Nucleoside Approach. The Journal of Organic Chemistry. 1990;55:5931-5933.
Makos et al. Oligonucleotide Hybridisations on Glass Supports: A Novel Linker for Oligonucleotide Synthesis and Hybridisation Properties of Oligonucleotides Synthesised in situ. Nucleic Acids Research. 1992;20(7):1679-1684.
Marcy et al. Nanoliter reactors improve multiple displacement amplification of genomes from single cells. PLoS Genetics. 2007;3(9):1702-1708.
Marshall et al. DNA chips: an array of possibilities. Nature Biotechnology. 1998;16:27-31.
Maskos et al. Oligonucleotide hybridisations on glass supports: a novel linker for oligonucleotide synthesis and hybridisation properties of oligonucleotides synthesised in situ. Nucleic Acids Research. 1992;20(7):1679-1684.
Matson et al. Biopolymer synthesis on polypropylene supports: Oligonucleotide arrays. Analytical Biochemistry. 1995;224(1):110-116.

Medical Dictionary, online, definition of RNase I, pp. 1-3, retrieved 2009, from: http://www.mondofacto.com/facts/dictionary?Escherichia+coli+RNase+I.
Mitra et al. In situ localized amplification and contact replication of many individual DNA molecules. Nucleic Acids Research. 1999;27(24):e34.
Mullis et al. PCR: Polvmerase Chain Reaction. eds. Birkhauser: Boston; 1994:xv-xvii (Table of Contents).
Mullis et al. Specific Enzymatic Amplification of DNA In Vitro: the Polymerase Chain Reaction. Cold Spring Harbor Symposia on Quantitative Biology. 1986;51:263-273.
Mullis et al. Specific synthesis of DNA in vitro via a polymerase-catalyzed chain reaction. Methods in Enzymology. 1987;155:335-350.
Nakano et al. Single-molecule PCR using water-in-oil emulsion. Journal of Biotechnology. 2003;102(2):117-24.
Narang et al. Improved Phosphotriester Method for the Synthesis of Gene Fragments. Methods of Enzymology. 1979;68:90-99.
New England Biolab Polymerases. Polymerases from NEB. 2008;p. 1-2. Available at http://www.neb.com/nebecomm/tech_reference/polymerases/polymerases_from_neb.asp. Accessed Jun. 30, 2008.
Nugen, Inc. Ovation Biotin RNA Amplification and Labeling System User Guide. Catalog #2300-12. Published 2004.
Nugen, Inc. Technical Report #1. The Ovation Biotin System Validation for Use with Affymetrix GeneChip Arrays. Published 2004.
Okayama et al. High Efficiency Cloning of Full-Length cDNA. Molecular and Cell Biology. 1982;2:161-170.
Orita et al. Detection of Polymorphisms of Human DNA by Gel Electrophoresis as Single-Strand Conformation Polymorphisms. Proc. Natl. Acad. Sci. USA. 1989;86(8):2766-2770.
Orita et al. Rapid and sensitive detection of point mutations and DNA polymorphisms using the polymerase chain reaction. Genomics. 1989;5(4):874-879.
Patel et al. Formation of chimeric DNA primer extension products by template switching onto an annealed downstream oligonucleotide. Proc. Natl. Acad. Sci. USA. 1996;93:2969-2974.
Pease et al. Light-generated oligonucleotide arrays for rapid DNA sequence analysis. Proc. Natl. Acad. Sci. USA Biochemistry. 1994;91:5022-5026.
Pieles et al. Preparation of a Novel Psoralen Containing Deoxyadenosine Building Block for the Facile Solid Phase Synthesis of Psoralen-Modified Oligonucleotides for a Sequence Specific Crosslink to a Given Target Sequence. Nucleic Acids Research. 1989;17(22):8967-8978.
Pluckthun et al. In Vitro Selection and Evolution of Proteins. Advances in Protein Chemistry. 2001;55:367-403.
Ramsay. DNA chips: State-of-the art. Nature Biotechnology. 1998;16:40-44.
Roget et al. Synthesis and Use of Labelled Nucleoside Phosphoramidite Building Blocks Bearing a Reporter Group: Biotinyl, Dinitrophenyl, Pyrenyl and Dansyl. Nucleic Acids Research. 1989;17:7643-7651.
Saiki et al. Primer-directed enzymatic amplification of DNA with a thermostable DNA polymerase. Science. 1988;239:487-491.
Sambrook et al. (eds.), Molecular Cloning—A Laboratory Manual, 1989, Second Edition, Cold Spring Harbor Laboratory Press, Cold Spring Harbor, New York, pp. xi-xxxviii (Table of Contents Only.).
Sano et al. Immuno-PCR: very sensitive antigen detection by means of specific antibody-DNA conjugates. Science. 1992;258:120-122.
Sarkar et al. Screening for Mutations by RNA Single-Strand Conformation Polymorphism (rSScP): Comparison with DNA-SSCP. Nucleic Acids Research. 1992;20(4):871-878.
Sasaki et al. Transcriptional sequencing: A method for DNA sequencing using RNA polymerase. Biochemistry. 1998;95:3455-3460.
Scaringe et al. Novel RNA synthesis method using 5'-0-silyl-2'-0-orthoester protecting groups. Journal of American Chemical Society. 1998;120:11820-11821.
Scaringe. Advanced 5'-SilyI-2'-Orthoester Approach to RNA Oligonucleotide Synthesis. Methods Enzymology. 2000;317:3-18.
Schena et al. Parallel Human Genome Analysis: Microarray-Based Expression Monitoring of 1000 Genes. Proc. Natl. Acad. Sci. USA. 1996;93:10614-10619.

Schena et al. Quantitative monitoring of gene expression patterns with a complementary DNA microarray. Science. 1995;270:467-470.

Schmidt-Dannert. Directed Evolution of Single Proteins, Metabolic Pathways, and Viruses. Biochemistry. 2001;40(44):13125-13136.

Schweitzer et al. Immunoassays with rolling circle DNA amplification: a versatile platform for ultrasensitive antigen dectection. Proc. Natl. Acad. Sci. USA. 2000;97(18):.10113-10119.

Scott et al. Production of Cyclic Peptides and Proteins in vivo. Proc. Natl. Acad. Sci. USA. 1999;96(24):13638-13643.

Shalon et al. A DNA microarray system for analyzing complex DNA samples using two-color fluorescent probe hybridization. Genome Research. 1996;6:639-645.

Shendure et al. Accurate multiplex polony sequencing of an evolved bacterial genome. Science. 2005;309(5741):1728-32.

Stemmer. DNA Shuffling by Random Fragmentation and Reassembly: In Vitro Recombination for Molecular Evolution. Proc. Natl. Acad. Sci. USA. 1994;91:10747-10751.

Stemmer. Rapid Evolution of a Protein In Vitro by DNA Shuffling. Nature. 1994;370:389-391.

Stoecklein et al. SCOMP is Superior to Degenerated Oligonucleotide Primed Polymerase Chain Reaction for Global Amplification of Minute Amounts of DNA From Microdissected Archival Tissue Samples. American Journal of Pathology. 2002;161(1):43-51.

Stump et al. The Use of Modified Primers to Eliminate Cycle Sequencing Artifacts. Nucleic Acids Research. 1999;27(23):4642-4648.

Suzuki, et al. Detection of ras Gene Mutations in Human Lung Cancers by Single Strand Conformation Polymorphism Analysis of Polymerase Chain Reaction Products. Oncogene. 1990;5(7):1037-1043.

Tesler et al. Synthesis and Characterization of DNA Oligomers and Duplexes Containing Covalently attached Molecular Labels: Comparison of Biotin, Fluorescein, and Pyrene Labels by Thermodynamic and Optical Spectroscopic Measurements. Journal of the American Chemical Society. 1989;111:6966-6976.

Tijessen. Hybridization with Nucleic Acid Probes. Elsevier Science Publishers. 1993. (Table of Contents).

Tinoco et al. Improved Estimation of Secondary Structure in Ribonucleic Acids. Nature New Biology. 1973;246:40-41.

Traut. Are Proteins Made of Modules? Molecular and Cellular Biochemistry. 1986;70:3-10.

Vogelstein et al. Digital PCR. Proc. Natl. Acad. Sci. USA. 1999;96(16):9236-41.

Volkov et al. Recombination and Chimeragenesis by in vitro Heteroduplex Formation and in vivo Repair. Nucleic Acids Research. 1999;27(18):e18i-e18vi.

Wadenback et al. Comparison of standard exponential and linear techniques to amplify small cDNA samples for microarrays. BMC Genomics. 2005;6(1):61.

Wahlestedt et al. Potent and nontoxic antisense oligonucleotides containing locked nucleic acids. Proc. Natl. Acad. Sci. USA. 2000;97(10):5633-5638.

Walker et al. Isothermal In Vitro Amplification of DNA by a Restriction Enzyme/DNA Polymerase System. Proc. Natl. Acad. Sci. USA. Applied Biological Sciences. 1992;89:392-396.

Walker et al. Strand displacement amplification—an isothermal, in vitro DNA amplification technique. Nucleic Acids Research 1992;20(7):1691-1696.

Wang et al. Whole genome amplification and high-throughput allelotyping identified five distinct deletion regions on chromosomes 5 and 6 in microdissected early-stage ovarian tumors. Cancer Research. 2001;61:4169-4174.

Wang et al. High-fidelity mRNA amplification for gene profiling. Nature Biotechnology. 2000;18: 457-459.

Wiltshire et al. Detection of Multiple Allergen-Specific IgEs on Microarrays by Immunoassay with Rolling Circle Amplification. Clinical Chemistry. 2000;46(12):1990-1993.

Wu et al. Detection of *Clostridium botulinum* neurotoxin type a using immuno-PCR. Letters in Applied Microbiology. 2001;32:321-325.

Wu et al. The Ligation Amplification Reaction (LAR)-Amplification of Specific DNA Sequences Using Sequential Rounds of Template-Dependent Ligation. Genomics. 1989;4:560-569.

You et al. Directed Evolution of Subtilisin E in *Bacillus subtilis* to Enhance Total Activity in Aqueous Dimethylformamide. Protein Engineering. 1994;9(1):77-83.

Zhang et al. Directed Evolution of a Fucosidase From a Galactosidase by DNA Shuffling and Screening. Proc. Natl. Acad. Sci. USA. 1997;94:4504-4509.

Zhang et al. Protein quantification from complex protein mixtures using a proteomics methodology with single-cell resolution. Proc. Natl. Acad. Sci. USA. 2001;98(10):5497-5502.

Zheng et al. Whole Genome Amplification Increases the Efficiency and Validity of Buccal Cell Genotyping in Pediatric Populations. Cancer Epidemiology. 2001;10:697-700.

European search report dated Nov. 11, 2008 for Application No. 3718172.4.

Inoue, et al. Synthesis and hybridization studies on two complementary nona(2'-O-methyl)ribonucleotides. Nucleic Acids Res. Aug. 11, 1987;15(15):6131-48.

Miyachi, et al. Application of chimeric RNA-DNA oligonucleotides to the detection of pathogenic microorganisms using surface plasmon resonance. Analytica Chimica Acta. 2000; 407(1):1-10.

Stratagene Catalog. 1988; p39. Gene Characterization Kits. Table of Contents.

Wang, et al. Relative stabilities of triple helices composed of combinations of DNA, RNA and 2'-O-methyl-RNA backbones: chimeric circular oligonucleotides as probes. Nucleic Acids Res. Apr. 11, 1995;23(7):1157-64.

* cited by examiner

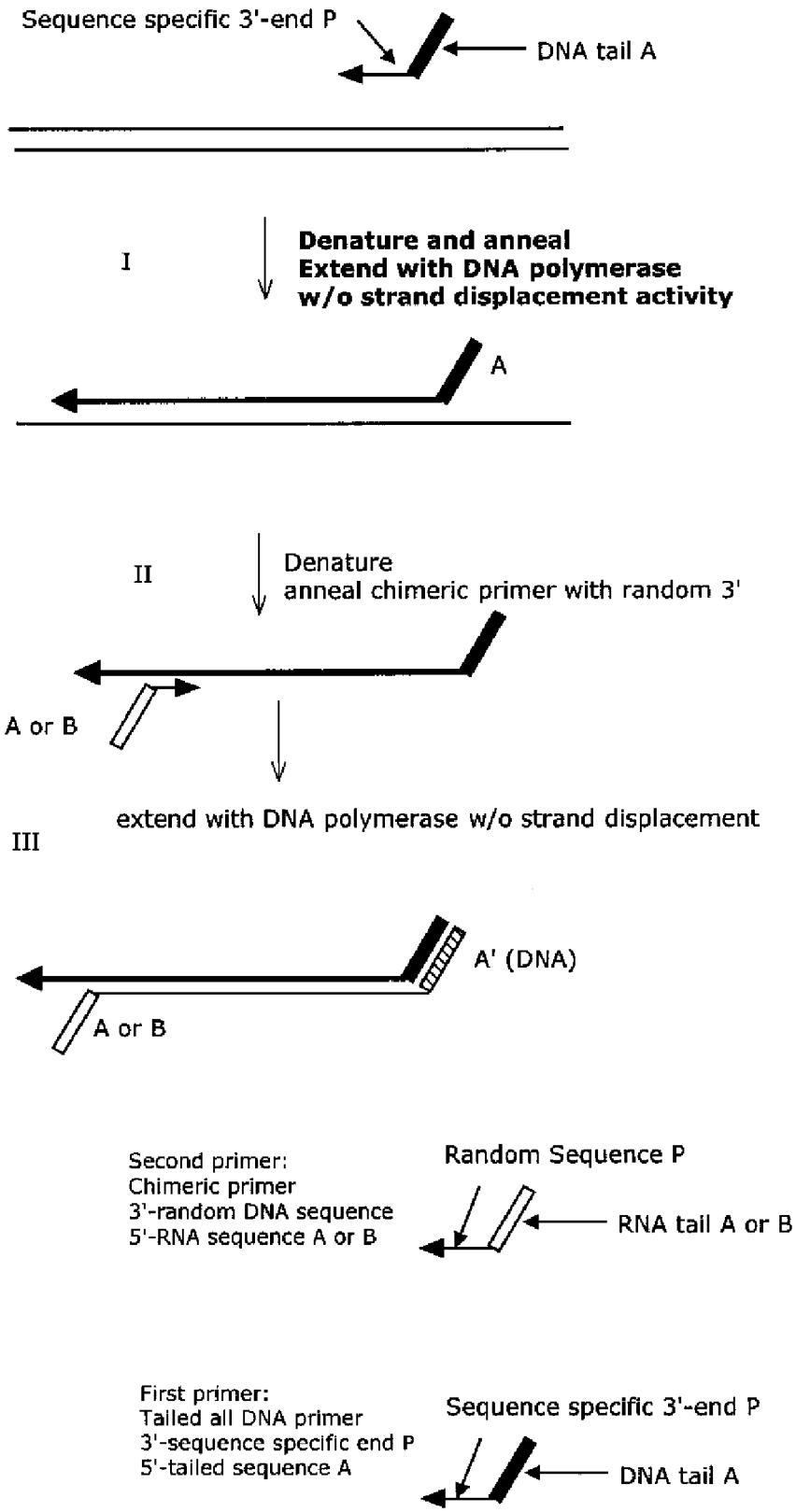
Figure 1: Sequence specific amplification with multiplex capabilities
Tailed first and second primers with same or different sequence tail (A) or (B)

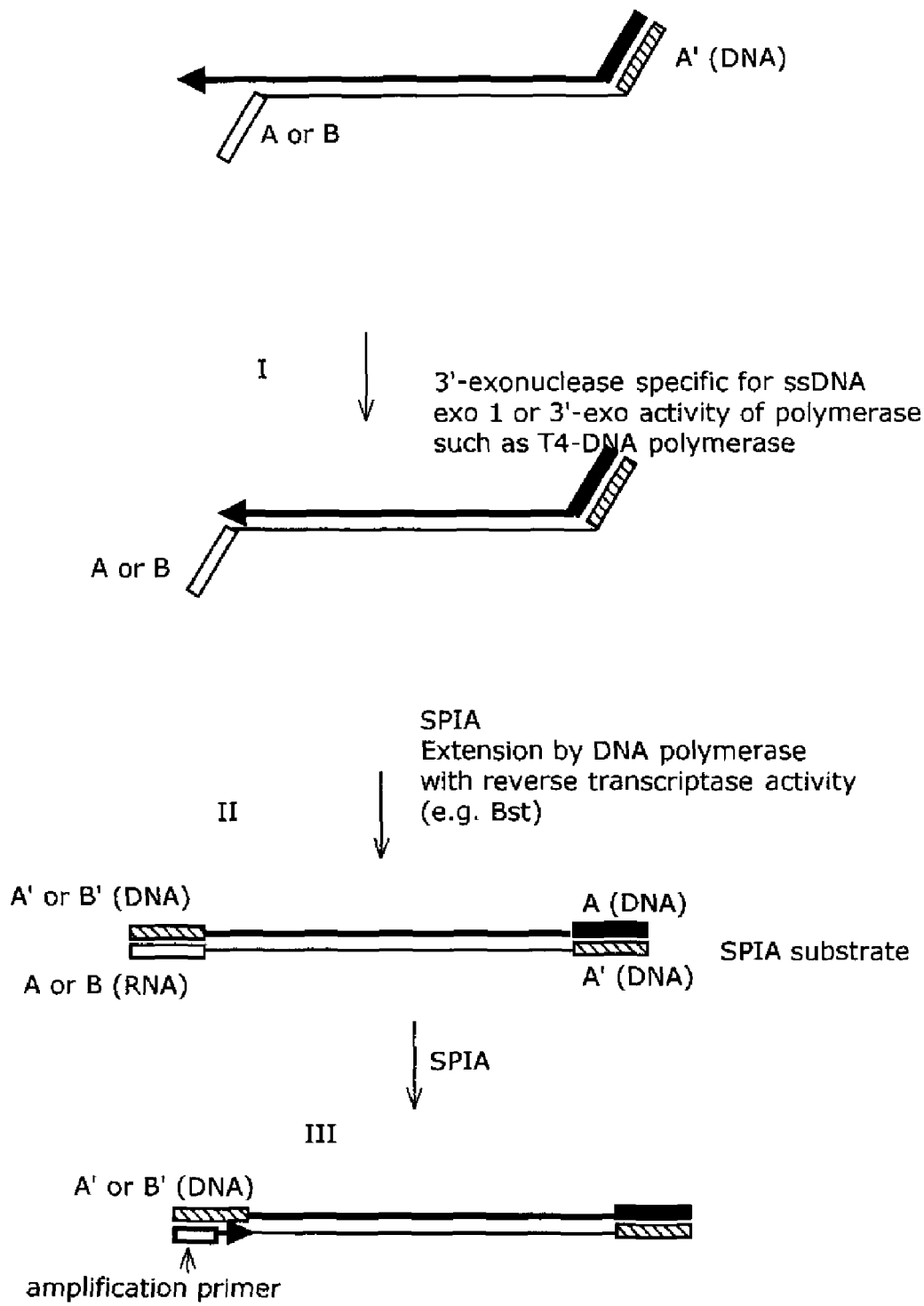
Figure 2: Formation of double stranded nucleic acid suitable for amplification by SPIA from primer extension products (described in Figure 1)

Figure 3: formation of stem-loop suitable for amplification by SPIA method from first and second primer extension products as described in Figure 1
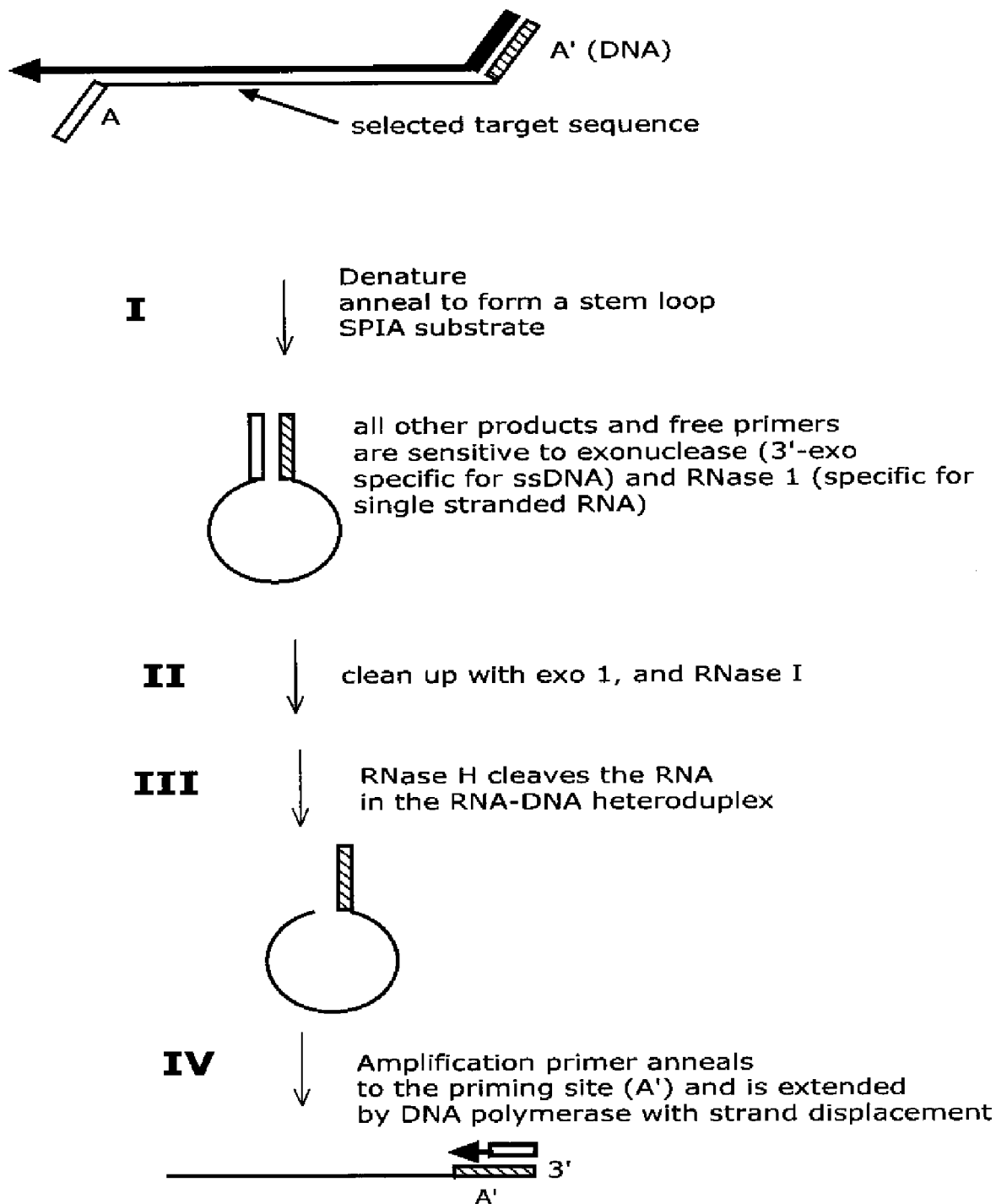

Figure 4
Capture of targeted sequence on immobilized primers
for amplification of specific captured sequences I Hybridize target to immobilized tailed all DNA primer
3'-Target Specific
Priming/annealing sequence (P)
5'-Tail Sequence (A);

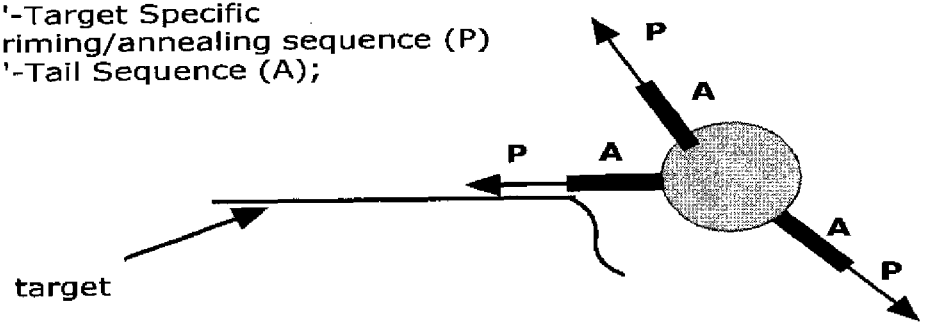

target

II Primer extension with
DNA polymerase

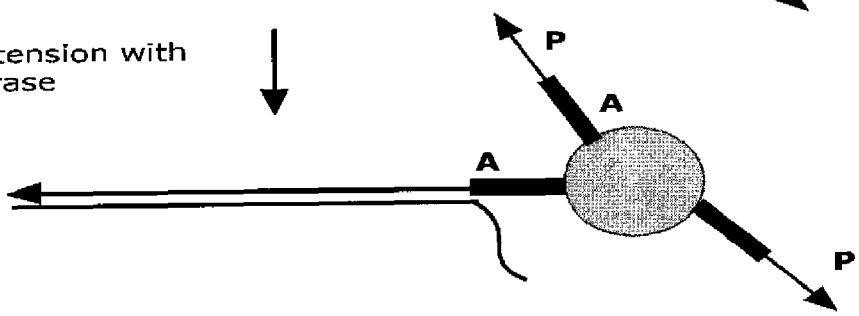

III Denature
Hybridize chimeric primer
to primer extension product

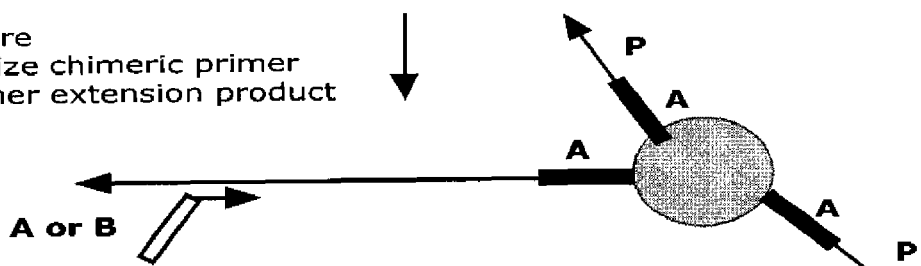

A or B

IV Primer extension
with DNA polymerase

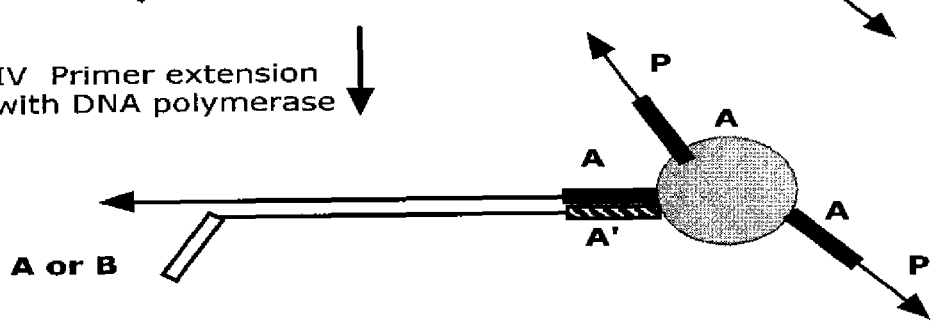

A or B

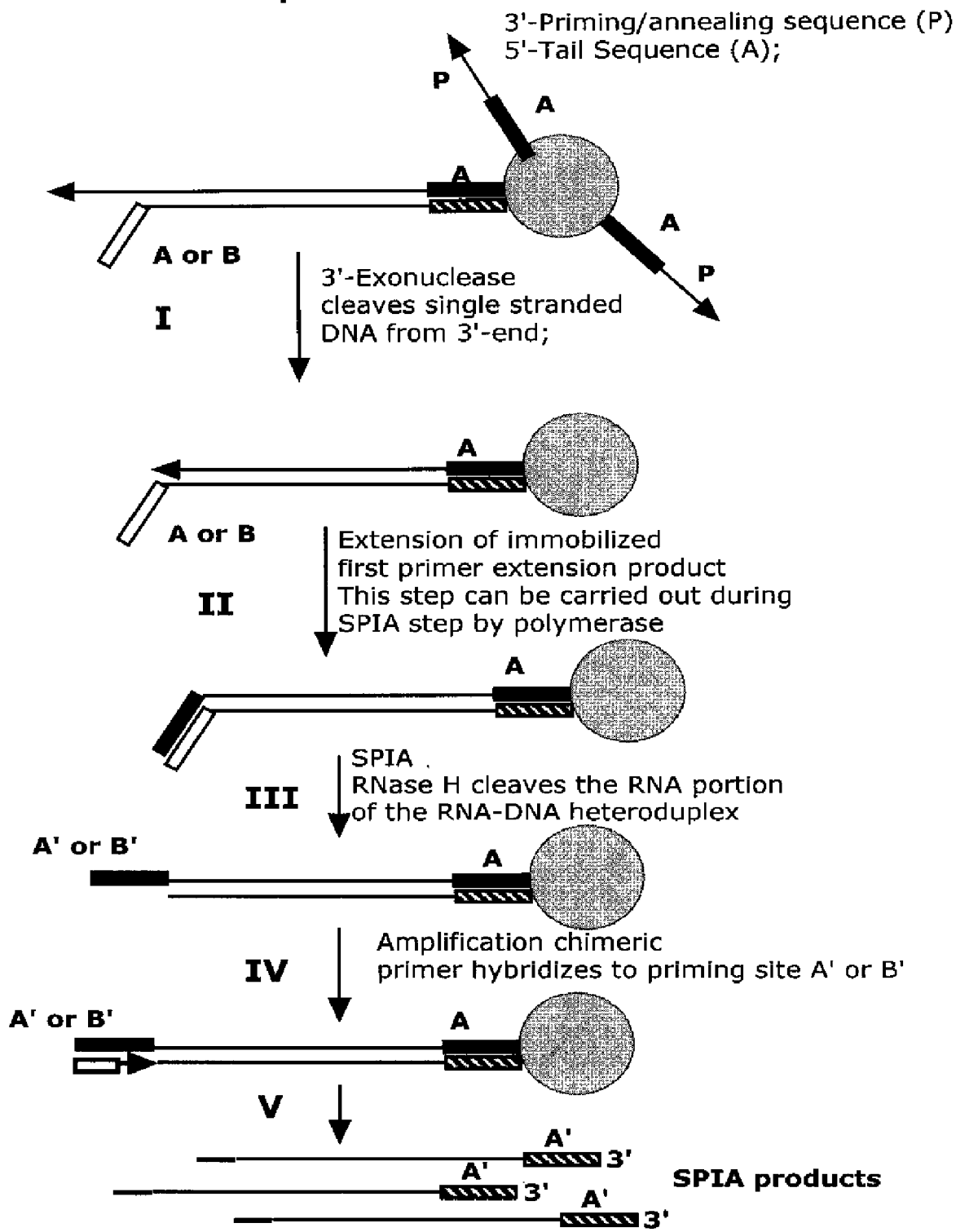
Figure 5 Generation of amplified DNA from captured target sequences, as described in Figure 4, and further SPIA amplification

Figure 6: Generation of amplified DNA in solution from captured target sequences, as described in Figure 4 and further solution phase SPIA amplification
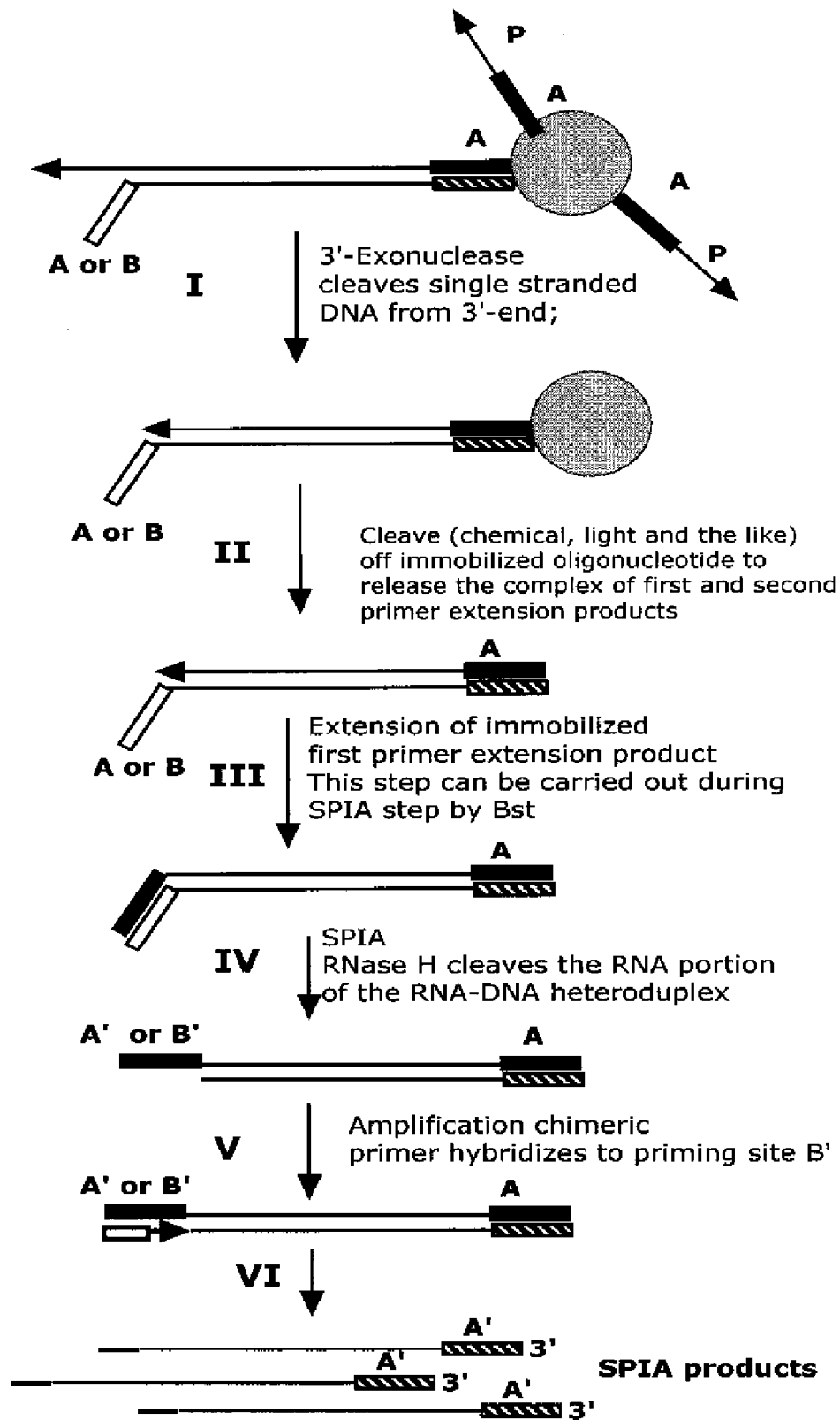

Figure 7
Capture of targeted sequence on immobilized primers
for amplification of specific captured sequences similar
to Figure 4 using chimeric primer with 5'-RNA sequence A,
the same as DNA sequence A of the immobilized oligonucleotides I  Hybridize target to immobilized tailed all DNA primer

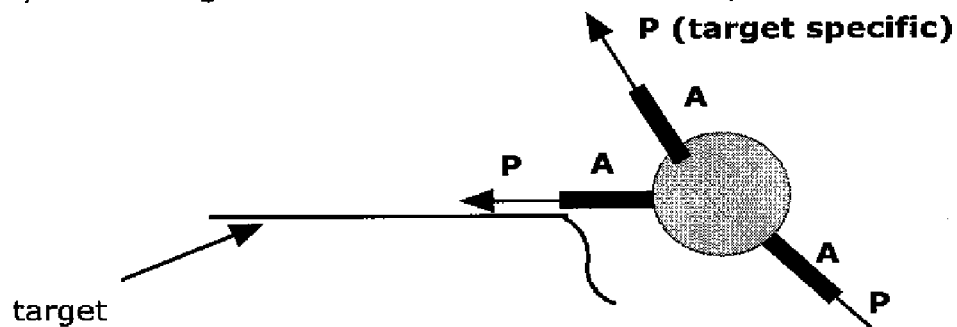

II  Primer extension with
DNA polymerase

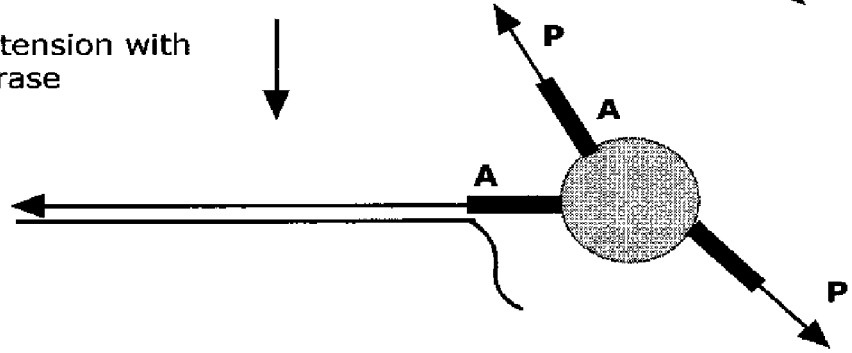

III  Denature
Hybridize chimeric primer
to primer extension product

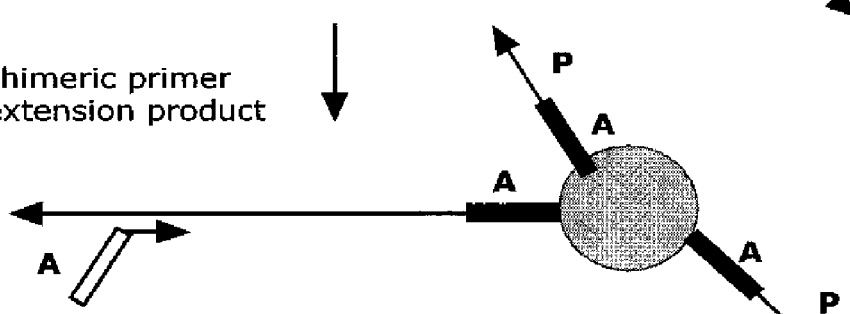

IV  Primer extension
with DNA polymerase

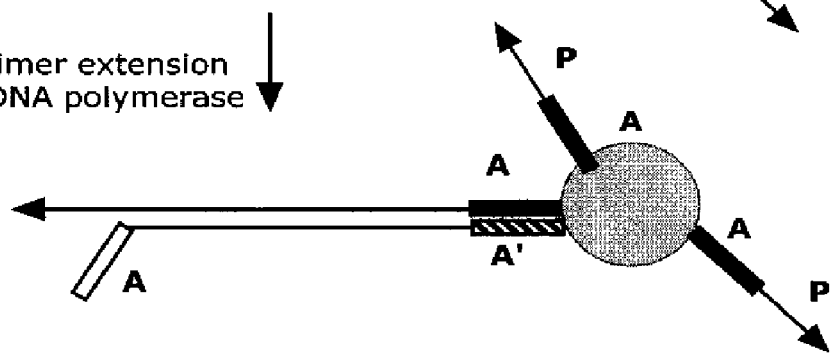

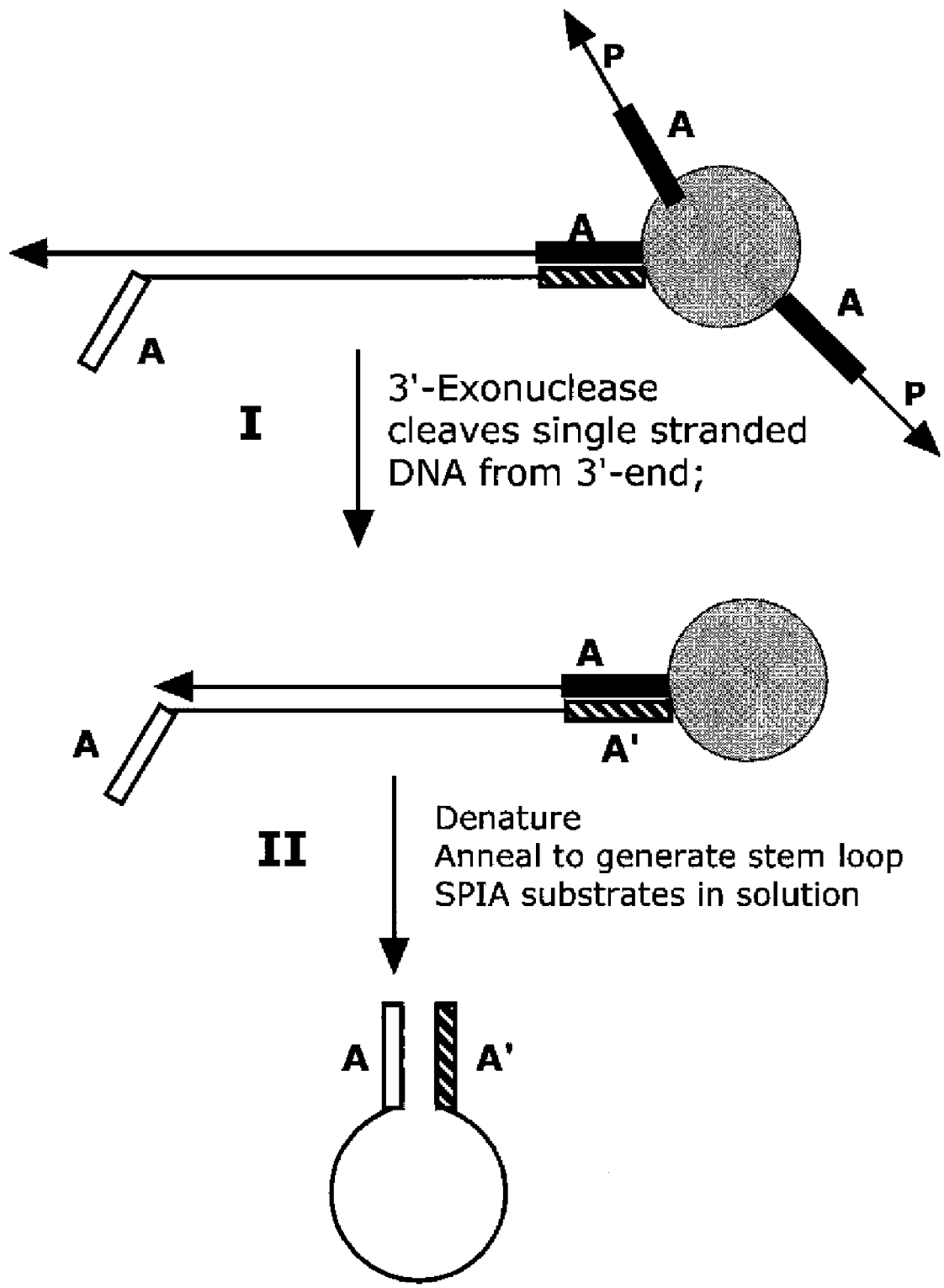
Figure 8: Generation of stem-loop amplification substrate from captured target sequences as described in Figure 7

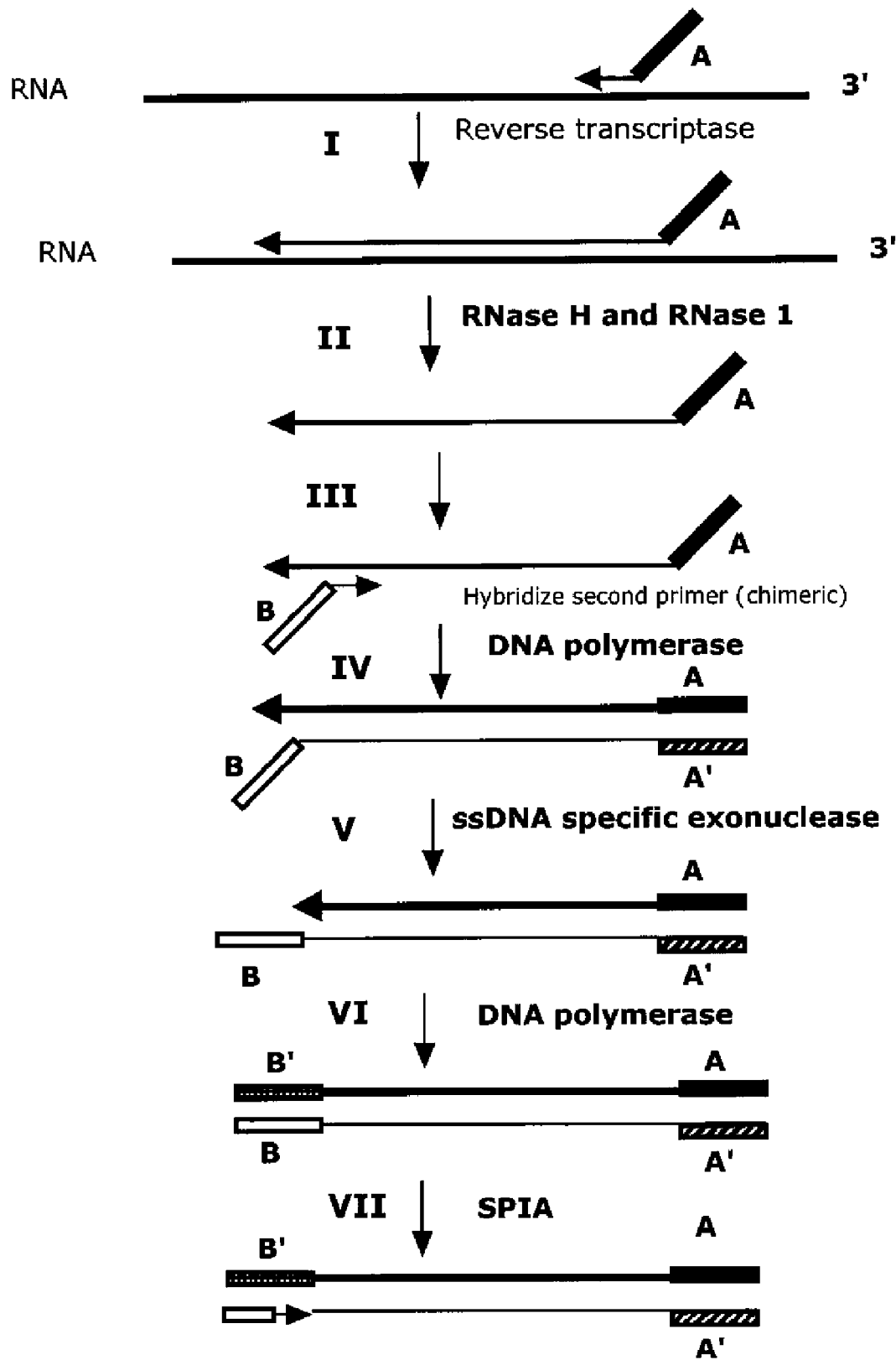

Figure 10: Expansion (from Figure 9) to generate DNA substrate suitable for generation of amplification products by SPIA comprising sequence A and B at the 3' and 5' ends.
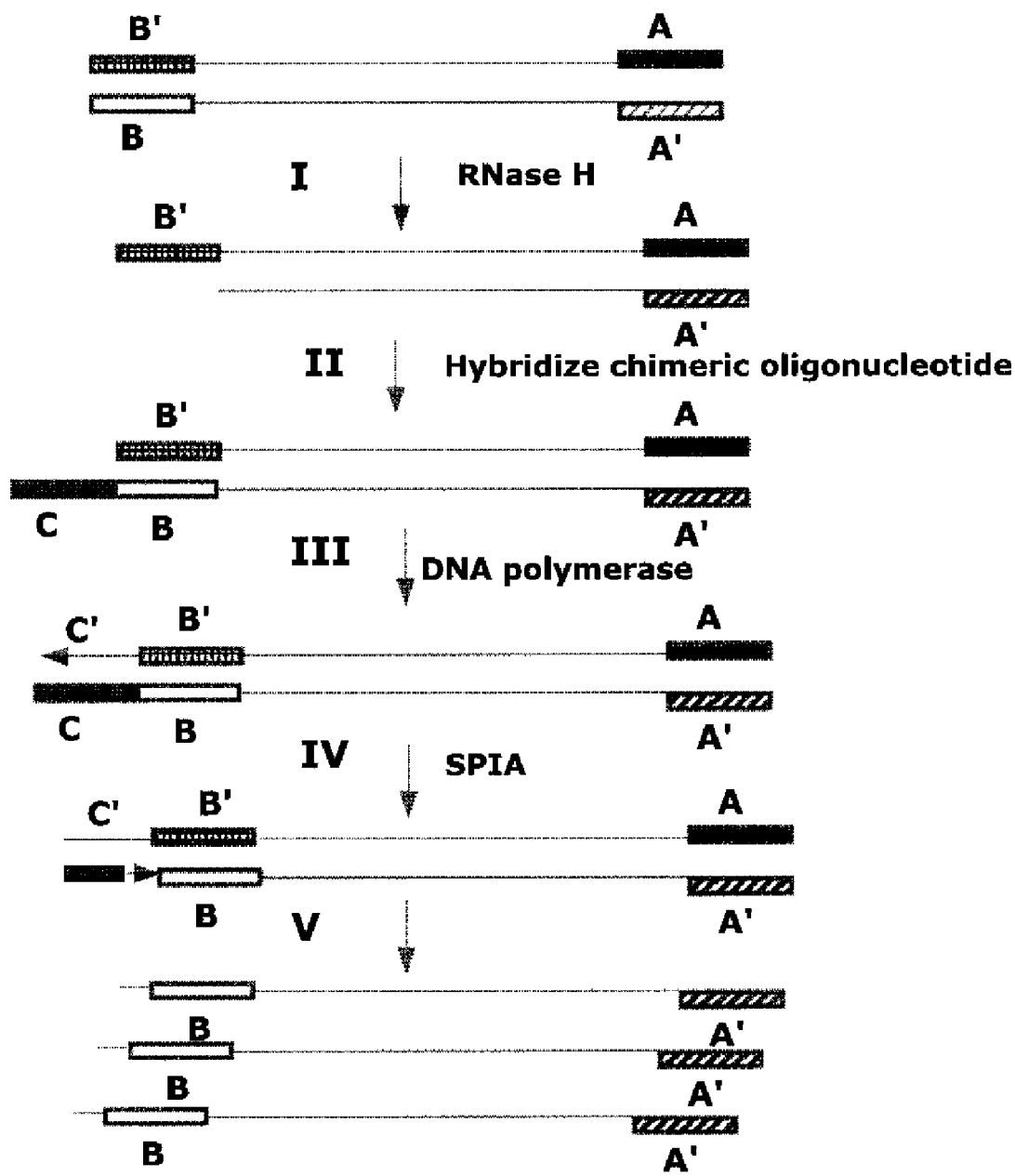

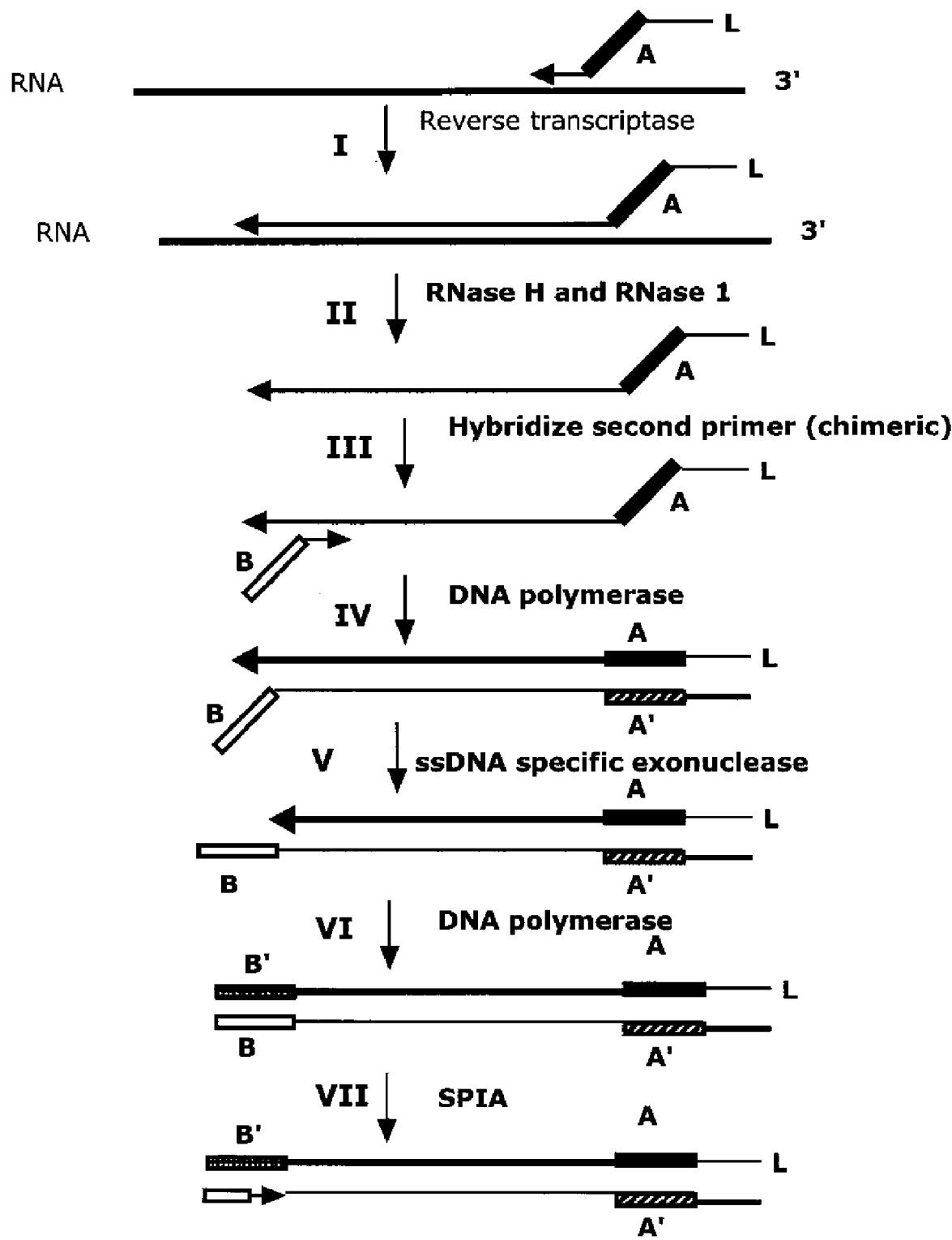
Figure 11 Method for generating a SPIA substrate with a ligand

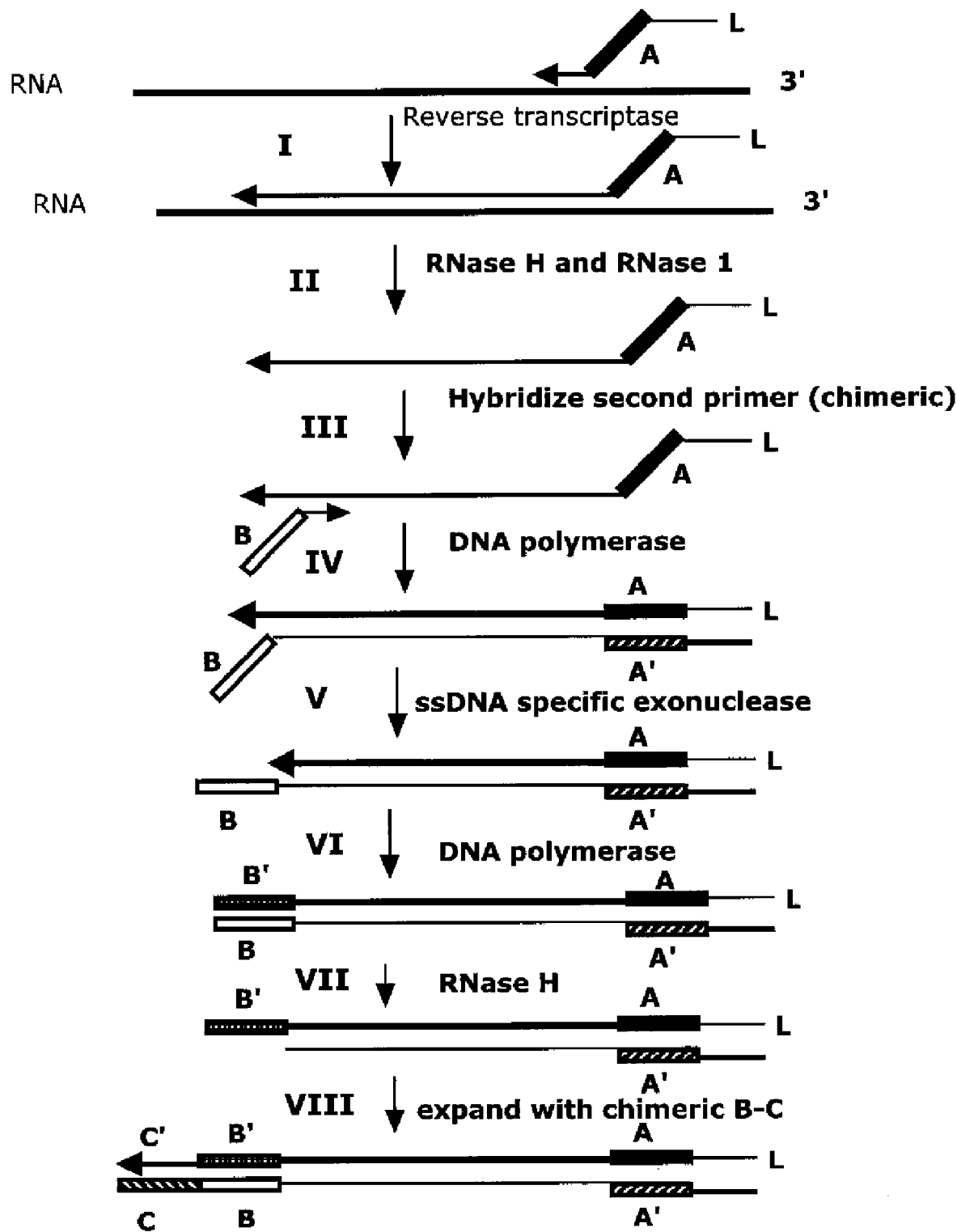
Figure 12 Method of producing a SPIA substrate with a ligand and two defined ends

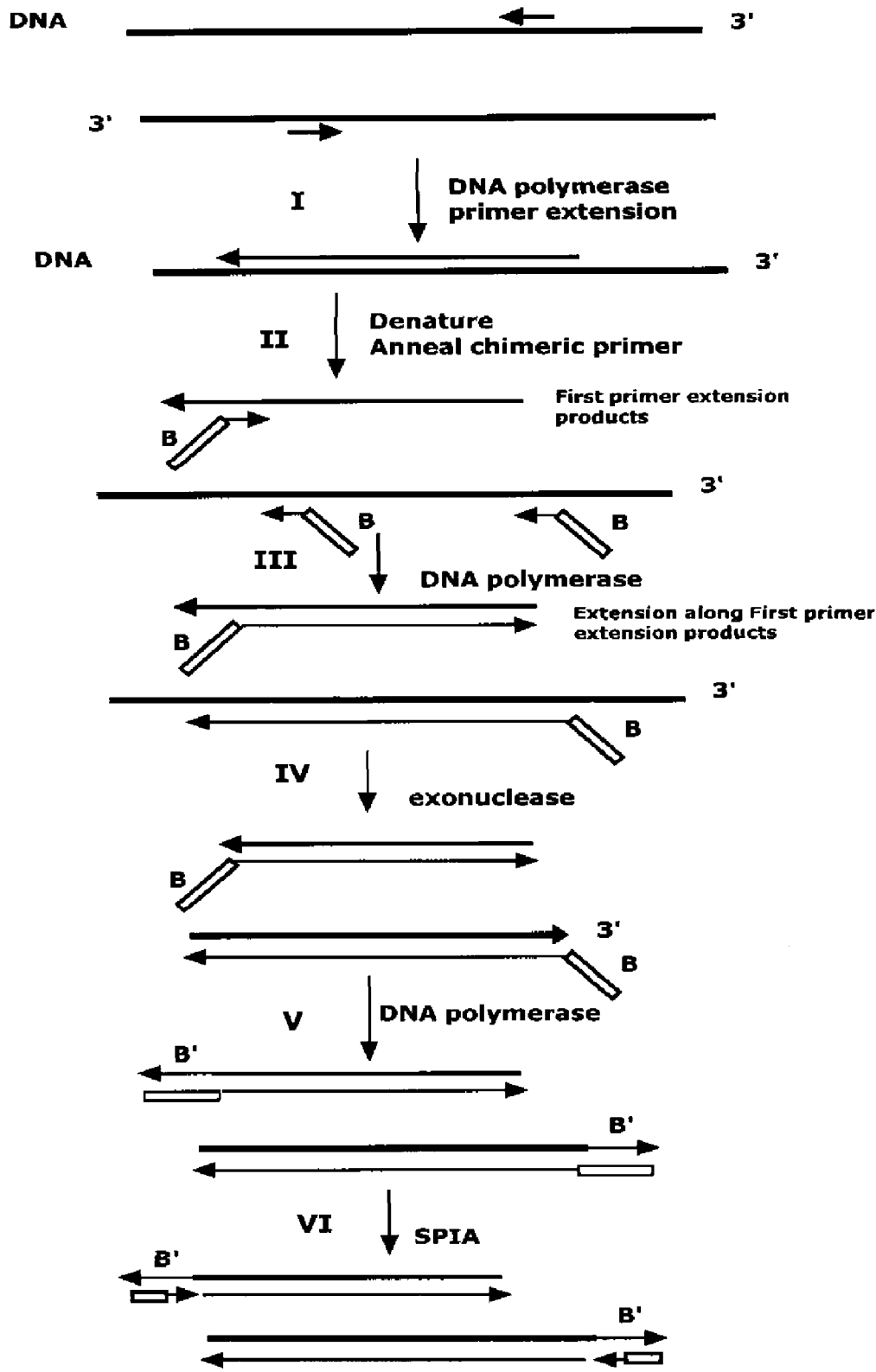
Figure 13: DNA target; non tailed DNA first primer; tailed chimeric second primer

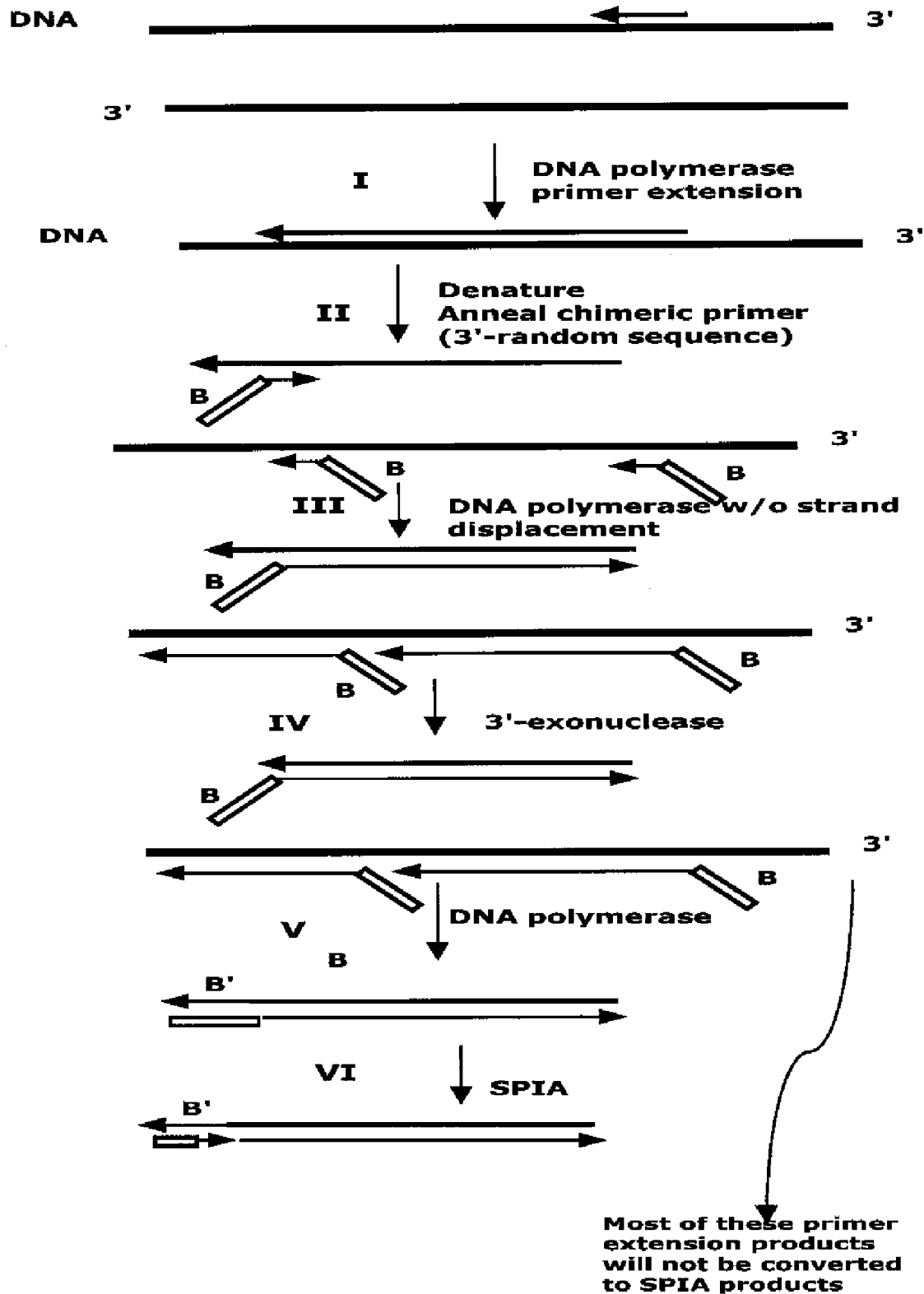
Figure 14: DNA target; non tailed, sequence specific DNA first primer; tailed chimeric second primer

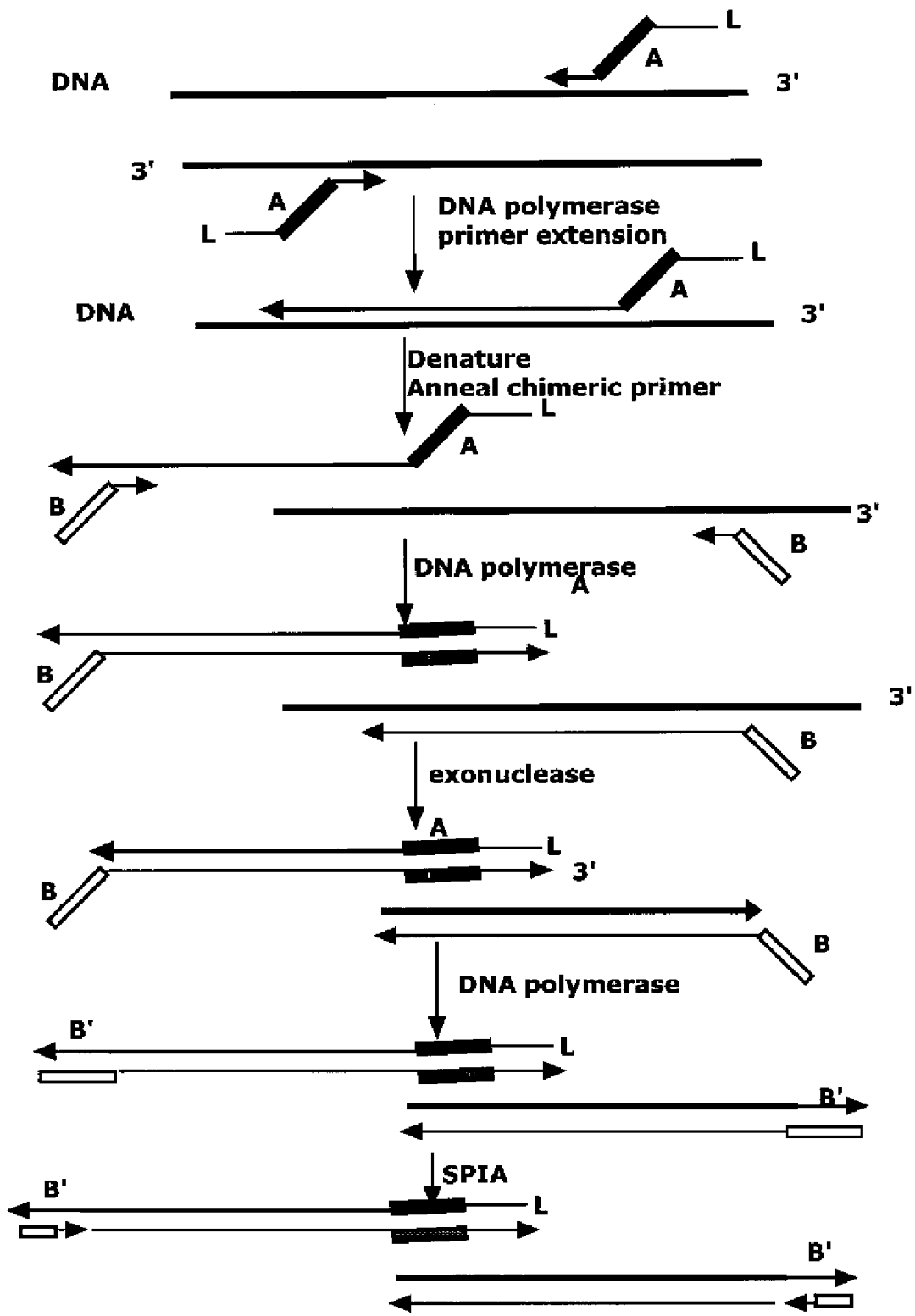
Figure 15 Amplification of a DNA target with a tailed DNA first primer with a ligand L and a chimeric tailed second primer

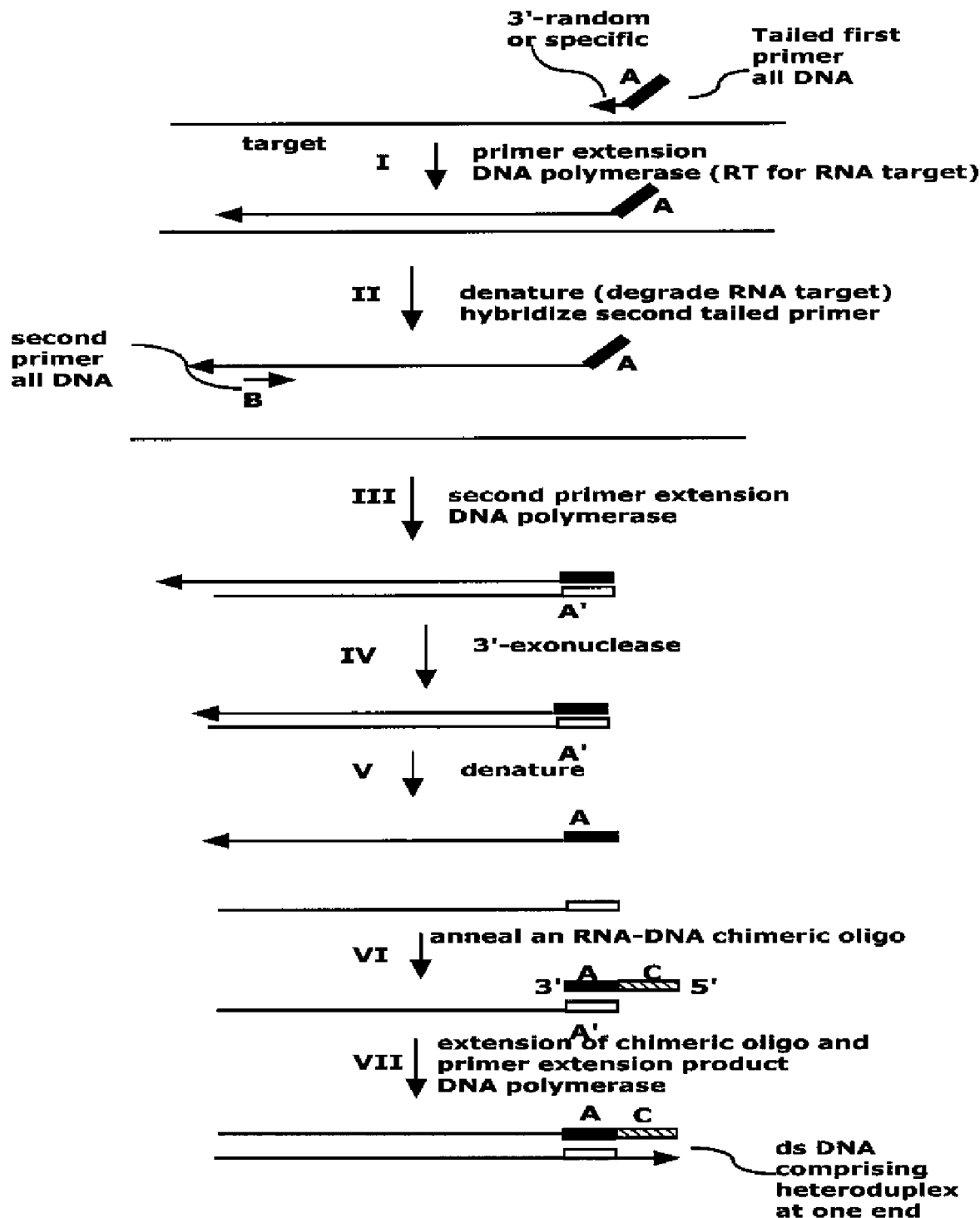

Generation of ds DNA complex with an RNA-DNA heteroduplex at one end suitable for SPIA amplification using tailed DNA primers A = 5' tail of first primer (DNA) and
    3'-end of the chimeric oligonucleotide
B = 5'-tail of second primer (DNA)
C = 5'-end RNA portion of the
    chimeric oligonucleotide Figure 18: SPIA amplification from the ds DNA with Heteroduplex at one end generated as in Figures 16 and 17

SEQUENCE LISTING

<160> NUMBER OF SEQ ID NOS: 27

<210> SEQ ID NO 1
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
ggtaatacga ctcactatag gcagacactg tcagggccgc ggtacg       46

```
<210> SEQ ID NO 2
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggtaatacga ctcactatag gcagacgtac cgcggccctg acagtg                      46

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggtaatacga ctcactatag gcagaggcga cggcagagaa cctgaatagc                  50

<210> SEQ ID NO 4
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggtaatacga ctcactatag gcagagctat tcaggttctc tgccgtcgcc                  50

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gggattttaa cggacagc                                                     18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctgatcaaag atccgtgc                                                     18

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tggttttgca ccgctac                                                      17

<210> SEQ ID NO 8
```

-continued

```
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gctgtacgtg gcgtgac                                                   17

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctgctgtttg gttcgctggt                                                20

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gctgcttccg ccttgtgct                                                 19

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctcgatgtgg tgaactttat ct                                             22

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cttgttcttc gctgtttggc t                                              21

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (26)..(31)
<223> OTHER INFORMATION: a, c, t, g, unknown or other

<400> SEQUENCE: 13
```
gguaauacga cucacuauag gcagannnnn n                              31

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 14
gguaauacga cucacuauag gcaga                                     25

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggtaatacga ctcactatag gcagaaatgc ttgaaaccgg atcag               45

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggtaatacga ctcactatag gcagaccggt ttaatcactg gtgct               45

<210> SEQ ID NO 17
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggtaatacga ctcactatag gcagaaactg gctgaccacg aagac               45

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggtaatacga ctcactatag gcagatcaag caggtagaaa gccaa               45

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 19
ctcccgaact catgtttggt                                               20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cccaaaagca actcagcaat                                               20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aacttccgtc acgacaaagg                                               20

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tgatgtcagc caacaattga g                                             21

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tcgcactcgt cgtctgatac                                               20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
acaaagtcga ggctccattg                                               20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
```

-continued

```
tatgccaaac cgaaactgtg                                                        20

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
caaggtgtcg atgatctctc a                                                      21

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 27

His His His His His His
1               5
```

ISOTHERMAL NUCLEIC ACID AMPLIFICATION METHODS AND COMPOSITIONS

CROSS REFERENCE

This application claims the benefit of U.S. Provisional Application Nos. 61/028,146, filed Feb. 12, 2008, 61/074,991, filed Jun. 23, 2008, and 61/085,811, filed Aug. 1, 2008, which applications are incorporated herein by reference in their entirety. This application is also related to the co-pending patent application Ser. No. 12/370,514 filed Feb. 12, 2009, which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Jul. 22, 2011, is named 25115-731-201Seqlist.txt and is 6,735 bytes in size.

BACKGROUND OF THE INVENTION

The quality and quantity of nucleic acid sample is important for many studies. High-throughput genomic analysis requires large amounts of template for testing, yet typically the yield of nucleic acids from individual patient samples is limited. Forensic and paleoarcheology work also can be severely limited by nucleic acid sample size. The limitation of starting material impacts the ability to carry out large scale analysis of multiple parameters, as is required for, for example, the genotyping of multiple loci in the study of complex diseases, detecting the presence or absence of specific nucleic acid species in a sample, large scale sequencing and the like. Moreover, it is well accepted that molecular analysis determination of genomic instability in various pathological condition such as cancer, is most precisely carried out in well defined cell populations, such as that obtained by laser capture micro dissection or cell sorting. Nucleic acid amplification technologies that provide global amplification of very small polynucleotide samples, for example, from one or a very few cells, may provide a solution to the limited starting materials generally available for analysis.

Likewise, the ability to amplify ribonucleic acid (RNA) is an important aspect of efforts to elucidate biological processes. Total cellular mRNA represents gene expression activity at a defined time. Gene expression is affected by cell cycle progression, developmental regulation, response to internal and external stimuli and the like. The profile of expressed genes for any cell type in an organism reflects normal or disease states, response to various stimuli, developmental stages, cell differentiation, and the like. Non-coding RNAs have been shown to be of great importance in regulation of various cellular functions and in certain disease pathologies. Such RNAs are often present in very low levels. Thus, amplification methods capable of amplifying low abundance RNAs, are of great importance.

Various methods for global amplification of DNA target molecules (e.g., whole genome amplification) have been described, including methods based on the polymerase chain reaction (PCR). See, e.g., U.S. Pat. Nos. 5,731,171; 6,365,375; Daigo et al., (2001) Am. J. Pathol. 158 (5):1623-1631; Wang et al, (2001); Cancer Res. 61:4169-4174; Zheng et al, (2001) Cancer Epidemiol. 10:697-700; Dietmaier et al (1999) Am. J. Pathol. 154 (1) 83-95; Stoecklein et al (2002) Am. J. Pathol. 161 (1):43-51; U.S. Pat. Nos. 6,124,120; 6,280,949; Dean et al (2002) PNAS 99 (8):5261-5266. However, PCR-based global amplification methods, such as whole genome amplification (WGA), may generate non-specific amplification artifacts, give incomplete coverage of loci, or generate DNA of insufficient length that cannot be used in many applications. PCR-based methods also suffer from the propensity of the PCR reaction to generate products that are preferentially amplified, and thus resulting in biased representation of genomic sequences in the products of the amplification reaction. Methods of global amplification of DNA using composite primers have been described. See e.g. U.S. patent application Ser. No. 10/824,829.

Additionally, a number of methods for the analysis of gene expression have been developed in recent years. See, for example, U.S. Pat. Nos. 6,251,639, 6,692,918, 6,686,156, 5,744,308; 6,143,495; 5,824,517; 5,829,547; 5,888,779; 5,545,522; 5,716,785; 5,409,818; EP 0971039A2; EP0878553A2; and U.S. published patent applications nos. 2002/0115088, 2003/0186234, 2003/0087251, and 2004/0023271. These include quantification of specific mRNAs, and the simultaneous quantification of a large number of mRNAs, as well as the detection and quantification of patterns of expression of known and unknown genes. RNA amplification is most commonly performed using the reverse transcriptase-polymerase chain reaction (RT-PCR) method and variations thereof. These methods are based on replication of RNA by reverse transcriptase to form single stranded DNA complementary to the RNA (cDNA), which is followed by polymerase chain reaction (PCR) amplification to produce multiple copies of double stranded DNA. However, the total amount of sample RNA that is available is frequently limited by the amount of biological sample from which it is derived. Biological samples are often limited in amount and precious. Moreover, the amount of the various RNA species is not equal; some species are more abundant than others are, and these are more likely and easier, to analyze. The ability to amplify RNA sequences enables the analysis of less abundant, rare RNA species. The ability to analyze small samples, by means of nucleic acid amplification, is also advantageous for design parameters of large scale screening of effector molecule libraries, for which reduction in sample volume is a major concern both for the ability to perform very large scale screening or ultra high throughput screening, and in view of the limiting amounts of library components. Methods of amplification from RNA templates have been described, for example in U.S. Pat. No. 6,946,251.

Sequencing of nucleic acids continues to be one of the most important and useful ways to analyze DNA and RNA samples. Recent developments have made possible highly parallel high throughput sequencing. Many of these approaches use an in vitro cloning step to generate many copies of each individual molecule. Emulsion PCR is one method, isolating individual DNA molecules along with primer-coated beads in aqueous bubbles within an oil phase. A polymerase chain reaction (PCR) then coats each bead with conal copies of the isolated library molecule and these beads are subsequently immobilized for later sequencing. See, e.g. WO04069849A2, WO05010145A2. In other cases, surface methods of conal amplification have been developed, for example, by the use of bridge PCR where fragments are amplified upon primers attached to a solid surface. These methods produce many physically isolated locations which each contain many copies of a single fragment. While these methods have provided improvements in sequencing throughput, there is a continuing need to improve the methods of obtaining samples appropriate for sequencing, and of handling, storing, and amplifying such samples. In particular, there is a need to improve methods for obtaining high throughput sequencing data for a specific set of genes or gene products from whole genome or transcriptome samples.

Therefore, there is a need for improved methods of obtaining, storing, amplifying, and analyzing DNA and RNA samples, including methods which can globally or specifically amplify DNA or RNA polynucleotide targets. The invention described herein fulfills this need.

SUMMARY OF THE INVENTION

In one aspect the present invention relates to a method for creating a partial RNA-DNA heteroduplex comprising: providing a template nucleic acid in a reaction mixture; adding an RNA-DNA chimeric primer; adding a DNA polymerase; and adding an exonuclease; wherein said DNA polymerase comprises RNA-dependent polymerase activity.

The present invention also describes a kit comprising a container containing reagents for forming a water in oil emulsion and a DNA polymerase with substantial strand-displacement activity; the kit optionally further comprising one or more all DNA primers, an RNA-DNA chimeric oligonucleotide, an exonuclease, RNA-DNA chimeric primer, RNase H, and instructions for use of said reagents. The DNA polymerase may have RNA-dependent polymerase activity. The invention also includes a kit comprising an all DNA first primer, an RNA-DNA chimeric oligonucleotide; the kit optionally further comprising a second primer, a polymerase having substantial strand-displacement activity, and RNase H.

In another aspect the invention relates to a method for producing amplified nucleic acid comprising: providing a template nucleic acid; annealing a first primer or set of first DNA primers comprising a 3' end whereby a portion of the 3' end comprises a template annealing sequence and a 5' tail sequence whereby a portion of the tail sequence comprises a sequence (A); extending said first primer or set of first primers with a DNA polymerase to create a first primer extension product or first set of DNA polymerase products; dissociating the primer extension product or products of said DNA polymerase from the template nucleic acid; annealing a second primer comprising a 3' DNA sequence and a 5' RNA sequence, whereby a portion of the 3' end comprises a randomized annealing sequence and a portion of the 5' end comprises sequence (A) or sequence (B), to said primer extension product or products; and extending said second primer with a DNA polymerase to create a second primer extension product or products to produce a double stranded DNA product or products comprising an A-A' DNA duplex at one end.

The template nucleic acid may be selected from the group consisting of DNA and RNA. The template nucleic acid may be RNA and the DNA polymerase of step (c) is an RNA dependent DNA polymerase. The dissociation step of step (d) is performed by degrading the RNA. The template nucleic acid is DNA and the DNA polymerase of step (c) can be a DNA dependent DNA polymerase. The dissociation step of step (d) may be performed by heat or chemical denaturation. The DNA polymerase may be one that does not exhibit substantial strand displacement activity. The methods herein may have each template annealing sequence of the set of primers is specific for a target or region of template nucleic acid.

The methods herein can have the template annealing sequence of the first primer comprises a random sequence. In some instances, the members of the set of first primers can each comprise a distinct 3' DNA annealing sequence, each specific for a target or region of template nucleic acid. The first primer tail sequence may not be complementary to the template nucleic acid. The 5' tail sequence of the second primer can comprise sequence (A). The 5' tail sequence of the second primer may be one that does not comprise tail sequence (A).

The method may further comprise step (g), degradation of single stranded 3' end of said first primer extension product or products in the complex of first and second primer extension products with a single stranded DNA specific 3' exonuclease. The method may further comprise step (h), the addition of a DNA polymerase with reverse transcriptase activity to create a double stranded nucleic acid with an A-A' DNA duplex at one end and an B-B' DNA-RNA heteroduplex at the other end.

The method may further comprise performing SPIA with a reaction mixture comprising RNAse H, a composite amplification primer comprising a 3' DNA portion and a 5' end whereby a portion of the 5' end comprises RNA wherein the RNase H reacts with the heteroduplex of step (h) to produce a single stranded end, and the amplification primer hybridizes to the single stranded end produced by RNaseH, and a DNA polymerase with strand displacement activity.

The first primer or set of primers described in any of the inventions herein can comprise a ligand portion at the 5' end.

Any of the methods herein can further comprise cleaving of the RNA from the DNA-RNA heteroduplex with RNase H; annealing a chimeric oligonucleotide comprising a 5' end whereby the 5' end comprises sequence (C) and a 3' end whereby the 3' end comprises the DNA sequence (B) to the double stranded nucleic acid product; extending the double stranded nucleic acid product with a DNA polymerase to produce a C-C' DNA-RNA heteroduplex; and amplifying the second primer extension product with a reaction mixture comprising RNase H, an amplification primer comprising a 3' DNA portion and a 5' end whereby a portion of the 5' end comprises RNA that hybridizes to a portion of the single stranded end produced by RNase H, and a DNA polymerase with strand displacement activity to produce an amplification product comprising sequence (B) near its 3' end and sequence (A') at the 5' end.

In another aspect the present invention relates to a method for producing amplified nucleic acid comprising: providing a template nucleic acid; annealing a first DNA primer or set of first DNA primers comprising a 3' end whereby a portion of the 3' end comprises a template annealing sequence and a 5' end whereby a portion of the 5' end comprises a DNA tail sequence (A); extending said first primer or set of first primers with a DNA polymerase to create a primer extension product or set of primer extension products; dissociation of the primer extension product or products from the template nucleic acid; annealing a second primer comprising a 3' DNA end, whereby a portion of the 3' end comprises a random template annealing sequence, and a 5' RNA end, whereby a portion of the 5' end comprises the tail sequence (A), to said primer extension product or products or to said template nucleic acid; extending said second primer with a DNA polymerase to create a second primer extension product or set of second primer extension products; and denaturing and annealing the second primer extension product or set of second primer extension products to form a stem loop structure comprising an A-A' RNA-DNA heteroduplex. The DNA polymerase may not exhibit substantial strand displacement activity. Each DNA annealing sequence in the set of first DNA primers can be specific for a target or region of the template nucleic acid. A portion of the 5' tail sequence of the first primer can be sequence (A) and a portion of the 5' tail sequence of the second primer can be sequence (A). The tail sequence may not be complimentary to the template nucleic acid.

The method can comprise the addition of a 3' single stranded DNA specific exonuclease and single strand specific RNase to degrade unincorporated primers and template nucleic acid. The methods can further comprising amplification with a reaction mixture comprising RNase H, an amplification primer comprising sequence (A'), and a DNA polymerase with strand displacement activity, wherein the amplification primer comprises a 3'-DNA sequence and a 5'-RNA sequence.

The template nucleic acid can be selected from the group consisting of RNA and DNA. In certain embodiments the template nucleic acid can be RNA and the DNA polymerase can be an RNA dependent DNA polymerase. In other embodiments the template nucleic acid can be DNA and the DNA polymerase can be a DNA dependent DNA polymerase.

In the methods described herein that include a dissociation step, such a step can be performed by degradation of the RNA. Dissociation can be carrier out or performed by chemical or heat denaturation.

In one aspect the present invention relates to a method of capturing and amplifying a target sequence or sequences comprising: providing a surface wherein a first primer or set of first primers comprising a 5' tail sequence comprising sequence (A) and a 3' template annealing sequence comprising sequence (P) are immobilized on said surface; annealing a target nucleic acid to said first primer or set of primers; extending the first primer or set of primers with a DNA polymerase to produce an immobilized primer extension product or set of immobilized primer extension products complimentary to and hybridized with the target nucleic acid to form a complex or set of complexes; dissociating the target nucleic acid-primer extension product complex or set of primer extension product complexes; annealing a second primer comprising a 3' DNA template annealing sequence (P) or set of template annealing sequences and a 5' RNA tail sequence comprising sequence (A) or sequence (B) to the immobilized DNA polymerase product or DNA polymerase products; and extending said second primer with a DNA polymerase to create a second primer extension product or set of primer extension products comprising a double stranded nucleic acid comprising a 3' DNA-DNA duplex A-A'.

The method can further comprise the step of eluting of the second primer extension product by heat or chemical denaturation. The method can also further comprise annealing an amplification primer comprising a 5' RNA sequence and a 3' DNA sequence; extending said annealed primer with a DNA polymerase; and amplifying the eluted DNA polymerase product with a reaction mixture comprising RNAse H, an amplification primer comprising a DNA portion and a 5' RNA portion, and a DNA polymerase with strand displacement activity to produce an amplified DNA product or products having a defined 5' sequence (A') or (B').

The DNA polymerase does not need to exhibit strand displacement activity.

The template nucleic acid can be selected from the group consisting of RNA and DNA. The first primer can include a spacer element between the immobilizing surface and the remaining portion of the primer, a 3' DNA end comprising a 3' DNA annealing sequence (P), and a 5' comprising a common 5' DNA sequence tail (A) or sequence tail (B) between said spacer element and annealing sequence.

The set of first primers can include a spacer element between the immobilizing surface and the remaining portion of the primer; a 3' DNA end wherein members of the set of first primers comprise unique target specific 3' DNA annealing sequences (P); and a 5' DNA end comprising a common 5' DNA sequence tail (A) or DNA sequence tail (B) between said spacer element and annealing sequence.

The annealing sequences (P) of set of first primers can each be specific to a target or region of the template nucleic acid. The first primers can be specific to one or more of the following gene targets: kinases, protein kinases, lipid kinases, phosphatases, G-protein coupled receptors, proteases, serine proteases, metalloproteases, cysteine proteases, aspartyl proteases, or cytokines. The 5' tail sequence of the first primer can be sequence (A) and the 5' tail sequence of the second primer can be sequence (B). Alternatively, the 5' tail sequence of the first primer can be sequence (A) and the 5' tail sequence of the second primer can be sequence (A). The alternative method can further comprise separating the second primer extension product or products from the first primer extension product or products by heat or chemical denaturation; annealing the second primer extension product in solution to create a stem loop structure with a DNA sequence (A')-RNA sequence (A) heteroduplex end; degrading RNA in the heteroduplex with RNase H; annealing an amplification primer to the single stranded portion of the second primer extension product wherein the amplification primer has a DNA portion and a 5' RNA portion, wherein the RNA portion of the amplification primer forms a heteroduplex with a DNA portion of the second primer extension product; extending the amplification primer with a DNA polymerase having strand displacement activity to produce an amplified product hybridized to the second primer extension product to form a double stranded nucleic acid, said amplified product forming an RNA-DNA heteroduplex at one end of the double stranded nucleic acid; and repeating the steps to produce amplified DNA. A single stranded DNA specific 3' exonuclease can be added to degrade unincorporated primers.

The surface can be selected from the group consisting of a bead, a magnetic particle, a microarray, a gene chip, and an array.

In some embodiments the method can further include degradation of the single stranded 3' end of said first primer extension product and unextended immobilized first primers with a single stranded DNA specific 3' exonuclease; cleavage of spacer element with light or chemical cleavage to release the immobilized double stranded nucleic acid from the surface; and amplifying the released double stranded nucleic acid in solution with a reaction mixture comprising RNase H, an amplification primer comprising a DNA portion and a 5' RNA portion, and a DNA polymerase with strand displacement activity to produce an amplified DNA product or products having a defined 3' sequence comprising sequence (A').

In other embodiments the method can further include degrading the single stranded 3' end of said first primer extension product or products and unextended immobilized first primers with a single stranded DNA specific 3' exonuclease; extending said first primer extension product with a DNA polymerase; and degrading RNA in the heteroduplex from the first primer extension product and the RNA portion of the second primer with RNAse H; annealing an amplification primer to the single stranded portion of the second primer extension product wherein the amplification primer has a DNA portion and a 5' RNA portion; extending the amplification primer with a DNA polymerase having strand displacement activity to produce an amplified product hybridized to the second primer extension product; and repeating these steps to produce multiple copies of amplified product or products having a defined 3' sequence comprising sequence (A').

The present invention also describes a kit comprising a container or containers comprising a first primer comprising a 3' DNA portion and a 5' DNA portion, wherein the 5' DNA portion further comprises sequence (A) and the 3' portion further comprises an annealing sequence (P); a second primer comprising a 3' DNA portion and a 5' RNA portion, wherein the 5' RNA portion further comprises sequence (A) or (B) and the 3' portion further comprises an annealing sequence (P); a DNA polymerase; a DNA dependent DNA polymerase with strand displacing activity; RNase H; and a chimeric amplification primer comprising a 3' DNA portion and a 5' RNA portion wherein the sequence of the amplification primer is substantially the same as the (A) sequence.

The present invention also describes a kit comprising a container or containers comprising a first primer comprising a 3' DNA portion and a 5' DNA portion, wherein the 5' DNA portion further comprises sequence (A) and the 3' DNA portion further comprises annealing sequence (P); a second primer comprising a 3' DNA portion and a 5' RNA portion, wherein the 5' RNA portion further comprises sequence (A) or (B) and the 3' DNA portion further comprises annealing sequence (P); a DNA polymerase; a DNA dependent DNA polymerase with strand displacing activity; a chimeric oligonucleotide comprising a 3' DNA portion substantially comprising sequence (A) or (B) and a 5' RNA portion comprising sequence (C)' RNase H; and a chimeric amplification primer comprising a 3' DNA portion and a 5' RNA portion wherein the sequence of the amplification primer is substantially the same as the (A) sequence.

The present invention also describes a kit comprising a container or containers comprising a first primer comprising a DNA portion wherein the DNA portion further comprises an annealing sequence (P); a second primer comprising a 3' DNA portion and a 5' RNA portion, wherein the 5' RNA portion further comprises sequence (A) or (B) and the 3' portion further comprises an annealing sequence (P); a DNA polymerase; a DNA dependent DNA polymerase with strand displacing activity; RNase H; and a chimeric amplification primer comprising a 3' DNA portion and a 5' RNA portion wherein the sequence of the amplification primer is substantially the same as the (A) sequence.

The present invention also describes a kit comprising an immobilized first primer comprising a 3' DNA portion and a 5' DNA portion, wherein the 5' DNA portion further comprises sequence (A), and the 3' DNA portion further comprises annealing sequence (P); a second primer comprising a 3' DNA portion and a 5' RNA portion, wherein the 5' RNA portion further comprises sequence (A) or (B); a DNA polymerase; a DNA dependent DNA polymerase with strand displacing activity; RNase H; and a chimeric amplification primer comprising a 3' DNA portion and a 5' RNA portion wherein the sequence of the amplification primer is substantially the same as the (A) sequence.

The kits of the invention can have the DNA polymerase that is an RNA dependent DNA polymerase. The kits can have a DNA dependent DNA polymerase. The kits can have a DNA polymerase that does or does not possess substantial strand displacing activity.

The kits can comprise a first primer where the 3' DNA portion of the first primer comprises a random sequence. The kits can comprise a first primer where the 3' DNA portion of the first primer comprises a specific sequence. The kits can comprise a first primer where the 3' DNA portion of the first primer comprises a set of specific sequences. The kits can comprise a first primer which further comprises a ligand.

The kits can comprise a second primer where the 3' DNA portion of the second primer comprises a random sequence. The kits can comprise a second primer where the 3' DNA portion of the second primer comprises a specific sequence.

The kits can comprise a second primer where the 3' DNA portion of the second primer comprises a set of specific sequences.

The kits can further comprise a single stranded DNA specific 3' exonuclease. The kits can further comprise an RNase specific for single and double stranded RNA.

In another aspect an amplification method comprises forming a polynucleotide strand comprising a sequence (A) at its 5' end and complementary sequence (A') at its 3' end wherein sequence (A) comprises RNA within a mixture comprising other polynucleotides that are single stranded; treating said polynucleotide so as to intramolecularly anneal the (A) sequence to the (A') sequence; purifying the polynucleotide by degrading the other polynucleotides by treating the mixture with one or more enzymes that degrade single stranded polynucleotides; and performing SPIA amplification with the purified polynucleotide from step (c) using sequence (A') as a priming site for the SPIA amplification.

In yet another one aspect an amplification method comprises: obtaining a polynucleotide strand comprising sequence (B') at its 3' end; annealing a chimeric oligonucleotide comprising a 3' DNA portion and a 5' RNA portion, wherein the 5' portion comprises sequence (C), and the 3' portion comprises sequence (B); extending the polynucleotide strand with a RNA dependent DNA polymerase to add a DNA sequence (C') to the polynucleotide strand; and performing SPIA amplification using the product of step (c) as the SPIA substrate using sequence (C') as a priming site for SPIA amplification.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention may be obtained by reference to the following detailed description that sets forth illustrative embodiments, in which the principles of the invention are utilized, and the accompanying drawings of which:

FIG. 1 illustrates the initial steps of a method for producing amplified DNA by way of generating a single primer isothermal linear amplification (SPIA) substrate using an all DNA first primer with a sequence tail (A) and an annealing sequence (P), a DNA-RNA chimeric second primer with a sequence tail (A) or (B), and a DNA template.

FIG. 2 illustrates methods for producing a SPIA substrate for producing amplified DNA with a defined sequence tail (A') from the product of FIG. 1.

FIG. 3 illustrates an alternative method of producing amplified DNA from the product of FIG. 1.

FIG. 4 illustrates methods for producing captured and immobilized DNA using immobilized all DNA first primers with sequence tails (A) and annealing sequences (P), a template nucleic acid, and a DNA-RNA chimeric second primer with a sequence tail (A) or (B).

FIG. 5 illustrates methods for generating amplified DNA from immobilized DNA of FIG. 4 having a defined 3' sequence (A').

FIG. 6 illustrates an alternative method for generating amplified DNA from immobilized DNA of FIG. 4 having a defined 3' sequence (A') in which the SPIA substrate is cleaved from the surface prior to amplification.

FIG. 7 illustrates the initial steps of a method for producing a SPIA substrate using an immobilized all DNA first primer with sequence tail (A), a DNA-RNA chimeric second primer with the same sequence tail (A), and a template nucleic acid.

FIG. 8 illustrates a method for producing a stem loop SPIA substrate from the product of FIG. 7.

FIG. 9 illustrates a method of producing a SPIA substrate with a defined sequence (A) at its 5' end using an all DNA first primer with a sequence tail (A), a DNA-RNA chimeric second primer with a sequence tail (B), an RNA template, and a chimeric DNA/RNA amplification primer.

FIG. 10 illustrates a method of producing amplified DNA with a defined sequence (A') at its 3' end and a defined sequence (B) at its 5' end using a chimeric oligonucleotide.

FIG. 11 illustrates a method of producing a SPIA substrate with a 5' ligand for immobilization, functionalization, or capture and a defined 5' sequence (A) using a ligand attached all DNA first primer with a sequence tail (A), a DNA-RNA chimeric second primer with sequence tail (B) and an RNA template.

FIG. 12 illustrates a method of producing a SPIA substrate with a 5' ligand, a defined sequence (A) at its 5' end, and a defined sequence (B') at its 3' end using a ligand attached all DNA first primer with tail sequence (A), a DNA-RNA chimeric second primer with a sequence tail (B), a DNA-RNA chimeric oligonucleotide with a DNA sequence (B) at its 3' end and an RNA sequence (C) at its 5' end, and an RNA template.

FIG. 13 illustrates a method of producing a SPIA substrate from a DNA template using an all DNA first primer with a randomized annealing sequence (P) and without a sequence tail, and a DNA-RNA chimeric second primer with a sequence tail (B).

FIG. 14 illustrates a method of producing a SPIA substrate from a DNA template using an all DNA first primer with a target specific annealing sequence (P) and lacking a sequence tail, and a DNA-RNA chimeric second primer with a sequence tail (B).

FIG. 15 illustrates a method of producing a SPIA substrate with a 5' ligand for immobilization, functionalization, or capture and a defined 5' sequence (A) using a ligand attached all DNA first primer with a sequence tail (A) and a randomized annealing sequence (P), a DNA-RNA chimeric second primer with sequence tail (B) and an DNA template.

FIG. 16 illustrates a method of producing a SPIA substrate from a target nucleic acid for generation of amplified DNA having a defined 5' sequence (A) using an all DNA first primer with a sequence tail (A) and a randomized or target specific annealing sequence (P), an all DNA second primer, and an RNA-DNA chimeric oligonucleotide with DNA sequence (A) at its 3' end and RNA sequence (C) at its 5' end.

DETAILED DESCRIPTION OF THE INVENTION

Introduction

Figure 17:
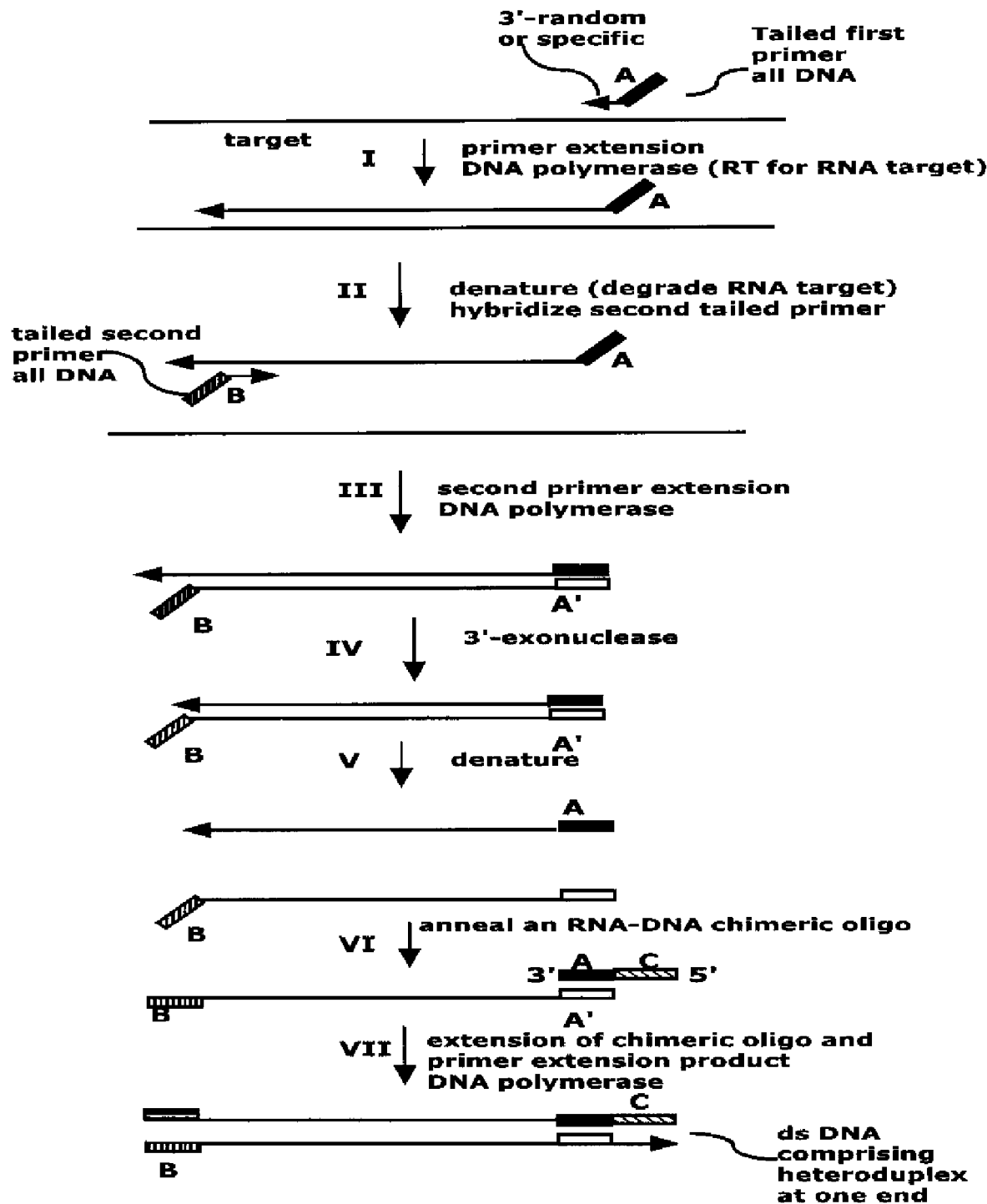
FIG. 17 illustrates a method of producing a SPIA substrate from a target nucleic acid for generation of amplified DNA having a defined 5' sequence (A) and a defined 3' sequence (B) using an all DNA first primer with a sequence tail (A) and a randomized or target specific annealing sequence (P), an all DNA second primer having a tail sequence (B), and an RNA-DNA chimeric oligonucleotide with DNA sequence (A) at its 3' end and RNA sequence (C) at its 5' end.

This invention provides new methods of amplifying nucleic acids. The invention also provides for systems reaction mixtures, and kits relating to these methods. The methods of the invention generally incorporate single primer isothermal amplification (SPIA). SPIA is an isothermal amplification method described, for example, in U.S. Pat. Nos. 6,692, 918, 6,251,639, 6,946,251 and 7,354,717. In some instances SPIA amplification generally involves a chimeric RNA-DNA amplification primer, RNase H, and a DNA polymerase enzyme to produce amplified DNA product. The SPIA amplification generally amplifies the sequences downstream of the hybridization site of the SPIA primer on the nucleic acid to which the SPIA primer binds. SPIA is a rapid and effective method of isothermal, linear amplification that can be used to produce amplified DNA that is representative of DNA or RNA from a variety of sources, for example, genomic DNA or the messenger RNA transcripts.

The methods of the present invention generally utilize all-DNA first primers that are designed to hybridize to a nucleic acid target, often referred to as a template, that has sequences to be amplified. Prior methods have described how to generate a substrate for SPIA from a target nucleic acid by using chimeric RNA-DNA first primers. The methods of the present invention can be useful, for example, for amplifying specific sequences within the target nucleic acid. The methods of the invention are also useful for multiplex amplification, performing the simultaneous amplification of multiple specific sequences. The number of specific sequences can be, for example, 2-10, 10-100, 100-1,000, 1,000-10,000, 10,000-100,000 or more than 100,000. In some cases, the number of specific sequences can be for example at least 2, 20, 200, 2,000, 20,000, 50,000, 100,000, 200,000 or more.

In some embodiments of the invention the all-DNA first primer is a tailed primer, for example, having a tailed sequence (A) that generally does not hybridize to the target nucleic acid. The use of a tailed all-DNA first primer having, for example, sequence (A) allows, for example, the preparation of amplified product having either sequence (A) or its complement (A') at one end.

In some embodiments of the invention, the all-DNA first primer is attached to a solid surface, or solid substrate such as a microarray or a bead. The all-DNA first primer can be attached, for example, to a microarray, such as an oligonucleotide microarray, such as a microarray described by Affymetrix, Agilent, or NimbleGen. The different regions of the microarray can each have different all-DNA primer sequences that can hybridize to different regions of a target nucleic acid sample. These primer sequences can then be extended by the methods of the invention to produce substrates for SPIA amplification. The use of solid phase-bound all-DNA primers to produce SPIA substrates is useful for multiplex amplification of a subset of sequences within a target DNA population. For example, the solid phase or microarray may comprise primers that can hybridize to a subset of genes in a sample that represents the genome of an organism or a population of organisms. This method results in the SPIA amplification of only that subset of genes or factions thereof. The SPIA amplified subset of genes or fraction thereof, can then be analyzed, for example, by sequencing, for example by the newly developed massively parallel high throughput next generation sequencing methods and instruments such as the sequencing methods described by Illumina, 454 (Roche), and Applied Biosystems (ABI) and in U.S. Pat. Nos. 7,211,390; 6,355,431; 5,750,341; 5,969,119; 6,274,320; 6,258,568; 6,210,891; and 6,306,597 herein incorporated by reference in their entirety. These same methods can be applied to RNA, for example to SPIA amplification of a subset of the messenger RNA transcripts from the transcriptome of an organism. The same type of parallel multiplex amplification described for microarrays can be carried out on beads by having a plurality of beads containing all-DNA primers. The beads can be used in the same manner as above, and in some cases may be useful for conal amplification and/or archiving of sequences in the sample.

When the all-DNA primers are bound to a solid surface, in some embodiments, the primers have a tail sequences, for example, sequence (A), that are 5' to the primer sequences. By incorporating a tailed sequence, substrates for SPIA amplification and SPIA amplification products having either an (A) sequence, or the complementary (A') sequence can be produced. The generation of amplified product comprising as sequence (A) or (A'), e.g. a universal sequence, can be useful for the further processing and/or analysis of the sample. For example, the universal sequence can be used for sequencing, e.g. as the priming site for sequencing by polymerization and pyrosequencing.

In some cases, the primer bound to the solid surface is bound covalently. In some cases, the primer is bound via a spacer or a linker. In some cases, the primer is bound by a spacer having a cleavable group, where the group can be cleaved, for example chemically, by heat, or by light.

One aspect of the invention comprises using an all-DNA first DNA primer having a 5' tail sequence (A), and using a second chimeric RNA-DNA primer having a 5' RNA tail sequence (A). Extension of the second primer along the first primer extension product produces a second primer extension product having a 5' RNA portion with sequence (A), and a 3' DNA end comprising sequence (A') complementary to (A). Denaturing and annealing can then result in the formation of stem-loop structures by intramolecular hybridization of the (A) and (A') sequences. The reaction mixture thus produced can then be treated with an exonuclease specific for single stranded DNA, and with an RNase that is specific for single and or double stranded RNA such as, for example, RNase 1. This process may result in the degradation of the primers and other products that do not form the stem-loop structure. The products that do form stem-loop structures may not be degraded by the enzymes. The stem-loop products can act as SPIA substrates by using a chimeric SPIA amplification primer that anneals to the (A') DNA sequence of the stem-loop product. Cleavage of the RNA portion of the RNA-DNA heteroduplex stem structure of the stem-loop products are cleaved by RNase H thus freeing the priming site for binding of the SPIA amplification chimeric primer and enabling isothermal linear SPIA amplification. Thus, this procedure results in the clean-up of the reaction mixture from the undesired products as well as target nucleic acid and unincorporated primers, for subsequent amplification, which can result in a purer amplification products and or a better yield of amplification products. The method of using the stem-loop can also be used with embodiments that employ a solid substrate as described herein.

Exemplary Methods of the Invention

Initial Steps for Generation of SPIA Substrate Using all DNA First Primer

In one aspect of the present invention, target nucleic acids are amplified by SPIA using an all DNA first primer. The all-DNA first primer may comprise a 5'-tail sequence, e.g. sequence (A), and a 3'-annealing sequence (P) as described previously. In other cases, the primer comprises an annealing sequence and no tail sequence. The annealing sequence may comprise a random sequence suitable for binding to any or substantially any sequence portion of the target nucleic acid such as for example random hexamers or random decamers. In other cases, the annealing sequence may be designed to hybridize to a specific region of the target nucleic acid.

In some embodiments the target nucleic acid comprises DNA. In some cases, the DNA comprises genomic DNA such as for example the human genomic DNA from a subject or set of subjects. In other cases, the DNA comprises a subset of a genome. In still other cases, the target DNA comprises cDNA generated from an RNA source. In some cases, the target nucleic acid comprises RNA. In some cases, the RNA comprises messenger RNA or total RNA. In some cases, the RNA comprises a transcriptome or a subset of a transcriptome.

In some embodiments, a set or sets of more than one unique non-random all DNA first primer is used such that multiple regions of the target nucleic acid are amplified. This is often referred to in the art as multiplex amplification because multiple different amplification products are produced in a single reaction. The set or sets of target-specific primers of the invention may comprise a set of related sequences for hybridizing to a set of related genes, introns, exons, splice variants and the like. For example, the annealing sequences may hybridize to nucleic acid encoding serine/threonine kinases or their complement. In some cases, the annealing sequences may be randomized at certain positions and specific at other positions, such that they may hybridize to more than one member of a set of homologous target nucleic acids.

The all-DNA first primer may be annealed to a target nucleic acid and extended using a polymerase to generate a first primer extension product. In some cases, the polymerase may comprise no, or substantially no, strand displacement activity, for example to avoid whole genome or transcriptome amplification. In other cases, a polymerase may be chosen that possesses a substantial amount of strand displacement activity, for example to enable whole genome or transcriptome amplification. In some cases, a substantially thermostable polymerase that is maximally active above about 60° C. such as Taq polymerase for example may be used, for example to enable higher processivity or avoid problems with secondary structure within target nucleic acid. In other cases, a polymerase that is slightly thermostable that is maximally active between 40° C. and 60° C. may be used. In still other cases, a mesophilic polymerase that is maximally active below 40° C. may be used to extend the first and or second primer. In some cases, an RNA-dependent DNA polymerase may be used, while in other cases a DNA dependent DNA polymerase may be used. In some cases, it may be advantageous to use a polymerase that does not exhibit either 3'-5' or 5'-3' exonuclease activity. In other cases 3'-5' or 5'-3' exonuclease activity may be advantageous. In some cases, the polymerase used to generate the first primer extension product may be a reverse transcriptase. In some cases, the target nucleic acid may be removed after generation of the first primer extension product by heat or chemical denaturation and or degradation. In other cases, the target nucleic acid may be removed by enzymatic methods. In some cases the DNA polymerase comprises both DNA-dependent DNA polymerase activity and RNA-dependent RNA polymerase.

In some embodiments of the present invention, target nucleic acids are amplified using a chimeric DNA-RNA second primer. The chimeric second primer may comprise an RNA segment and a DNA segment. In some cases, the RNA segment is generally at the 5' end and the DNA segment is generally at the 3' end of the chimeric primer. In some cases, a portion of the RNA segment comprises a tail sequence that may comprise the same or substantially the same sequence (A) as the tail sequence of the all DNA first primer. In some cases, the tail sequence comprises a different tail sequence (B) than the tail sequence (A) of the all DNA first primer.

In some cases, a portion of the DNA segment of the chimeric second primer comprises a target nucleic acid annealing sequence. In some cases, the target nucleic acid annealing sequence is random such that it may hybridize with any, or substantially any, region of the target nucleic acid. In other embodiments, the annealing sequence is specific for a region of the target nucleic acid. In still other embodiments, a set of chimeric DNA-RNA second primers comprising a set of specific annealing sequences may be utilized to amplify a set of target nucleic acid regions in a multiplex fashion.

In some cases the chimeric DNA-RNA second primer may be annealed to a target nucleic acid or to the first primer extension product and extended using a polymerase to generate a second primer extension product. The polymerase may be a thermostable or mesophilic DNA dependent DNA polymerase as described above. Additionally, the polymerase may or may not exhibit substantial strand displacement or exonuclease activity.

In one aspect of the present invention, methods are provided for creating an RNA-DNA heteroduplex, for example on a nucleic acid, such as a target nucleic acid. The RNA-DNA heteroduplex may be useful, for example in providing a substrate for SPIA amplification, or for providing a defined 3', 5' or 3' and 5' end to the nucleic acid. The method may comprise providing a template nucleic acid in a suitable reaction mixture as provided herein, adding an RNA-DNA chimeric primer, adding a DNA polymerase or allowing a DNA polymerase previously present in the reaction mixture to extend the RNA-DNA chimeric primer, and adding an exonuclease. In some cases, the method may further comprise purifying the resulting product or products by for example standard nucleic acid purification techniques known in the art such as Agencourt magnetic beads. In some cases, the method may further comprise amplifying the product by adding an RNA-DNA chimeric amplification primer, RNase H, and a DNA-polymerase exhibiting substantial strand displacement activity.

A schematic example of an embodiment of the invention relating to the initial steps of a method for generating amplified DNA by way of producing a substrate for single primer isothermal linear amplification (SPIA) is shown in FIG. 1. Step I shows the annealing of an all DNA first primer comprising a 5'-tail of sequence (A) and a 3'-target specific, or randomized, sequence for annealing to a target nucleic acid (P). In some embodiments it may be advantageous for tail sequence (A) to be designed to minimize hybridization with the target nucleic acid. Further, in some embodiments, the tail sequence of the first primer comprises only a portion of the 5' end of the primer. Likewise, in some embodiments, the sequence (P) comprises only a portion of the 3' end of the first primer.

In one aspect, a single first primer with a specific annealing sequence (P) may be used to amplify a target sequence. In other embodiments, a set of first primers each with a different specific annealing sequence may be used to amplify multiple target sequences in the same reaction. It is anticipated that the methods of the present invention may be use to amplify many specific target sequences in the same reaction in a multiplexed fashion. In some embodiments the target sequences to be amplified represent a set of genes or gene expression products (e.g. RNA, or mRNA), or fragments thereof, of interest. Such sets of genes or gene expression products may include but are not limited to kinase, phosphatases, G-protein coupled receptors, proteases, cytokines, genes or gene expression products related to a specific metabolic or signaling pathway, genes or gene expression products related to multiple metabolic or signaling pathways, genes or gene expression products related to cancer, hereditary disease, metabolic disorder, ageing and age related disorders, normal or pathogenic specific developmental stages, specific differentiation stages, tissue specific, or any gene, gene expression product, or fragment thereof; or combination of genes, gene expression products, or fragments thereof of interest. It is anticipated that the number of target sequences amplified in this fashion can be as few as 1 to as many as tens of thousands including any number between one and 99,999, or more than tens of thousands of target sequences. In some embodiments 2, 3, 4, 5, 6, 7, 8, 9, 10-20, 20-30, 30-50, 50-80, 80-100, 100-200, 200-400, 400-500, 500-1,000, 1,000-2,000, 2,000-4,000, 4,000-5,000, 5,000-10,000, 10,000-20,000, 20,000-50,000 or more than 50,000 target sequences can be amplified in multiplex fashion. In some cases, at least 2; 20; 200; 2,000; 20,000; 200,000; 2,000,000 or more sequences may be amplified in multiplex fashion using the methods of the present invention.

The annealing sequence (P) can act as a primer for a DNA polymerase to extend the first primer as also depicted in step I to create a first primer extension product. In some embodiments, the target nucleic acid comprises DNA and the DNA polymerase is a DNA dependent DNA polymerase. In other embodiments, the target nucleic acid comprises RNA and the DNA polymerase is an RNA dependent DNA polymerase or a reverse transcriptase. In some embodiments, especially wherein the annealing sequence (P) of the first primer is randomized, it may be advantageous to use a DNA polymerase that does not exhibit strand displacement activity to avoid whole or substantially whole genome or transcriptome amplification. In other embodiments, especially wherein randomized annealing sequences are used, it may be advantageous to use a DNA polymerase that exhibits strand displacement activity to provide whole or substantially whole genome or transcriptome amplification. In some cases, it may be advantageous to use a thermostable polymerase, in other cases it may be advantageous to use a thermolabile polymerase. In some cases it is advantageous to use polymerases devoid of 5'-exonuclease activity. In some cases, a polymerase devoid of 5'-exonuclease activity may be useful to avoid cleaving or degrading the 5'-tail of a first or second primer or the displaced primer extension product or products.

Step II shows the separation of the target nucleic acid from the newly synthesized primer extension product followed by annealing of a second primer. In the case of a DNA target, target nucleic acid may be separated from the first primer extension product by heat or chemical denaturation. In the case of an RNA target, target nucleic acid may be degraded by heat, an enzyme, or an enzyme combination such as RNaseH and RNase 1. Alternatively, RNA target nucleic acid may be removed by heat or chemical denaturation.

The second primer as shown in step II may contain a 5' tail sequence (A) that is the same or substantially the same as the tail sequence of the first primer, or may contain a tail sequence (B) that is substantially different than the tail sequence of the second primer. The term substantially the same and substantially different as used herein describes two or more nucleic acid sequences that are substantially the same if each are capable of hybridizing to the other's complimentary sequence, or different if each do not show significant hybridization to the other's complimentary sequence. For example, a sequence substantially similar to sequence (A) would be capable of hybridizing to the complement of sequence (A) also known as (A'). In some cases, it may be advantageous to design the tail sequence such that it does not hybridize to the target nucleic acid or to the first primer extension product.

The second primer may also contain an annealing sequence (P) that is either random or target specific. In some embodiments the use of a set of second primers with multiple target specific annealing sequences is anticipated. As described previously for sequence (P) of the first primer, the simultaneous amplification of multiple genes or gene expression products or fragments thereof is anticipated by this method using multiple target specific annealing sequences or a random annealing sequence.

In the embodiment shown in FIG. 1, the second primer is a DNA-RNA chimeric primer in which the 5'-end is RNA and the 3'-end is DNA. In some cases, the portion of the 5'-end of the second primer that is RNA corresponds to the portion of the 5'-end that comprises the tail sequence (A) or (B). In other cases, a portion of the tail sequence of the second primer is RNA and a portion of the tail sequence is not RNA, for example a portion of the tail sequence may be DNA. Likewise, in some cases the 3'-end of the second primer that is DNA corresponds to the annealing sequence (P). In other cases, a portion of the annealing sequence may be RNA.

The annealed second primer may then be extended, as depicted in step III, by the use of a DNA polymerase to create a second primer extension product. In some cases it may be advantageous to use a polymerase that does not exhibit strand displacement activity to avoid whole or substantially whole genome or transcriptome amplification. In other cases, it may be advantageous to use a polymerase that does exhibit strand displacement activity to enable whole or substantially whole genome or transcriptome amplification. The double stranded nucleic acid product such as that depicted in FIG. 1 can be a useful product or, in the case of multiplexed primers or random primers, can be a useful set of products. The products have defined double stranded region (A)/(A') at one end, when the all-DNA first primer comprises a tail sequence (A), and the second primer extension product strand has a tailed region comprising sequence (A) or (B), and comprises an RNA tailed sequence. The double stranded nucleic acid product or products can, for example, be amplified as described below. The products can be analyzed before or after amplification, for example, to determine the sequence of portions of the template nucleic acid.

Amplification of Target Nucleic Acid Using all-DNA First Primer

The double stranded nucleic acid product of the method depicted in FIG. 1 may be further manipulated and amplified by single primer isothermal linear amplification. In some embodiments, a 3'-exonuclease specific for single stranded DNA such as exonuclease 1 or a polymerase that exhibits substantial single stranded DNA 3'-exonuclease activity such as T4 DNA polymerase can be used to degrade any remaining non hybridized 3'-DNA of the first primer extension product. The first primer extension product may then be extended with a polymerase that exhibits substantial reverse transcriptase activity such as for example Bst polymerase such that the first primer extension product is extended along the tail of the second primer and the first primer extension product is substantially hybridized to the tail sequence of the chimeric DNA-RNA second primer. The first and second primer extension products may form a double stranded nucleic acid with a chimeric DNA-RNA heteroduplex at one end. The double stranded nucleic acid with a chimeric DNA-RNA heteroduplex may comprise a SPIA substrate. The SPIA substrate may be amplified using the SPIA method. By way of example, the double stranded nucleic acid may be contacted with a chimeric amplification primer, an RNAse such as RNAse H that can degrade the RNA portion of a DNA-RNA heteroduplex, and a polymerase with strand displacement activity. The chimeric amplification primer may comprise a DNA portion and a 5'-RNA portion wherein the chimeric amplification primer comprises a sequence which is substantially the same as sequence (A) or (B) or a portion of sequence (A) or (B).

In some embodiments a double stranded nucleic acid product comprising a hybridized first and second primer extension product as depicted in FIGS. 1 and or 2, may be amplified, or a region of the first and second primer extension product may be amplified, by a method known to the art that is not SPIA. The amplification methods include but are not limited to PCR, linear PCR, SPIA, rolling circle amplification, loop-mediated isothermal amplification, ligation mediated rolling circle amplification and the like.

The formation of a substrate for single primer isothermal linear amplification (SPIA) from the double stranded nucleic acid product of the method depicted in FIG. 1 is depicted in FIG. 2. In FIG. 2, step I shows the use of a single stranded DNA specific 3'-exonuclease such as, but not limited to, exonuclease 1 or the 3'-exonuclease activity of a DNA polymerase such as, but not limited to, T4 DNA polymerase. The exonuclease or exonuclease activity may remove the single stranded 3'-nucleotides from the 3'-end of the first primer extension product which are not hybridized to the second primer extension product.

The method depicted in FIG. 2 further comprises step II whereby a DNA polymerase with reverse transcriptase activity (e.g. Bst polymerase) further extends the first primer extension product to produce a sequence (A') or (B') complimentary to the tail sequence of the second primer (A) or (B). This extension produces a double stranded DNA product with two defined ends, referred to as the first primer end in which the first primer is incorporated and the second primer end in which the second primer is incorporated.

The method further comprises step III, whereby SPIA is used to amplify the further extended first primer extension product of step II. In some embodiments of the SPIA method, an RNA-DNA heteroduplex degrading enzyme such as, but not limited to, RNase H is used to remove the RNA portion of the second primer in the RNA-DNA heteroduplex. Then a third primer, referred to as the amplification primer, is annealed to the 3' single stranded portion of the first primer extension product. The third primer, the amplification primer, comprises a 5'-RNA portion and a 3'-DNA portion. A DNA polymerase with strand displacement activity such as has been described for example in U.S. Pat. Nos. 6,251,639 and 6,692,918 may then extend the primer to create a third primer extension product while displacing the second primer extension product. The enzyme additions to carry out step III may be done sequentially and repeatedly to produce SPIA products, or preferably the RNase H, amplification primer, and strand displacing polymerase are added as a mixture and the reaction is allowed to proceed under conditions that allow amplification as described in U.S. Pat. Nos. 6,251,639 and 6,692,918. The amplification products of the SPIA method as described in FIG. 2 all have a 3' end sequence (A') that is the compliment of the first primer tail sequence (A), when the all DNA first primer is a tailed primer comprising sequence (A).

Stem Loop Nucleic Acid Structures for SPIA Amplification

Alternatively, in some embodiments, the double stranded nucleic acid product of FIG. 1 may be used to generate amplified nucleic acid by way of a different method than depicted in FIG. 2. In this method, the chimeric DNA-RNA second primer may comprise a tail sequence (A) that is the same or substantially the same as the tail sequence (A) of the all DNA first primer. The primer annealing sequences may be specific or random sequences. The double stranded nucleic acid product of FIG. 1 in which the tail sequences of the first and second primer are substantially the same comprises a second primer extension product that may be separated from the first primer extension product by heat, chemical or enzymatic means and annealed to form a stem-loop structure.

The stem loop structure may comprise a DNA-RNA heteroduplex of RNA sequence (A), and complementary DNA sequence (A'). The annealing reaction may then be treated with a single strand DNA specific 3'-exonuclease such as for example exonuclease 1, and a single stranded nucleic acid specific RNase such as for example RNase 1. The exonuclease and RNase treatment may provide a clean-up step in that a substantial portion of extraneous nucleic acids such as the target nucleic acid, and the first and second primers are degraded. The degradation products may then be removed by a number of methods known in the art for removing nucleotide degradation products from polynucleic acids such as size exclusion spin columns, ion-exchange resin, ultrafiltration, dialysis, or any method known to the art. In some cases, removal of degradation products may not be required. In other cases, additional steps may be used to remove other undesirable compounds from the stem loop structure such as pyrophosphate and the like. In still other cases, the exonuclease and RNase may be inactivated by heat or chemical denaturation.

The resulting stem loop structure, for example, the purified stem loop structure may then be amplified by SPIA by first degrading the RNA portion of the DNA-RNA heteroduplex with for example RNase H, thus yielding a substantially linear nucleic acid comprising a sequence A' at the 3'-end. Amplification further comprises providing a chimeric amplification primer and a DNA polymerase with strand displacement activity. The chimeric amplification primer may comprise a DNA portion and a 5'-RNA portion wherein the chimeric amplification primer comprises a sequence which is substantially the same as sequence (A) or a portion of sequence (A).

Alternatively, the stem loop structure may be amplified by any other method of nucleic acid amplification known to the art such as but not limited to rolling circle template amplification, polymerase chain reaction (PCR), and linear polymerase chain reaction.

FIG. 3 depicts an embodiment for producing amplification products by the use of the SPIA method by way of a stem-loop intermediate product. Here, the tailed regions of both the first primer and the second primer comprise the sequence (A). In this case the hybridized first and second primer extension products of FIG. 1 are denatured, for example, by heat or chemical denaturation and subsequently are allowed to anneal. The result of having the same tailed sequence for the first and second primers is that the 3'-end and 5'-end of the second primer extension product comprises complimentary or substantially complementary sequences such that they are capable of hybridization to one another to form a stem-loop structure. Hybridization to form the stem loop structures is carried out under conditions that are readily determined by one skilled in the art.

The annealing step can be carried out in such manner that the unimolecular nature of the self annealing of the second primer extension product is preferred over renaturation of the double stranded product of the method of FIG. 1. The self annealed product thus forms a stem loop type structure. In some cases the length of time or rate of the annealing process, the addition of DNA binding proteins or enzymes, the use of chaotropic or cosmotropic solutes, or the concentration of first and primer extension products may be varied in order to promote stem-loop structure formation. Self annealing may be favored for certain sizes of the second primer extension product. In some cases, self annealing is favored by having a second primer extension product size that is smaller than about 100 kilobases or about 10 kilobases. In some cases, self annealing is favored for second primer extension product having sizes that are smaller than about 1 kilobase. In other embodiments, self annealing is favored for second primer extension product sizes are smaller than about 500 bases or between 10 and 500 bases. Where the stem-loop formation does occur for a given size range, this property can be used in order to select for that size range at the exclusion of the others, as the products which do not form the stem-loop structure may be susceptible to degradation by the enzymes described above. In some cases, the process selects for second primer extension products less than about 50, 80, 100, 200, 400, 500, 800, 1,000, 2,000, 4,000, 5,000, 8,000, 10,000, or 20,000 bases.

Step II shows the process of degradation of extraneous polynucleotides such as the target nucleic acid, the first primer extension product, and unincorporated primers. Degradation of the reaction components described above, is accomplished by using one or more enzymes that degrade single stranded nucleic acids, and to not degrade or do not substantially degrade double-stranded nucleic acids. Extraneous DNA polynucleotides may be removed by digestion with 3'-single stranded DNA specific exonucleases. Since sequences (A) and (A') of the second primer extension product are hybridized to form a double stranded portion, the stem-loop products are not degraded by these enzymes. Extraneous RNA polynucleotides may be removed by digestion with RNase 1. The combination may be used to remove extraneous chimeric primers such as the second primer depicted in FIG. 1.

Step III shows a method for removing the RNA from the stem loop structure created in step I. RNase H is used to degrade the RNA portion of the DNA-RNA heteroduplex formed by the stem loop structure. This leads to an essentially linear polynucleic acid with a defined 3'-sequence (A'). The step of degradation of the RNA in the RNA-DNA heteroduplex by RNase H may be carried out in the reaction mixture for carrying SPIA amplification of the primer extension product as described below.

In step IV, SPIA amplification is performed in a manner as described in U.S. Pat. Nos. 6,251,639 and 6,692,918 using a mixture comprising a chimeric amplification primer that hybridizes to the A' sequence of step III, a strand displacing DNA polymerase, and RNase H.

In an alternative step not depicted, a chimeric oligonucleotide may be employed to allow the generation of amplified DNA with a defined 5' end. The suitable chimeric oligonucleotide may comprise a 3'-DNA sequence (A) capable of hybridizing with the (A') sequence of the linear polynucleic acid product of step III. The chimeric oligonucleotide may also comprise a 5'-RNA tail sequence (C). The linear polynucleic acid is extended with an RNA dependent DNA polymerase creating an RNA DNA heteroduplex of DNA sequence (C') and RNA sequence (C) which may be amplified by the SPIA method using a mixture comprising RNase H which cleaves RNA tail sequence C, an amplification primer that hybridizes to DNA tail sequence C', and a suitable polymerase. The amplified DNA products may then comprise a defined sequence (A) at or near its 5'-end.

Capture of Target Sequence on Immobilized First Primers

In some embodiments of the present invention the first primer is immobilized on a surface. The surface may be a chip or a slide such as for example a gene chip or a microarray. In other cases, the surface may comprise a bead such as for example an agarose bead, a polymeric bead, polystyrene beads, or a magnetic bead. In still other cases, the surface may be any surface known to the art capable of being derivatized with oligonucleotides. In some cases, the first primers are immobilized to discrete sites. In some cases, the discrete sites comprise immobilized primers with a specific known annealing sequence or set of sequences such that target nucleic acids of known sequence are immobilized at known discrete sites. The immobilized first primer, or primers, may be useful for capturing a targeted nucleic acid sequence (e.g. RNA or DNA) for subsequent amplification or analysis. The subsequent amplification may comprise SPIA, PCR, rolling circle template amplification or linear PCR. The immobilization may be performed by a number of methods known to the art. For example, the first primer, or primers, may be covalently linked to the surface by a photolabile, heat labile, reduction labile, oxidation labile, acid labile, or base labile linker. Alternatively, the immobilized first primer, or primers, may be hybridized to another nucleic acid or nucleic acid analog such as a locked nucleic acid, pyroanosyl nucleic acid, or peptide nucleic acid that is covalently linked to the surface. The immobilized first primer, or primers, may comprise a linker, as described in the following.

In some embodiments, because the captured target sequences that are produced are isolated as discrete populations, subsequent conal amplification products can be generated and analyzed, for example sequenced, in a parallel manner. Therefore, in some embodiments, at least at least 100, 500, 1000, 10000, 50000, 100000, 300000, 500000, or 1000000 populations of conal amplification products can be analyzed in parallel. The skilled artisan will appreciate that various methods can be suitable for parallel analysis of conal amplicons. Generally, such methods can produce a discrete detectable signal that can be associated or linked to individual populations of conal amplicons.

In some embodiments the target nucleic acid comprises DNA. In some cases, the DNA comprises genomic DNA such as for example the human genomic DNA from a subject or set of subjects. In other cases, the DNA comprises a subset of a genome. In still other cases, the DNA comprises cDNA generated from an RNA source. In some cases, the target nucleic acid comprises RNA. In some cases, the RNA comprises messenger RNA or total RNA. In some cases, the RNA comprises a transcriptome or a subset of a transcriptome.

In one aspect of the present invention the first primer comprises an immobilized all-DNA first primer. The first primer may comprise an annealing sequence (P), and a tail sequence (A). The annealing sequence may be random such that it is capable of hybridizing to substantially any portion of the target nucleic acid. The random annealing sequences may comprise for example random hexamers or random decamers. The annealing sequences alternatively may comprise specific sequences for hybridizing to a specific region of the target nucleic acid. In some cases, the annealing sequence of first primers comprise a set of specific target annealing sequences, wherein each first primer of the method comprises a specific target annealing sequence, such that a specific set of target nucleic acid regions are captured and or subsequently amplified. The sets may comprise a set of related sequences for hybridizing to a set of related genes, introns, exons, splice variants and the like. For example, the annealing sequences may hybridize to nucleic acid encoding serine/threonine kinases or their complement. In some cases, the annealing sequences may be randomized at certain positions and specific at other positions, such that they may hybridize to more than one member of a set of homologous target nucleic acids.

The immobilized all DNA first primer may be annealed to a target nucleic acid and extended using a polymerase to generate a first primer extension product. In some cases, the polymerase may comprise substantially no strand displacement activity. In other cases, a polymerase may be chosen that possesses a substantial amount of strand displacement activity. In some cases, a substantially thermostable polymerase that is maximally active above about 60° C. such as Taq polymerase for example may be used, for example to enable higher processivity or avoid problems with secondary structure within primers and or target nucleic acid. In other cases, a polymerase that is slightly thermostable that is maximally active between 40° C. and 60° C. may be used. In still other cases, a mesophilic polymerase that is maximally active below 40° C. may be used to extend the first and or second primer. In some cases, an RNA-dependent DNA polymerase may be used, while in other cases a DNA dependent DNA polymerase may be used. In some cases, it may be advantageous to use a polymerase that does not exhibit either 3'-5' or 5'-3'-exonuclease activity. In other cases 3'-5' or 5'-3'-exonuclease activity may be advantageous. In some cases, the polymerase used to generate the first primer extension product may be a reverse transcriptase. In some cases, the use of a polymerase with high processivity may be advantageous. In some cases, the target nucleic acid may be removed after generation of the first primer extension product by heat or chemical denaturation and or degradation. In other cases, the target nucleic acid may be removed by enzymatic methods.

In some embodiments of the present invention, target nucleic acids are amplified using a chimeric DNA-RNA second primer. The chimeric second primer may comprise an RNA segment and a DNA segment. In some cases, the RNA segment is generally at the 5' end and the DNA segment is generally at the 3' end of the chimeric primer. In some cases, a portion of the RNA segment comprises a tail sequence that may comprise the same or substantially the same sequence (A) as the tail sequence of the all DNA first primer. In some cases, the tail sequence comprises a different tail sequence (B) than the tail sequence (A) of the all DNA first primer.

In some cases, a portion of the DNA segment of the chimeric second primer comprises a target nucleic acid annealing sequence. In some cases, the target nucleic acid annealing sequence is random such that it may hybridize with any, or substantially any, region of the target nucleic acid. In other embodiments, the annealing sequence is specific for a region of the target nucleic acid. In still other embodiments, a set of chimeric DNA-RNA second primers comprising a set of non-random annealing sequences may be utilized to amplify a set of target nucleic acid regions in a multiplex fashion as described previously.

In some cases the chimeric DNA-RNA second primer may be annealed to a target nucleic acid or to the immobilized first primer extension product and extended using a polymerase to generate an immobilized second primer extension product. The polymerase may be a thermostable or mesophilic DNA dependent DNA polymerase as described above. Additionally, the polymerase may or may not exhibit substantial strand displacement or error correcting activity.

FIG. 4 depicts a method for using DNA primers immobilized on a solid substrate that can capture of target nucleic acid from solution. Step I shows a surface to which all DNA first primers are immobilized. The first primers comprise a DNA tail sequence (A), and a DNA target nucleic acid annealing sequence (P) as described above. While the solid substrate is depicted in FIG. 4 as a spherical particle, it is to be understood that the method depicted can be carried out on a solid substrate of any suitable geometry, including wells, planar surfaces, and other geometries described herein. The surface may comprise, for example a particle or bead, a nanoparticle, a microarray, a glass slide, a chip or cassette, a polynucleic acid chip, a fused fiber optic array, a polymer, or any type of surface known to the art to which nucleic acid, such as an oligonucleotide may be attached.

The method of attachment may or may not require a linker element between the first primer and the surface. The linker element may be a spacer element such as by way of example ethylene glycol, polyethylene glycol, polyvinyl, polystyrene, polyether, a saturated carbon chain, an unsaturated carbon chain, a nucleic acid sequence, an amino acid sequence or any other spacer element capable of linking a nucleic acid to a surface known to the art. The spacer element may also comprise a cleavable element for removal of immobilized first primers from the surface. The cleavable spacer element may be cleaved through the action of a strong base, a strong acid, heat, light, reduction, oxidation, enzymatic reaction, or any of a variety of other methods known to those skilled in the art.

Step I also shows the annealing of a target nucleic acid to the immobilized first primer. The target nucleic acid may comprise RNA or DNA. The target nucleic acid may comprise fragments from an RNA or DNA sample. The annealing may occur between the sequence (P) of the first primer and a sequence on the target nucleic acid. The sequence on the primer that anneals to the target nucleic acid may be a random sequence, a target specific sequence, or a set of target specific sequences. In some embodiments a plurality of specific primer sequences are used, wherein, for example, different primer sequences are immobilized on different regions of a microarray or different sequences are immobilized on different beads.

In step II, the first primer is extended by the action of a polymerase to create a first primer extension product. In the case of a DNA target nucleic acid, it may be advantageous to use a DNA dependent DNA polymerase. In the case of an RNA target nucleic acid, it may be advantageous to use an RNA dependent DNA polymerase or reverse transcriptase. In some embodiments it may be advantageous to utilize a polymerase that does or does not exhibit substantial strand displacement activity. It may also be advantageous to extend the first primer with a thermostable or a thermolabile polymerase. The thermostable polymerase may exhibit higher rates of polymerization, fewer difficulties with secondary structure of target nucleic acid or first primer, or greater fidelity. The thermolabile polymerase may exhibit greater fidelity, greater rates of polymerization, or enable facile removal of polymerase activity by heat denaturation. In some cases, the use of other nucleic acid binding proteins, or reaction additives, during the extension step is anticipated. The proteins or additives include but are not limited to DMSO, DMF, cations, anions, glycerol, single-stranded nucleic acid binding proteins including but not limited to T4 gene 32 protein (gp32), buffers, and salts.

The target nucleic acid and the first primer extension product are then separated by heat, chemical, or enzymatic treatment, and a second DNA-RNA chimeric primer is then annealed to the first primer extension product in step III. The primer may comprise a 5' tail sequence (A) or (B) and an annealing sequence (P) as described previously. The annealed second primer then may be used to extend the primer to create a second primer extension product complementary to the entire, or a portion of the entire, first primer extension product as depicted in step IV. As described for extension of the first primer, it is anticipated that for certain aspects of the present invention, the DNA polymerase used to create the second primer extension product may be thermostable, thermolabile, strand displacing, non strand displacing, high fidelity, highly processive, or any combination thereof.

Generation of Amplified DNA from Captured Target Sequences

In some embodiments of the present invention, the immobilized double stranded nucleic acid product depicted in FIG. 4 may be used to generate amplified DNA. Amplified DNA may be generated by a number of methods known to the art. Preferred amplification methods include but are not limited to PCR, SPIA, rolling circle amplification, loop-mediated isothermal amplification, ligation mediated rolling circle amplification and the like. In the case of SPIA amplification, the method of amplification may further comprise providing a single stranded DNA specific 3'-exonuclease such as exonuclease 1, or a polymerase with 3'-exonuclease activity such as for example T4 DNA polymerase. The exonuclease or exonuclease activity may degrade the 3'-portion of the first primer extension product that is not hybridized to the second primer extension product. The first primer extension product may then be extended with a polymerase such as Bst that exhibits reverse transcriptase activity. The extension may generate a DNA-RNA heteroduplex at one end. The immobilized first and second primer extension products comprising a DNA-RNA heteroduplex at one end may be amplified by SPIA by providing an RNase such as RNaseH to cleave the RNA portion of the heteroduplex, a chimeric amplification primer, and a polymerase with strand displacing activity. The chimeric amplification primer may comprise a DNA portion and a 5'-RNA portion wherein the chimeric amplification primer comprises a sequence which is substantially the same as sequence (A) or (B) or a portion of sequence (A) or (B). The amplified nucleic acid may comprise a sequence tail (A') at the 3'-end.

A method of generating amplified DNA using SPIA from the immobilized first and second primer extension products depicted in FIG. 4 is shown in FIG. 5. This method generates amplified product directly from an extension product of the primer immobilized to the solid substrate. Step I of FIG. 5 depicts the use of a single stranded DNA specific 3'-exonuclease such as exonuclease 1 or the 3'-exonuclease activity of a DNA polymerase such as T4 DNA polymerase to remove the portion of the 3'-end of the first primer extension product that is not hybridized to the second primer extension product. In step II, the immobilized first primer extension product or first primer extension products are then extended by a DNA polymerase that exhibits reverse transcriptase activity. A DNA polymerase that exhibits reverse transcriptase activity includes but is not limited to Bst polymerase. Step III depicts the use of RNase H to cleave the RNA portion of the DNA-RNA heteroduplex. This provides a site for annealing an amplification primer to the priming site A' or B', or a portion of site A' or B', as depicted in step IV. Thus amplified DNA products with a defined 3'-end sequence (A') may be generated by SPIA methods using a reaction mixture comprising RNase H, a DNA polymerase with strand displacement activity, and a chimeric amplification primer.

Generation of Amplified DNA from Immobilized Target Sequence Using Solution Phase SPIA In one aspect of the present invention, the immobilized double stranded first and second primer extension product depicted in FIG. 4 may be amplified by solution phase SPIA. In some cases, the double stranded nucleic acid product depicted in FIG. 4 may be treated with a single stranded DNA specific 3'-exonuclease to remove the 3'-portion of the first primer extension product that is not hybridized to the second primer extension product. The immobilized first and second primer extension product may then be cleaved from the surface releasing the first and second primer extension product into the solution phase. The cleavage may be performed by application of heat, base, acid, reducing agent, oxidation or any method known to the art. The cleavage may occur at or within the linker between the nucleic acid portion of the all DNA first primer and the surface. Alternatively, the cleavage may occur before exonuclease treatment.

The first primer extension product may then be extended using a polymerase such as Bst that exhibits substantial reverse transcriptase activity. The extension may produce a double stranded nucleic acid a portion of which comprises a DNA-RNA heteroduplex. The double stranded nucleic acid may be amplified using any method of nucleic acid amplification known to the art such as but not limited to PCR, linear PCR, SPIA, rolling circle amplification, loop-mediated isothermal amplification, ligation mediated rolling circle amplification and the like. Alternatively, the extension of the first primer extension product in the complex with the second primer extension product may be extended with a DNA polymerase comprising an RNA-dependent DNA polymerase activity, such as for example Bst polymerase, prior to the release from the surface, such that the released complex comprises an RNA-DNA heteroduplex at one end.

FIG. 6 depicts an alternative method for producing amplified DNA using SPIA from the immobilized first and second primer extension products depicted in FIG. 4. Here, the products of the first steps of the method are cleaved from the solid surface such that the SPIA amplification occurs in solution rather than occurring on the solid surface. While the figure depicts cleavage occurring after the exonuclease step of the method, it is understood that the cleavage can occur at any suitable step before or after this step. Step I depicts a 3'-exonuclease step as described previously for degrading extraneous nucleic acids including but not limited to target nucleic acid and unincorporated primers, as well as trimming the unhybridized 3'-end of the first primer extension product. Step II depicts the use of a cleaving step to release the hybridized first and second primer extension products from the surface or particle to which they are immobilized. The cleavage mechanisms anticipated include chemical, enzymatic, or light as described previously. Following cleavage, the remaining steps are carried out in solution. Step III depicts the use of a DNA polymerase such as but not limited to Bst polymerase to extend the first primer extension product. Step IV depicts the use of RNase H to produce an amplification primer hybridization site. Step V depicts the use of SPIA to generate amplified DNA products having a defined 3'-DNA sequence (A').

Capture of Target Sequences for Formation of Stem Loop Structures

In some embodiments of the present invention an all DNA first primer comprising a tail sequence (A) immobilized to a bead or surface may be annealed to capture target nucleic acid sequences and extended, and a chimeric second primer may be annealed comprising a tail sequence (A) which is the same or substantially the same as the tail sequence of the all DNA first primer and extended. The capture and first and second primer extension steps may be performed by the methods described previously. The second primer extension products may be used further to generate a stem loop nucleic acid structure. The stem loop nucleic acid structure may be amplified by a number of methods known the art as described previously such as but not limited to PCR, linear PCR, SPIA, rolling circle amplification, loop-mediated isothermal amplification, ligation mediated rolling circle amplification and the like.

FIG. 7 depicts an alternative method for amplification of captured of target nucleic acid using immobilized primers. This method utilizes the same sequence, e.g. sequence (A) in the 5'-tail of both the first and the second primers. As described above, this method produces a product which can form a stem-loop structure, which facilitates clean-up of the desired products prior to SPIA amplification. Step I depicts the use of immobilized all DNA first primers with a 5'-tail sequence (A) and a 3'-template annealing sequence (P) for annealing to a target nucleic acid as described previously. Step II depicts the use of an RNA or DNA dependent DNA polymerase to extend the first primer and produce a first primer extension product as described previously. In step III, the target nucleic acid is removed by heat, enzymatic, or chemical means, and a DNA-RNA chimeric second primer comprising a 5'-tail sequence (A) and 3' template annealing sequence (P) as described previously. For the method depicted in this figure, it may be advantageous to ensure that the 5'-tail sequence of the second primer is identical to or substantially the same as the 5'-tail sequence of the first primer. In step IV the annealed second primer is extended with a DNA polymerase as described previously to yield a second primer extension product.

Generation of Stem Loop Amplification Substrate from Captured Target Sequences

In some embodiments of the present invention, the second primer extension product or products of a captured target sequence as described previously, may be utilized to generate amplified DNA. The amplified DNA may be separated from the first primer extension product by heat or chemical denaturation, and annealed to form a stem loop structure. In some cases, primers and other extraneous nucleic acids may be removed from the reaction by degradation before or after separation and annealing of the second primer extension product. For example, unextended first and second primers and target nucleic acid may be degraded with a single stranded DNA specific 3'-exonuclease and or a single and or double stranded RNA specific RNase as described previously. The stem loop structure may be resistant to degradation by the exonuclease and RNase because of a lack of a single stranded 3' DNA or RNA end. The stem loop structure may then be amplified by any methods known in the art such as but not limited to PCR, linear PCR, SPIA, rolling circle amplification, loop-mediated isothermal amplification, ligation mediated rolling circle amplification and the like.

FIG. 8 depicts a method of utilizing the products depicted in FIG. 7 for the generation of a substrate suitable for DNA amplification using the SPIA method. Step I is an optional step. In step I, a 3'-exonuclease is used as described previously to remove extraneous nucleic acids, and trim the 3'-end of the first primer extension product. In step II, the second primer extension product is separated from first primer extension product by heat or chemical means. The second primer extension product is then annealed to create a stem loop structure as described previously. Exonucleases and RNase 1 can then be added to remove extraneous polynucleotides and unincorporated primers. The stem loop structure then acts as a suitable substrate for SPIA amplification to generate amplified DNA. Alternatively, a chimeric oligonucleotide may be employed to generate amplified DNA with a defined 5'-end as described in FIG. 3 alternative step.

Amplification of RNA Using a Chimeric Second Primer

In some embodiments of the present invention, amplified DNA can be produced from an RNA template using an all DNA first primer comprising a tail sequence (A) or (B) and an annealing sequence (P) as described previously for amplification of a specific sequence, multiplex amplification, or whole transcriptome amplification. In some cases, the first primer extension product is formed by providing a RNA dependent DNA polymerase. In some cases, further steps may include the removal of RNA target nucleic acid by heat, chemical, heat and chemical, or enzymatic means. For example, RNA template may be removed by providing RNase H and RNase 1 to degrade any single and or double stranded RNA and any RNA portion of an RNA-DNA heteroduplex. In one aspect of the present invention a chimeric DNA-RNA second primer as described previously comprising a tail sequence (B) that is substantially different from the tail sequence (A) in the all DNA first primer may be annealed to the first primer extension product and extended as described previously to create a second primer extension product. In some cases, a single stranded DNA specific 3'-exonuclease may be provided to degrade unincorporated first and second primers as well as any unhybridized 3'-end of the first primer extension product. The degraded 3'-end of the first primer extension product may then be extended using a polymerase such as for example Bst that exhibits reverse transcriptase activity to generate a double stranded nucleic acid product comprising the first and second primer extension product and a DNA-RNA heteroduplex at one end. The first and second primer extension product may then be used to generate amplified DNA using a number of methods known to the art such as but not limited to PCR, linear PCR, SPIA, rolling circle amplification, loop-mediated isothermal amplification, ligation mediated rolling circle amplification and the like. In some cases, SPIA is used to generate amplified products comprising a defined 3'-end sequence (A').

FIG. 9 depicts a method for producing amplified DNA from an RNA template using a SPIA method using an all DNA first primer of tail sequence (A), a DNA-RNA chimeric second primer of tail sequence (B), and an RNA target nucleic acid. It is also anticipated that in some cases, a second primer tail sequence (A) may be employed. In this method, the first primer is annealed to the target in a target specific or random fashion and is extended with an RNA dependent DNA polymerase or reverse transcriptase to generate a first primer extension product. Target nucleic acid is removed by RNase H and RNase 1 as depicted, or any other RNases or combination thereof known in the art, which could be easily inactivated so as not to interfere with the following steps of the methods of the invention. It is also anticipated that other methods may be employed to remove RNA target nucleic acid selectively such as a thermal or chemical method. Following removal of target nucleic acid, the chimeric second primer comprising RNA containing tail sequence (B) is annealed to the first primer extension product and extended. A single stranded DNA specific 3'-exonuclease is then employed to trim back the unhybridized 3'-end of the first primer extension product, and a third DNA polymerase step is then used to create a double stranded hybridized product with a defined DNA-RNA heteroduplex end of DNA sequence (B') and RNA sequence (B), and a DNA-DNA duplex end of sequence (A) and (A'). This product of the method depicted in FIG. 9 may then be amplified DNA of a defined 3'-sequence (A') is then produced by the SPIA method using a mixture of RNase, amplification primer, and a suitable polymerase.

Generation of Amplified DNA Having a Defined 5' and 3' End

In some embodiments of the present invention, a double stranded nucleic acid comprising a first and second primer extension product and further comprising a DNA-RNA heteroduplex at one end may be used to generate amplified DNA comprising a defined 5' and 3'-end. In some cases, the RNA portion of the DNA-RNA heteroduplex may be cleaved or degraded by an enzyme such as RNase H. The method may further include providing a DNA-RNA chimeric oligonucleotide. The chimeric oligonucleotide may comprise a 5'-segment and a 3'-segment. The 5'-segment may comprise RNA and the 3'-segment may comprise DNA. The 3'-DNA segment may comprise a sequence (B) the same or substantially the same as the RNA portion of the DNA-RNA heteroduplex degraded by RNase H. The 5'-RNA segment may comprise a sequence (C) that is substantially different from previously described sequences (A) and (B). The chimeric oligonucleotide may be annealed to the first primer extension product such that sequence (B) of the chimeric oligonucleotide hybridizes with sequence (B') of the first primer extension product. The first primer extension product may then be extended by a polymerase as described previously. The resulting double stranded nucleic acid comprising a first and second primer extension product and a DNA-RNA heteroduplex may then be amplified by a number of methods known to the art such as but not limited to PCR, linear PCR, SPIA, rolling circle amplification, loop-mediated isothermal amplification, ligation mediated rolling circle amplification and the like. In some cases, SPIA may be used to generate amplified products comprising a defined 3' end sequence (A') and a defined sequence at or near its 5'-end comprising sequence (B).

FIG. 10 depicts an alternative method of generating amplified DNA using the SPIA method from the product the method depicted in FIG. 9. In this method, RNase H is used to degrade the RNA portion of the DNA-RNA (B')-(B) heteroduplex and a chimeric oligonucleotide comprising 3'-DNA sequence (B) and a 5'-RNA sequence (C) is annealed to the DNA sequence (B'). The first primer extension product is then extended using a suitable polymerase to create a double stranded nucleic product with a DNA-RNA heteroduplex at one end of DNA sequence (C') and RNA sequence (C) and a DNA-DNA duplex at the other end of sequence (A) and (A'). Following the extension step, SPIA amplification is then employed using a mixture of RNaseH, an RNA-DNA chimeric amplification primer, and a suitable polymerase as described previously. In this case, the products of the SPIA amplification have a defined 3' sequence (A') and a defined 5' sequence (B).

Generating a SPIA Substrate with a Ligand

In some embodiments of the present invention a double stranded nucleic acid comprising a first and second primer extension product and further comprising a ligand may be generated. The ligand may be useful for capture of the double stranded nucleic acid, purification, or further downstream manipulation such as sequencing for example. The ligand may be but is not limited to a biotin molecule or other small organic molecule like a fluorophore, a peptide, a nucleic acid, a magnetic particle, a bead, a nanocrystal or quantum dot, a protein, or any other ligand capable of being linked to a nucleic acid covalently or non-covalently. In some cases, the ligand is linked to an all DNA first primer comprising a tail sequence (A) and an annealing sequence (P) as described previously. The all DNA first primer is annealed to a target nucleic acid (e.g. RNA or DNA) and extended using a polymerase as described previously to generate a first primer extension product linked to a ligand. The first primer extension primer may comprise random sequences, a specific sequence, or a set of multiple specific sequences as described previously.

In some cases, a DNA-RNA chimeric second primer comprising a tail sequence (A) or (B) and an annealing sequence as described previously may be annealed to the first primer extension product and extended using a DNA polymerase to generate a second primer extension product. The first and second primer extension product may further be treated with a single stranded DNA specific 3'-exonuclease to generate a double stranded nucleic acid comprising the first and second primer extension products, a ligand, and a DNA-RNA heteroduplex. In some embodiments, the double stranded nucleic acid product may be amplified using a number of methods known to the art such as but not limited to PCR, linear PCR, SPIA, rolling circle amplification, loop-mediated isothermal amplification, ligation mediated rolling circle amplification and the like. In some cases SPIA may be used to generate an amplified DNA product with a 3'-end comprising a defined sequence (A').

FIG. 11 depicts a method for using a ligand attached to an all DNA first primer, a DNA-RNA chimeric second primer and an RNA template nucleic acid to generate amplified DNA products using SPIA. The method follows the method outlined in FIG. 9 with exception of the ligand attached all DNA first primer of tail sequence (A). Various nucleic acid ligands anticipated by the present invention are known to the art and include but are not limited to biotin, proteins such as antibodies, antibody fragments, avidin, streptavidin, maltose binding protein, S-protein, enzymes, peptides such as hexahistidine (SEQ ID NO: 27), myc tag, flag tag, HA tag, or any affinity tag or member of any pair of binding agents known in the art, fluorophores, particles, nanoparticles, magnetic particles, or other nucleic acid sequences. Methods for attaching ligands to nucleic acid primers are known to the art. The ligand may be used for attachment to a solid substrate, for example for archiving and clonal expansion. The ligand may be useful for functionalizing the first primer extension product for further chemical or enzymatic manipulation, or for purification of the first and or second primer extension products. The SPIA amplified products of the method depicted in this figure have a 3' end comprising the defined sequence (A').

Generating a SPIA Substrate with a Ligand and Amplified Product with Two Defined Ends In some embodiments of the present invention a double stranded nucleic acid SPIA substrate may be generated having a ligand and a two defined ends comprising a first and second primer extension product. The ligand may be useful for capture of the double stranded nucleic acid, purification, or further downstream manipulation such as sequencing for example. The ligand may be but is not limited to a biotin molecule or other small organic molecule like a fluorophore, a peptide, a nucleic acid, a magnetic particle, a bead, a nanocrystal or quantum dot, a protein, or any other ligand capable of being linked to a nucleic acid covalently or non-covalently. In some cases, the ligand is linked to an all DNA first primer comprising a tail sequence (A) and an annealing sequence (P) as described previously. The all DNA first primer is annealed to a target nucleic acid (e.g. RNA or DNA) and extended using a polymerase as described previously to generate a first primer extension product linked to a ligand. The first primer extension primer may comprise random sequences, a specific sequence, or a set of multiple specific sequences as described previously.

In some cases, a DNA-RNA chimeric second primer comprising a tail sequence (A) or (B) and an annealing sequence as described previously may be annealed to the first primer extension product and extended using a DNA polymerase to generate a second primer extension product. The first and second primer extension product may further be treated with a single stranded DNA specific 3'-exonuclease to generate a double stranded nucleic acid comprising the first and second primer extension products, a ligand, and a DNA-RNA heteroduplex.

The double stranded nucleic acid product may be further treated with RNase H to degrade or cleave the RNA portion of the DNA-RNA heteroduplex. In some cases, a DNA-RNA chimeric oligonucleotide comprising a 5'-RNA sequence (C) and a 3'-DNA sequence (B) as described previously may be annealed to the first primer extension product. The first primer extension product may be further extended with a polymerase exhibiting substantial reverse transcriptase activity such as for example Bst polymerase. The further extension may generate a double stranded first and second primer extension product comprising a ligand and DNA-RNA heteroduplex. In some embodiments, the double stranded extension product may be amplified using a number of methods known to the art such as but not limited to PCR, linear PCR, SPIA, rolling circle amplification, loop-mediated isothermal amplification, ligation mediated rolling circle amplification and the like. In some cases SPIA may be used to generate an amplified DNA product with a 3'-end comprising a defined sequence (A') and a 5'-end comprising sequence (B).

FIG. 12 depicts a method as in the previous figure for producing amplified DNA using a ligand attached all DNA first primer. In this method a chimeric oligonucleotide is used to enable the generation of amplified DNA using the SPIA method comprising a defined 3'-end sequence (A') and a defined 5'-end sequence (B).

Amplification of a Target Nucleic Acid Using an Non-tailed all DNA First Primer

In some embodiments of the present invention, a method for amplification of a target nucleic acid (DNA or RNA) may comprise using an all DNA first primer that comprises an annealing sequence (P) as described previously but the all DNA first primer may not comprise a tail sequence. The all DNA first primer may be annealed to a specific, random or multiple regions of the target nucleic acid and extended with a polymerase as described previously to generate a first primer extension product. In some cases, a set of first primers may be used for amplification of a set of target sequences within the target nucleic acid in a multiplex fashion. A DNA-RNA chimeric second primer comprising a tail sequence (A) or (B) and an annealing sequence (P) as described previously may then be annealed to the first primer extension product and or the target nucleic acid and extended with a polymerase. The first and second primer extension products, primers, and target nucleic acid may then be treated with a single stranded DNA specific 3'-exonuclease such as exonuclease 1 and or a single and or double stranded RNA specific RNase such as RNase 1 to degrade unincorporated primers, unhybridized target nucleic acid, unhybridized 3'-ends of the first primer extension product, and unincorporated primers. The remaining target nucleic acid, and first and second primer extension products may then be extended with a polymerase exhibiting substantial reverse transcriptase activity such as for example Bst polymerase to generate a double stranded nucleic acid with a DNA-RNA heteroduplex. In some cases, the double stranded nucleic acid may be amplified using a number of methods known to the art such as but not limited to PCR, linear PCR, SPIA, rolling circle amplification, loop-mediated isothermal amplification, ligation mediated rolling circle amplification and the like. In some cases SPIA may be used to generate an amplified DNA product with a 3'-end comprising a defined sequence (A') and in some cases a 5'-end comprising sequence (B).

FIG. 13 depicts a method of producing amplified DNA using the SPIA method with an all DNA first primer where the first primer has no tail sequence, but comprises a template annealing sequence (P). The template annealing sequence may be target specific or randomized. The method further comprises a DNA-RNA second primer of tail sequence (B), an annealing sequence for annealing to the first primer extension product, and a DNA target nucleic acid. The use of randomized annealing sequences may require the use of a non-strand displacing polymerase in order to avoid whole genome amplification. In some cases, a non-strand-displacing polymerase may enable sequence specific amplification when using a sequence-specific annealing sequence with one primer (first or second) and a randomized annealing sequence with another primer. In some cases, a non-strand-displacing polymerase may enable sequence specific amplification when using a sequence-specific annealing sequence with an all DNA first primer and a random annealing sequence with an RNA-DNA chimeric second primer. Alternatively, whole genome amplification may be desired in which case it may be advantageous to employ a strand displacing polymerase to generate the first or second primer extension products or both. In some cases, the use of a strand displacing polymerase is advantageous to generate longer primer extension products or to enable the generation of second primer extension products.

FIG. 14 depicts a method of producing amplified DNA using the SPIA method with a sequence specific non-tailed all DNA first primer comprising an annealing sequence (P). In step I, the first primer is hybridized to a DNA target nucleic acid, and extended using a DNA polymerase. The method further comprises a DNA-RNA chimeric second primer comprising tail sequence (B) and an annealing sequence for annealing to the first primer extension product. The annealing sequence of the chimeric second primer may be a randomized sequence. In step II, the double stranded complex of the DNA target nucleic acid and the first primer extension product is denatured, and the second primer is annealed to the first primer extension product. FIG. 14 also shows that some of the second primer may anneal to the other DNA strand, not containing the target sequence, or other portions of the DNA strand comprising the target sequence, but that most of the products from these reactions may result in SPIA amplified products. The second primer is extended in step III with a DNA polymerase. The DNA polymerase may lack strand displacement activity. In step IV a 3'-exonuclease is used to remove the non-hybridized portion of the first primer extension product. In step V, a DNA polymerase is used to extend the first primer extension product. The product of step V can then be used as a substrate for SPIA amplification using a chimeric amplification primer as shown in step VI. and a DNA target nucleic acid.

Additional Amplification Strategies Using All DNA First Primers

In FIG. 15, a ligand attached all DNA first primer comprising a 5' tail sequence (A), a 3'-annealing sequence (P), and a DNA template nucleic acid. This figure depicts a method for amplifying two stands of the DNA template nucleic acid simultaneously. The ligand attached primer also allows functionalization and or purification of one of the strands to enable amplification of either strand selectively. In the first step, the ligand attached all DNA first primer is annealed to a target DNA and extended with a DNA dependent DNA polymerase to create a first primer extension product. The method further comprises denaturing the hybridization complex between the target nucleic acid and the first primer extension product, and annealing a second primer to the first primer extension product as well as the target DNA. The second primer comprises a 5'-segment a portion of which comprises RNA comprising a tail sequence (B) and a 3'-segment a portion of which comprises DNA comprising an annealing sequence (P) as described previously. The second primer may then be extended by a DNA dependent DNA polymerase to create a second primer extension product. In some cases, the first and second primer extension product form a double stranded nucleic acid product. In other cases, the second primer extension product and the target DNA form a double stranded nucleic acid product. The method further comprises treating the double stranded nucleic acid products with a single stranded DNA specific 3'-exonuclease and a DNA polymerase to create two double stranded nucleic acid products. In one case the double stranded nucleic acid product comprises a ligand at one end and a DNA-RNA heteroduplex comprising sequence (B) and (B') at the other end. In another case, the double stranded nucleic acid product does not comprise a ligand at one end. These double stranded nucleic acid products may act as substrates for SPIA amplification by providing a reaction mixture comprising RNase H, a chimeric amplification primer comprising a 5'-RNA segment and a 3'-DNA segment as described previously, and a DNA polymerase with substantial strand displacing activity.

FIG. 16 depicts a method of producing amplified DNA using the SPIA method without the use of a DNA-RNA chimeric second primer. In this method, an all DNA first primer of 5'-tail sequence (A) and a random or target specific template nucleic acid annealing sequence (P) is used to form the first primer extension product hybridized to a DNA or RNA template nucleic acid as previously described. In step II, the template nucleic acid is separated from the first primer extension product and an all DNA second primer comprising an annealing sequence that is annealed to the first primer extension product. The resulting double stranded first and second primer extension products are optionally treated with a 3'-exonuclease as described, the exonuclease is removed or inactivated and the first and second primer extension products are denatured. A chimeric oligonucleotide comprising a 5'-RNA sequence (C) and a 3'-DNA sequence (A) is then annealed to the second primer extension product, generating a substrate suitable for subsequent SPIA amplification. The SPIA amplifications products comprise a defined 5'-sequence (A).

FIG. 17 depicts an alternative method for producing amplified DNA using the SPIA method without the use of a DNA-RNA chimeric second primer. This method allows for the production of amplified product with defined sequences at or near both ends of the amplified product. The method comprises an all DNA second primer comprising a 5'-tail sequence (B) and a 3'-template annealing sequence (P). The method generates a substrate suitable for subsequent SPIA amplification. The SPIA amplification products comprise a defined 3'-sequence (B') and a defined 5'-end comprising sequence (A). In step I, an all DNA first primer comprising a 5'-segment comprising tail sequence (A) is annealed to a target nucleic acid and extended with a DNA polymerase to create a first primer extension product. In step II, the first primer extension product is denatured from the target nucleic acid, and an all DNA second primer as described hereinabove is annealed to the first primer extension product. In some cases, the target nucleic acid comprises RNA which is degraded in this step by heat, enzymes, chemical degradation etc. In step III, the second primer is extended with a DNA polymerase to create a double stranded nucleic acid product. Step IV depicts an optional step in which the double stranded nucleic acid product is treated with a single stranded DNA specific 3'-exonuclease. In step V, the double stranded nucleic acid product of step III or IV is denatured by heat or chemical means. In step VI a DNA-RNA chimeric olignucleotide (or "oligo") as described previously is annealed to the second primer extension product. In step VII, the chimeric oligonucleotide is extended to yield a third primer extension product comprising a 3'-portion comprising sequence (B') and a 5'-portion comprising RNA comprising sequence (C). Step VII further comprises extending the second primer extension product such that the 3'-segment comprises sequence (C'). Step VII yields a double stranded nucleic acid comprising sequence (B) and (B') at one end and a DNA-RNA heteroduplex comprising sequence (C) and (C') at the other end.

Figure 18:
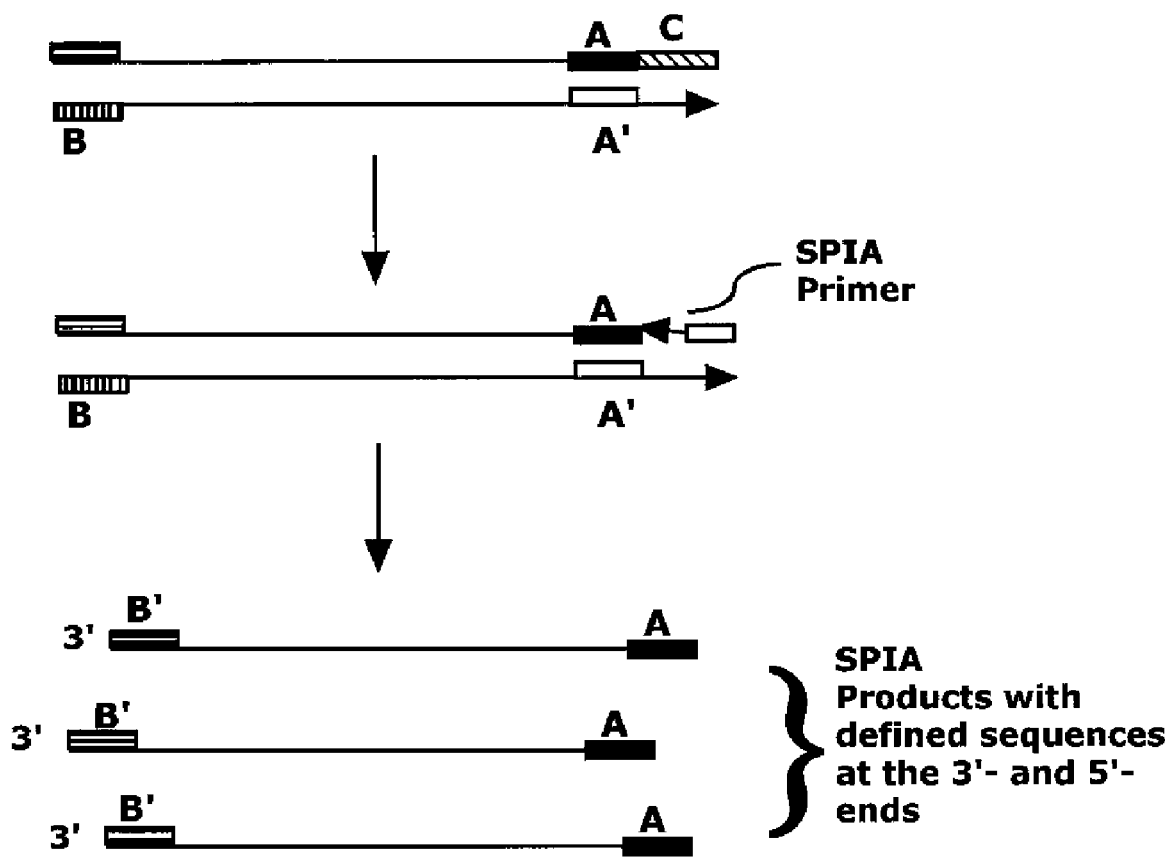
FIG. 18 illustrates a method of producing amplified DNA from the SPIA substrate of FIG. 17.

FIG. 18 depicts a method of amplifying a target sequence from the double stranded nucleic acid product of FIG. 17 by employing the double stranded nucleic acid product as a substrate for SPIA amplification. In the first step of FIG. 18, RNase H cleaves the RNA portion of the (C')—(C) DNA-RNA heteroduplex of the double stranded nucleic acid product, and a chimeric amplification primer as described previously is annealed to the DNA sequence (C'). In the next step, SPIA amplification products comprising a 3' end comprising sequence (B') and a 5'-end comprising sequence (A) are generated by providing RNase H, a chimeric amplification primer, and a strand displacing DNA polymerase.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

General Techniques

The practice of the invention may employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

The terms "Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3'-terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha.-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The oligonucleotide(s) are generally comprised of a sequence of at least 5 nucleotides, generally from about 10 to about 100 nucleotides, about 20 to about 50 nucleotides, and often about 10 to about 30 nucleotides in length. The oligonucleotides of the invention can be DNA, RNA, DNA-RNA, or other polynucleotide. The terms oligonucleotide or sequence may be used interchangeably herein.

Various techniques can be employed for preparing an oligonucleotide utilized in the present invention. Such oligonucleotide can be obtained by biological synthesis or by chemical synthesis. For short sequences (up to about 100 nucleotides) chemical synthesis may frequently be more economical as compared to the biological synthesis. In addition to economy, chemical synthesis provides a convenient way of incorporating low molecular weight compounds and/or modified bases during the synthesis step. Furthermore, chemical synthesis is very flexible in the choice of length and region of the target polynucleotide binding sequence. The oligonucleotide can be synthesized by standard methods such as those used in commercial automated nucleic acid synthesizers. Chemical synthesis of DNA on a suitably modified glass or resin can result in DNA covalently attached to the surface. This may offer advantages in washing and sample handling. For longer sequences standard replication methods employed in molecular biology can be used such as the use of M13 for single stranded DNA as described by J. Messing (1983) Methods Enzymol, 101, 20-78.

In the present invention, nucleoside triphosphates are incorporated by a polymerase enzyme in the extension of the primer to produce an extension product. Nucleoside triphosphates are generally nucleosides having a 5'-triphosphate substituent. The nucleosides are pentose sugar derivatives of nitrogenous bases of either purine or pyrimidine derivation, covalently bonded to the 1'-carbon of the pentose sugar, which is usually a deoxyribose or a ribose. The purine bases include adenine (A), guanine (G), inosine (I), and derivatives and analogs thereof. The pyrimidine bases include cytosine (C), thymine (T), uracil (U), and derivatives and analogs thereof. Nucleoside triphosphates include deoxyribonucleoside triphosphates such as the four common triphosphates dATP, dCTP, dGTP and dTTP and ribonucleoside triphosphates such as the four common triphosphates rATP, rCTP, rGTP and rUTP. The term "nucleoside triphosphates" also includes derivatives and analogs thereof, which are exemplified by those derivatives that are recognized in a similar manner to the underivatized nucleoside triphosphates. Examples of such derivatives or analogs, by way of illustration and not limitation, are those which are biotinylated, amine modified, alkylated, and the like and also include phosphorothioate, phosphite, ring atom modified derivatives, and the like.

As used herein, the term "nucleotide" generally refers to a base-sugar-phosphate combination that is the monomeric unit of nucleic acid polymers, i.e., DNA and RNA. In some aspects of the invention modified nucleotides are used, for example, where a nucleotide is connected to a ligand. A modified nucleotide is generally the unit in a nucleic acid polymer that results from the incorporation of a modified nucleoside triphosphate during an amplification reaction and therefore becomes part of the nucleic acid polymer.

As used herein, a "nucleoside" is generally a base-sugar combination or a nucleotide lacking a phosphate moiety.

The term "double stranded product" is used herein to refer to products that are produced by the extension of a primer. It is understood that the products are at least partially double stranded, for example, in the region comprising the primer extension product and its complement. The double stranded product need not be completely double-stranded, and may have single stranded regions. It is also understood that the double stranded product can have heteroduplex regions in which one strand comprises RNA and the complementary strand comprised DNA in that region.

Reaction Conditions and Detection

Appropriate reaction media and conditions for carrying out the methods of the invention include those that permit nucleic acid extension, copying, and amplification according to the methods of the invention. Such media and conditions are known to persons of skill in the art, and are described in various publications, such as U.S. Pat. Nos. 5,554,516; 5,716,785; 5,130,238; 5,194,370; 6,090,591; 5,409,818; 5,554,517; 5,169,766; 5,480,784; 5,399,491; 5,679,512; and PCT Pub. No. WO99/42618. For example, a buffer may be Tris buffer, although other buffers can also be used as long as the buffer components are non-inhibitory to enzyme components of the methods of the invention. The pH is preferably from about 5 to about 11, more preferably from about 6 to about 10, even more preferably from about 7 to about 9, and most preferably from about 7.5 to about 8.5. The reaction medium can also include bivalent metal ions such as $Mg.sup.2+$, or $Mn.sup.2+$, at a final concentration of free ions that is within the range of from about 0.01 to about 15 mM, and most preferably from about 1 to 10 mM. The reaction medium can also include other salts, such as KCl or NaCl, that contribute to the total ionic strength of the medium. For example, the range of a salt such as KCl is preferably from about 0 to about 125 mM, more preferably from about 0 to about 100 mM, and most preferably from about 0 to about 75 mM. The reaction medium can further include additives that could affect performance of the amplification reactions, but that are not integral to the activity of the enzyme components of the methods. Such additives include proteins such as BSA, single stranded binding protein (for example, T4 gene 32 protein), and non-ionic detergents such as NP40 or Triton. Reagents, such as DTT, that are capable of maintaining enzyme activities can also be included. Such reagents are known in the art. Where appropriate, an RNase inhibitor (such as Rnasin) that does not inhibit the activity of the RNase employed in the method can also be included. Any aspect of the methods of the invention can occur at the same or varying temperatures. In some embodiments, the amplification reactions (particularly, primer extension and transcription; and generally not the step of denaturing) are performed isothermally, which substantially avoids the thermocycling process. The isothermal amplification reaction is carried out at a temperature that permits hybridization of the oligonucleotides (primer) of the invention to the template polynucleotide and that does not substantially inhibit the activity of the enzymes employed. The temperature can be in the range of preferably about 25° C. to about 85° C., more preferably about 30° C. to about 80° C., and most preferably about 37° C. to about 75° C. The temperature for the transcription steps can be lower than the temperature(s) for the preceding steps. The temperature of the transcription steps can be in the range of preferably about 25° C. to about 85° C., more preferably about 30° C. to about 75° C., and most preferably about 37° C. to about 70° C.

Extension of Primers

The methods of the present invention involve the extension of primers. In general, primers hybridize to, and are extended along (chain extended), a sequence within the target polynucleotide and, thus, the target polynucleotide acts as a template. The extended primers are chain "extension products." The sequence over which the primer is extended may lie between two defined sequences but need not be. In general, the primers hybridize with a sequence within the target polynucleotide. The target sequence usually contains from about 10 to 30 to 50 to 100 or up to 5,000 or more nucleotides, often 10 to 1,000 nucleotides, or 10-10,000 nucleotides. The target polynucleotide may be a fraction of a larger molecule or it may be substantially the entire molecule (polynucleotide analyte).

Single Primer Isothermal Amplification Using a Complex Comprising an RNA/DNA Partial Heteroduplex as a Template In some aspects of the invention, the amplification method that is used is a single primer isothermal amplification using a complex comprising an RNA/DNA partial heteroduplex as a template. In this method, termed single primer isothermal amplification, a complex comprising an RNA/DNA partial heteroduplex is a substrate for further amplification as follows: an enzyme which cleaves RNA sequence from an RNA/DNA heteroduplex (such as RNase H) cleaves RNA from the partial heteroduplex, leaving a partially double stranded polynucleotide complex comprising a 3' single stranded DNA sequence. The 3' single stranded sequence (formed by cleavage of RNA in the complex comprising an RNA/DNA partial heteroduplex) is generally the complement of the amplification composite primer, and thus forms a specific binding site for a composite primer. Extension of a bound composite primer by a DNA-dependent DNA polymerase with strand displacement activity produces a primer extension product, which displaces the previously bound cleaved primer extension product, whereby polynucleotide (generally, DNA) product accumulates. See, for example, U.S. Pat. Nos. 6,251,639 and 6,692,918.

Amplification using a complex comprising an RNA/DNA partial heteroduplex as a template for further amplification (also termed single primer isothermal amplification) generally occurs under conditions permitting composite primer hybridization, primer extension by a DNA polymerase with strand displacement activity, cleavage of RNA from an RNA/DNA hybrid and strand displacement. In so far as the composite primer hybridizes to the 3'-single stranded portion (of the partially double stranded polynucleotide which is formed by cleaving RNA in the complex comprising an RNA/DNA partial heteroduplex) comprising, generally, the complement of at least a portion of the composite primer sequence, composite primer hybridization may be under conditions permitting specific hybridization.

In some embodiments, the methods of the invention result in amplification of a multiplicity, a large multiplicity, or a very large multiplicity of template polynucleotide sequences. In some embodiments, essentially all of the template polynucleotide present in the initial sample (e.g., all of the mRNA or all of the genomic DNA) is amplified. In other embodiments, at least 1, at least 2, at least 3, at least 4, at least 5, at least 10, at least 20, at least 50, at least 100, at least 200, at least 300, at least 500, at least 1,000, at least 5,000, at least 10,000 or more than 10,0000 distinct sequences (such as a gene or other sub-segment of a polynucleotide, transcripts of a nucleic acid target, a marker (such as a SNP or other polymorphism) are amplified, as assessed, e.g., by analysis of marker sequences known to be present in the template sample under analysis, using methods known in the art. Template polynucleotide sequences that are amplified may be present on the same polynucleotide (e.g., a chromosome or portion of a chromosome for genomic DNA template or on the same RNA for RNA template) or on different template polynucleotides (e.g., different chromosome or portions of chromosomes for DNA template, or different RNAs for RNA template). In some case, amplification of genomic DNA is exemplified herein, it will be understood by those of skill in the art, however, that the global amplification methods of the invention are suitable for amplification of any pool or subset of polynucleotides.

In some embodiments, the methods of the invention are used to globally amplify double stranded DNA target. It is understood that in these cases, the amplified product generally is a mixture of sense and antisense copies of the template DNA. In some embodiments, the methods of the invention are used to globally amplify a single stranded DNA or RNA target. In these cases, the amplification product may generally be a copy of either the target polynucleotide (sense copy) or of the complement to the target nucleotide (antisense copy). Whether the sense or antisense copy is produced will depend on the method, as will be understood by one of ordinary skill in the art. In some embodiments, the amplification product of different senses can be annealed to form a double stranded (or partially double stranded) complex. In other embodiments, they can be prevented from annealing (or subsequently denatured) to produce a mixture of single stranded amplification products. The amplified products may be of differing lengths.

As illustrated in these embodiments, all steps are isothermal (in the sense that thermal cycling is not required), although the temperatures for each of the steps may or may not be the same. It is understood that various other embodiments may be practiced, given the general description provided above. For example, as described and exemplified herein, certain steps may be performed as temperature is changed (e.g., raised, or lowered).

For simplicity, the isothermal amplification methods of the invention are described as two distinct steps or phases, above. It is understood that the two phases may occur simultaneously in some embodiments (for example, if the enzyme that cleaves RNA from RNA/DNA hybrid is included in the first reaction mixture).

Although generally only one composite primer is described above, it is further understood that the amplification methods may be performed in the presence of two or more different composite primers that randomly prime template polynucleotide. In addition, the amplification polynucleotide products of two or more separate amplification reactions conducted using two or more different composite primers that randomly prime template polynucleotide can be combined.

Other Amplification Methods

Some aspects of the invention comprise the amplification of polynucleotide molecules or sequences within the polynucleotide molecules. Amplification generally refers to a method that results in the formation of one or more copies of a nucleic acid or polynucleotide molecule or in the formation of one or more copies of the complement of a nucleic acid or polynucleotide molecule. Amplifications can be used in the invention, for example, to amplify or analyze a polynucleotide bound to a solid surface. The amplifications can be performed, for example, after archiving the samples in order to analyze the archived polynucleotide.

In some aspects of the invention, exponential amplification of nucleic acids or polynucleotides is used. These methods often depend on the product catalyzed formation of multiple copies of a nucleic acid or polynucleotide molecule or its complement. The amplification products are sometimes referred to as "amplicons." One such method for the enzymatic amplification of specific double stranded sequences of DNA is known as the polymerase chain reaction (PCR). This in vitro amplification procedure is based on repeated cycles of denaturation, oligonucleotide primer annealing, and primer extension by thermophilic template dependent polynucleotide polymerase, resulting in the exponential increase in copies of the desired sequence of the polynucleotide analyte flanked by the primers. The two different PCR primers, which anneal to opposite strands of the DNA, are positioned so that the polymerase catalyzed extension product of one primer can serve as a template strand for the other, leading to the accumulation of a discrete double stranded fragment whose length is defined by the distance between the 5' ends of the oligonucleotide primers.

Another method for amplification involves amplification of a single stranded polynucleotide using a single oligonucleotide primer. The single stranded polynucleotide that is to be amplified contains two non-contiguous sequences that are complementary to one another and, thus, are capable of hybridizing together to form a stem-loop structure. This single stranded polynucleotide already may be part of a polynucleotide analyte or may be created as the result of the presence of a polynucleotide analyte.

Another method for achieving the result of an amplification of nucleic acids is known as the ligase chain reaction (LCR).

This method uses a ligase enzyme to join pairs of preformed nucleic acid probes. The probes hybridize with each complementary strand of the nucleic acid analyte, if present, and ligase is employed to bind each pair of probes together resulting in two templates that can serve in the next cycle to reiterate the particular nucleic acid sequence.

Another method for achieving a nucleic acid amplification is the nucleic acid sequence based amplification (NASBA). This method is a promoter-directed, enzymatic process that induces in vitro continuous, homogeneous and isothermal amplification of a specific nucleic acid to provide RNA copies of the nucleic acid. The reagents for conducting NASBA include a first DNA primer with a 5'-tail comprising a promoter, a second DNA primer, reverse transcriptase, RNAse-H, T7 RNA polymerase, NTP's and dNTP's.

Another method for amplifying a specific group of nucleic acids is the Q-beta-replicase method, which relies on the ability of Q-beta-replicase to amplify its RNA substrate exponentially. The reagents for conducting such an amplification include "midi-variant RNA" (amplifiable hybridization probe), NTP's, and Q-beta-replicase.

Another method for amplifying nucleic acids is known as 3 SR and is similar to NASBA except that the RNAse-H activity is present in the reverse transcriptase. Amplification by 3 SR is an RNA specific target method whereby RNA is amplified in an isothermal process combining promoter directed RNA polymerase, reverse transcriptase and RNase H with target RNA. See for example Fahy et al. PCR Methods Appl. 1:25-33 (1991).

Another method for amplifying nucleic acids is the Transcription Mediated Amplification (TMA) used by Gen-Probe. The method is similar to NASBA in utilizing two enzymes in a self-sustained sequence replication. See U.S. Pat. No. 5,299,491 herein incorporated by reference.

Another method for amplification of nucleic acids is Strand Displacement Amplification (SDA) (Westin et al 2000, Nature Biotechnology, 18, 199-202; Walker et al 1992, Nucleic Acids Research, 20, 7, 1691-1696), which is an isothermal amplification technique based upon the ability of a restriction endonuclease such as HincII or BsoBI to nick the unmodified strand of a hemiphosphorothioate form of its recognition site, and the ability of an exonuclease deficient DNA polymerase such as Klenow exo minus polymerase, or Bst polymerase, to extend the 3'-end at the nick and displace the downstream DNA strand. Exponential amplification results from coupling sense and antisense reactions in which strands displaced from a sense reaction serve as targets for an antisense reaction and vice versa.

Another method for amplification of nucleic acids is Rolling Circle Amplification (RCA) (Lizardi et al. 1998, Nature Genetics, 19:225-232). RCA can be used to amplify single stranded molecules in the form of circles of nucleic acids. In its simplest form, RCA involves the hybridization of a single primer to a circular nucleic acid. Extension of the primer by a DNA polymerase with strand displacement activity results in the production of multiple copies of the circular nucleic acid concatenated into a single DNA strand.

In some embodiments of the invention, RCA is coupled with ligation. For example, a single oligonucleotide can be used both for ligation and as the circular template for RCA. This type of polynucleotide can be referred to as a "padlock probe" or a "RCA probe". For a padlock probe, both termini of the oligonucleotide contains sequences complementary to a domain within a nucleic acid sequence of interest. The first end of the padlock probe is substantially complementary to a first domain on the nucleic acid sequence of interest, and the second end of the padlock probe is substantially complementary to a second domain, adjacent to the first domain near the first domain. Hybridization of the oligonucleotide to the target nucleic acid results in the formation of a hybridization complex. Ligation of the ends of the padlock probe results in the formation of a modified hybridization complex containing a circular polynucleotide. In some cases, prior to ligation, a polymerase can fill in the gap by extending one end of the padlock probe. The circular polynucleotide thus formed can serve as a template for RCA that with the addition of a polymerase results in the formation of an amplified product nucleic acid. The methods of the invention described herein, can produce amplified products with defined sequences on both the 5'- and 3'-ends. Such amplified products can be used as padlock probes.

Some aspects of the invention utilize the linear amplification of nucleic acids or polynucleotides. Linear amplification generally refers to a method that involve the formation of one or more copies of the complement of only one strand of a nucleic acid or polynucleotide molecule, usually a nucleic acid or polynucleotide analyte. Thus, the primary difference between linear amplification and exponential amplification is that in the latter process, the product serves as substrate for the formation of more product, whereas in the former process the starting sequence is the substrate for the formation of product but the product of the reaction, i.e. the replication of the starting template, is not a substrate for generation of products. In linear amplification the amount of product formed increases as a linear function of time as opposed to exponential amplification where the amount of product formed is an exponential function of time.

In some embodiments, amplification methods can be solid-phase amplification, polony amplification, colony amplification, emulsion PCR, bead RCA, surface RCA, surface SDA, etc., as will be recognized by one of skill in the art. In some embodiments, amplification methods that results in amplification of free DNA molecules in solution or tethered to a suitable matrix by only one end of the DNA molecule can be used. Methods that rely on bridge PCR, where both PCR primers are attached to a surface (see, e.g., WO 2000/018957 and Adessi et al., Nucleic Acids Research (2000): 28(20): E87) can be used. In some cases the methods of the invention can create a "polymerase colony technology", or "polony", referring to a multiplex amplification that maintains spatial clustering of identical amplicons (see Harvard Molecular Technology Group and Lipper Center for Computational Genetics website). These include, for example, in situ polonies (Mitra and Church, Nucleic Acid Research 27, e34, Dec. 15, 1999), in situ rolling circle amplification (RCA) (Lizardi et al., Nature Genetics 19, 225, July 1998), bridge PCR (U.S. Pat. No. 5,641,658), picotiter PCR (Leamon et al., Electrophoresis 24, 3769, November 2003), and emulsion PCR (Dressman et al., PNAS 100, 8817, Jul. 22, 2003). The methods of the invention provide new methods for generating and using polonies.

Compositions
Primers and Oligonucleotides

The invention provides compositions, kits, complexes, reaction mixtures and systems comprising various components and their combinations used in the amplification methods described herein. In one aspect, for example, the invention provides compositions comprising an all DNA primer. All DNA or RNA-DNA chimeric primers may comprise a nucleotide sequence (i.e. a polynucleotide), generally with a free 3'-OH group, that hybridizes with a template sequence (such as a target RNA or DNA, or a primer extension product) and is capable of promoting polymerization of a polynucleotide complementary to the template. An all DNA primer or an RNA-DNA chimeric primer maybe, for example, an oligonucleotide. It can also be, for example, a sequence of the template (such as a primer extension product or a fragment of the template created following RNase cleavage of a template-DNA complex) that is hybridized to a sequence in the template itself (for example, as a hairpin loop), and that is capable of promoting nucleotide polymerization. Thus, a primer can be an exogenous (e.g., added) primer or an endogenous (e.g., template fragment) primer.

The primers of the invention are usually oligonucleotide primers. A primer is generally an oligonucleotide that is employed in an extension on a polynucleotide template. The oligonucleotide primer is usually a synthetic nucleotide that is single stranded, containing a sequence at its 3'-end that is capable of hybridizing with a sequence of the target polynucleotide. Normally, the 3'-region of the primer that hybridizes with the target nucleic acid has at least 80%, preferably 90%, more preferably 95%, most preferably 100%, complementarity to a sequence or primer binding site. The number of nucleotides in the hybridizable sequence of a specific oligonucleotide primer should be such that stringency conditions used to hybridize the oligonucleotide primer may prevent excessive random non-specific hybridization. Usually, the number of nucleotides in the hybridizing portion of the oligonucleotide primer may be at least as great as the defined sequence of the target polynucleotide, namely, at least five nucleotides, at least about ten nucleotides, at least about 15 nucleotides, generally from about 5 to about 200, and usually about 10 to about 50 nucleotides.

A "random primer," or "random annealing sequence" as used herein, is a primer that comprises a sequence that is designed not necessarily based on a particular or specific sequence in a sample, but rather is based on a statistical expectation (or an empirical observation) that the sequence of the random primer is hybridizable (under a given set of conditions) to one or more sequences in the sample. The random primers used herein are generally tailed random primers comprising a 3'-segment that acts as a random primer to the target polynucleotide, and a 5'-sequence that generally does not hybridize to the target polynucleotide. The sequence of any one primer molecule from a sample of random primers (or their complement) may or may not be naturally-occurring, and may or may not be present in the sequences in a sample of interest. The amplification of a plurality of polynucleotides, e.g. DNA or RNA species in a single reaction mixture would generally, but not necessarily, employ a multiplicity, preferably a large multiplicity, of random primers. As is well understood in the art, a "random primer" can also refer to a primer that is a member of a population of primers (a plurality of random primers) which collectively are designed to hybridize to a desired and/or a significant number of target sequences. A random primer may hybridize at a plurality of sites on a nucleic acid sequence. The use of random primers provides a method for generating primer extension products complementary to a target polynucleotide which does not require prior knowledge of the exact sequence of the target. In some embodiments one portion of a primer is random, and another portion of the primer comprises a defined sequence. For example, in some embodiments, a 3'-portion of the primer may comprise a random sequence, while the 5'-portion of the primer comprises a defined sequence. In other embodiments, for example, a 3'-portion of the primer may comprise a defined sequence, while the 5' portion of the primer comprises a random sequence. In some embodiments a 3'-random portion of the primer may comprise DNA, and a 5'-portion defined portion of the primer may comprise RNA, in other embodiments, both the 3'- and 5'-portions may comprise DNA.

All DNA primers generally comprise polynucleotide annealing sequences. The length of the annealing sequence can be for example from about 2 to about 100 nucleotides. In some cases, the all DNA primers comprise polynucleotide annealing sequences of length about 3 nucleotides to about 50 nucleotides. In other cases, the all DNA primers comprise short polynucleotide annealing sequences of about 4 nucleotides to about 20 nucleotides in length. In still other embodiments, the all DNA primers comprise polynucleotide annealing sequences of about 4 to about 10 or 15 nucleotides in length. In some embodiments, the all DNA primer annealing sequence is about 8 nucleotides. In other embodiments, the all DNA primer annealing sequence is about 6 nucleotides. In some cases the primer may consist of only the annealing sequence, whereas in other cases the primer may also comprise other portions which are not annealing sequences such as a tail sequence or an element other than the annealing sequence and the tail sequence such as a linker for example. In other cases, the all DNA primers also comprise a ligand. The ligand may or may not be comprised of nucleic acid. In some cases, the ligand is a small organic molecule such as for example biotin or a fluorophore. The primers may be synthesized by a number of common methods known in the art. In some cases, the methods of synthesizing primers of the present invention include solid phase synthesis methods such as provided in U.S. Pat. No. 5,623,068.

Precise nucleotide lengths and compositions can be determined by one with ordinary skill in the art for designing DNA primers for hybridization to an RNA or DNA template nucleic acid and extension by a polymerase. The nucleotide length and sequence composition may take into account the temperature of the hybridization and polymerization reactions to be performed, the propensity for secondary structure inherent in the all DNA primer or the nucleic acid template, the likelihood of a given all DNA primer to hybridize to non-specific or closely related sequences, and the sequence of the nucleic acid template. Suitable primer lengths include from about 5 to about 200 or more nucleotides including about 5, 6, 7, 8, 9, 10, 12, 15, 20, 25, 30, 35, 40, 45, 50, 55, 60, 70, 80, 90, or about 100 or more nucleotides in length.

The nucleotide length and sequence composition may be designed to provide specific hybridization to a desired sequence, specific hybridization to a family of related sequences, or hybridization to any sequence or substantially any sequence of a genome or transcriptome. In the case of designing a primer that anneals to any sequence, randomized sequences may be used such as for example random heptamers, hexamers, septamers, octamers, nonamers, or random decamers. In some cases, non-standard bases which exhibit base pairing interactions with more than one partner such as inosine which can base pair with uracil, adenine, and cytosine may be used. The non-standard bases with greater propensity for multiple base pairing partners are referred to as wobble bases. In other cases, specific annealing sequences may be used in combination with such wobble bases. In some cases, all DNA primers comprise specific annealing sequences in which one or more positions within the annealing sequence are randomized. Such a combination of specific sequences with randomized positions may be used for example to amplify a set of related or homologous nucleic acid sequences. In still other cases, all DNA primers comprise specific annealing sequences, or a set of specific sequences. In an exemplary embodiment, the annealing sequence comprises a poly thymine sequence such that messenger RNA molecules are preferentially amplified.

In some cases, all DNA primers may comprise modification of bases or the introduction of nonstandard bases in addition to or other than the inosine base previously described. Non standard bases may be used to increase the thermal stability of the hybridized primer to its target nucleic acid, to increase specificity, or to increase stability (i.e. resistance to degradation). Non standard bases may include but are not limited to locked nucleic acids, peptide nucleic acids, pyranosyl nucleic acids, methylated nucleic acids, or any other modified or nonstandard nucleic acid known to the art. In some cases, the first primer, second primer, composite primer, or chimeric primer comprises non-standard bases which can be recognized by a polymerase such as for example a DNA-dependent DNA polymerase or an RNA-dependent DNA polymerase and copied in a consistent and efficient manner. In some cases, an amplification primer, composite amplification primer, or chimeric amplification primer may comprise any variety of nonstandard bases as described herein.

All DNA primers may also comprise a tail sequence. The tail sequence may provide a useful way for further manipulation of amplified products such as purification, functionalization, capture, immobilization or other downstream processes such as sequence determination or further amplification, the tag may also be integral to the amplification process itself such as but not limited to the process described in FIGS. 3 and 8. The tail sequence may comprise a sequence that does not hybridize or does not substantially hybridize to the target nucleic acid under the conditions of the method. In some cases, the tail sequence may be designed such that it does not hybridize or substantially hybridize to other primers, oligonucleotides, or tail sequences employed in the method such as sequence (B) of FIG. 4 or sequence (C) of FIG. 10. In other cases, the tail sequence may be designed such that it does hybridize to other primers, oligonucleotides, or tail sequences employed in the method. The tail sequence may comprise a sequence between about 1 or 2 nucleotides in length to about 200 nucleotides in length including about 3, 4, 5, 8, 10, 15, 20, 25, 30, 50, 75, 100, 150, or 200 nucleotides in length.

In some embodiments, all DNA primers comprising a 3'-template annealing sequence and a 5'-sequence tail (A) are used in a first primer extension reaction. The all DNA first primer may be annealed to the target nucleic acid subsequent to an elevated temperature denaturing step to remove secondary structure and or separate complementary strands. Annealing of the all DNA first primer may be followed by addition of polymerase and nucleotide triphosphates as well as buffers, cations, anions, and solute modifying reagents such as glycerol, polyethylene glycol, bovine serum albumin, dimethyl sulfoxide, or single-stranded binding proteins, and the like to initiate a first primer extension reaction. In some cases, a strand displacing polymerase may be used, while in other cases it may be advantageous to utilize a polymerase that does not exhibit substantial strand displacing activity. The first primer extension reaction may provide a template for further manipulation including but not limited to annealing of a chimeric DNA-RNA second primer.

In some aspects of the present invention, chimeric primers (also referred to as composite primers) are utilized. Chimeric primers can be for example a second primer in the methods of the invention, chimeric extension primers or chimeric amplification primers. Chimeric primers of the present invention include primers that comprise an RNA segment and a DNA segment. The RNA segment may be generally located at the 5' end of the chimeric primer and the DNA segment may generally be located at the 3' end of the chimeric primer. In some cases the RNA and DNA segments are adjacent. In other cases, there is an intervening element between the RNA and the DNA segment. The intervening element may comprise additional nucleic acid sequence. In one embodiment, a portion of the DNA segment comprises a template annealing sequence. The template annealing sequence as described for the all DNA primer may be target specific, a set of target specific sequences, or a random sequence.

In some embodiments of the present invention, the DNA-RNA chimeric primer annealing sequences may be between about 2 nucleotides in length to about 100 nucleotides in length. In some cases, annealing sequences may be between about 3 nucleotides in length to about 50 nucleotides in length. In still other cases, annealing sequences may be about 4 to about 30 nucleotides in length. For example, but without limitation, DNA-RNA chimeric primer annealing sequences may be about 5, 6, 7, 8, 9, 10, 12, 14, 16, 18, 20, or 25 nucleotides in length. In some cases, random annealing sequences comprise random pentamers, hexamers, heptamers, octomers, decamers, or larger.

In some cases, for example with the use of random template annealing sequences, it may be advantageous to extend the chimeric primer with a polymerase that does not exhibit substantial strand displacement activity. In other cases, it may be advantageous to extend the chimeric primer with a polymerase that does exhibit substantial strand displacement activity. In some cases, the use of a polymerase that exhibits substantial strand displacement activity may be useful for whole genome and or whole transcriptome amplification.

In some embodiments of the present invention, a portion of the RNA segment of the chimeric primer comprises a sequence tail. The sequence tail may in some cases comprise the same sequence (A) as the sequence tail used for an all DNA first primer extension reaction. In other cases, the sequence tail may comprise a different sequence (B) as compared to the sequence tail used for an all DNA first primer extension reaction.

In some embodiments of the present invention, a chimeric primer comprising a 5'-RNA segment comprising a sequence tail and a 3' DNA segment comprising a template annealing sequence is annealed to a first primer extension product, a polymerase and is added to the annealing reaction, and a second primer extension product is created. In some embodiments of the present invention, a 3'-exonuclease is added after the second primer extension reaction is completed. The 3'-exonuclease may remove the 3'-unhybridized portion of the first primer extension product. Removal of the exonuclease by heat, the addition of inhibitors, or nucleic acid purification methods may allow further extension of the first primer extension product. The further extension may provide sequence complementary to the sequence tail of the chimeric primer.

Amplification primers of the present invention include chimeric or composite amplification primers. Composite amplification primers are RNA/DNA composite primers that can be used to create multiple copies of (amplify) a polynucleotide sequence isothermally using RNA cleavage, and DNA polymerase activity with strand displacement. Amplification with such primers is described, for example in U.S. Pat. Nos. 6,251,639, 6,692,918, and 6,946,251. The composite amplification primer comprises sequences capable of hybridizing to a portion of a DNA template, and most often comprises sequences hybridizable to a defined 3'-portion of the DNA.

A composite amplification primer comprises at least one RNA portion that is capable of (a) binding (hybridizing) to a sequence on a DNA template independent of hybridization of the DNA portion(s) to a sequence on the same extension product; and being cleaved with an RNase H when hybridized to the DNA template. The composite amplification primers bind to the DNA template to form a partial heteroduplex in which only the RNA portion of the primer is cleaved upon contact with a ribonuclease such as RNase H, while the DNA template remains intact, thus enabling annealing of another composite primer.

The composite amplification primers also comprise a 3'-DNA portion that is capable of hybridization to a sequence on the DNA template such that its hybridization to the DNA is favored over that of the nucleic acid strand that is displaced from the DNA template by the DNA polymerase. Such primers can be rationally designed based on well known factors that influence nucleic acid binding affinity, such as sequence length and/or identity, as well as hybridization conditions. In some aspects of the present invention, the 3' DNA portion of a composite amplification primer may be about 4, 5, 6, 7, 8, 9, 10, 11, 12, 13, or 14 nucleotides in length.

In some embodiments of the present invention chimeric oligonucleotides are utilized. In some cases, the chimeric oligonucleotides may be used to provide a defined end sequence for the SPIA amplified DNA products. The chimeric oligonucleotides may comprise a 5' segment comprising RNA and a 3' segment comprising DNA. In some embodiments such as for example those depicted in FIGS. 10 and 12, a portion of the 3' segment of the chimeric oligonucleotide is substantially the same as the RNA sequence removed from the DNA-RNA heteroduplex of a SPIA substrate by RNase H. In other cases, such as for example that depicted in FIG. 16, a portion of the 3' segment of the chimeric oligonucleotide is substantially the same as the complement of the tail sequence of the first primer.

Enzymes

Polymerases are used in the methods of the invention, for example to extend primers to produce primer extension products. A polymerase, or nucleotide polymerase, is a catalyst, usually an enzyme, for forming an extension of a polynucleotide along a DNA or RNA template where the extension is complementary thereto. The nucleotide polymerase is a template dependent polynucleotide polymerase and utilizes nucleoside triphosphates as building blocks for extending the 3'-end of a polynucleotide to provide a sequence complementary with the polynucleotide template. Usually, the catalysts are enzymes, such as DNA polymerases, for example, prokaryotic DNA polymerase (I, II, or III), T4 DNA polymerase, T7 DNA polymerase, Klenow fragment, Bst DNA polymerase, reverse transcriptase, Vent DNA polymerase, Pfu DNA polymerase, Taq DNA polymerase, and the like, derived from any source such as cells, bacteria, such as *E. coli*, plants, animals, virus, thermophilic bacteria, and so forth. RNA polymerases include T7 RNA polymerase, AMV polymerase, Q-beta-replicase, and so forth. In some cases, Bst DNA Polymerase Large Fragment can be used. Bst DNA polymerase Large Fragment is the portion of the *Bacillus stearothermophilus* DNA Polymerase protein that contains the 5'→3' polymerase activity, but lacks the 5'→3' exonuclease domain. Where the polymerase forms an extension product on a DNA template, it is referred to herein as a DNA dependent polymerase. Where the polymerase forms an extension product on a RNA template, it is referred to herein as a RNA dependent polymerase.

In some embodiments, the methods of the present invention provide enzyme inhibitors. In some cases, polymerase inhibitors are provided such as for example DNA-dependent DNA polymerase inhibitors. In some cases, DNA-dependent DNA polymerase inhibitors such as actinomycin that do not substantially inhibit RNA-dependent DNA polymerization are provided. Actinomycin may be particularly useful in the methods of the present invention when the target sequence to be amplified comprises RNA that is present in a sample that also comprises DNA. In such cases actinomycin may be used to selectively inhibit the production of extension product complementary to the DNA during, for example extension of the first primer.

Exonucleases are used in the methods of the invention, for example an exonuclease specific for single-stranded DNA, whereby treatment of the double stranded first and second primer extension products with the single-strand specific exonuclease enable the removal of the single stranded 3' nucleotides from the 3' region of a first primer extension product that are not hybridized to a second primer extension product. In another example an exonuclease may be used to remove unincorporated primers or target nucleic acids that are not hybridized to first or second primer extension products. In yet another example the treatment of the stem loop product of the second primer extension product generated using an all DNA tailed first primer and a chimeric second primer both comprising a sequence A at their 5'-ends, with a single strand specific 3'-exonuclease is used for clean-up of the reaction mixture as described previously, by the selective degradation of the non incorporated primers and other reaction products. Non-limiting examples of an exonuclease include single-strand specific 3'-exonucleases such as exonuclease 1. The exonuclease should remove all of the single-stranded 3' nucleotides which are not hybridized to form a double stranded nucleic acid. In some embodiments, the exonuclease may remove additional 3' nucleotides which are hybridized to a primer extension product. In other embodiments, a polymerase comprising exonuclease activity may be used. Non-limiting examples include a T4 polymerase comprising 3' exonuclease activity. Exonucleases may be used in the methods of the present invention for clean up of reaction mixtures, such as amplification reaction mixtures, for example single strand specific DNA exonucleases may be used for clean-up of PCR or SPIA amplification products without the need for purification prior to performing sequencing reactions.

RNases are used in the methods of the present invention, for example in some cases a single and or double stranded RNA specific RNase is used to degrade single and double stranded RNA from template nucleic acid and or unincorporated primers. In some cases, single and double stranded RNA specific RNases includes but is not limited to RNase 1. In another example RNase which is specific for the cleavage of the RNA portion of a DNA-RNA heteroduplex is used in the methods of the present invention to degrade or cleave the RNA portion of the DNA-RNA heteroduplex of a partial heteroduplex generated by the methods of the invention. This may have the effect of making the DNA portion of the DNA-RNA heteroduplex available to hybridize with other oligonucleotides such as but not limited to primers, amplification primers and chimeric oligonucleotides. By way of example and without limitation an example of a RNase specific for cleaving the RNA portion of a DNA-RNA heteroduplex is RNase H.

Nucleic Acid Target

A nucleic acid target, also referred to as a template, as defined herein includes but is not limited to any length nucleotide, for example, DNA and or RNA. Examples of nucleic acid templates include but are not limited to complementary cDNA, mRNA, total RNA, genomic DNA, and DNA. In some cases, the nucleic acid target may be derived from a natural source such as for example an organism or from the environment. In other cases, the nucleic acid target may be derived from a synthetic source such as a nucleic acid synthesizer. In still other cases, the nucleic acid target may comprise both natural and synthetic nucleic acids in any proportion. In some embodiments of the present invention, target nucleic acid may be purified prior to use by the methods of the present invention. In some cases, target nucleic acid may be pre-fractionated according to size and or sequence by electrophoresis, ion exchange, gel filtration, reverse phase, or hybridization techniques. In some cases, target nucleic acid may be amplified by other methods known to the art as described herein prior to application of the methods of the present invention. Sources for target nucleic acid include but are not limited to animals including but not limited to humans, non-human primates, dogs, cats, cows, pigs, sheep, guinea pigs, hamsters, birds, frogs, fish, rats, mice, rodents and any other animal from which nucleic acid may be obtained. Other sources for target nucleic acid include but are not limited to bacteria, viruses, plants, insects, worms, fruit flies, and fungi. Target nucleic acid may be obtained from tissue or bodily fluids such as skin, blood, cells, hair follicles, sebaceous glands, cells obtained from fine needle aspiration or other surgical and non surgical biopsy techniques, saliva, urine, stool, menses and the like, or may be obtained from cultures, environmental samples and the like.

Surface or Solid Substrate

In various exemplary embodiments, a solid surface may have a wide variety of forms, including membranes, slides, plates, micromachined chips, microparticles, beads and the like. Solid surfaces may comprise a wide variety of compositions including, but not limited to, glass, plastic, silicon, alkanethiolate derivatized gold, cellulose, low cross linked and high cross linked polystyrene, silica gel, polyamide, and the like, and can have various shapes and features (e.g., wells, indentations, channels, etc.). As used herein, the terms "solid surface" and "solid substrate" are used interchangeably. In some cases these may be referred to as the surface or the support. The surface can be hydrophilic or capable of being rendered hydrophilic and may comprise inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly(vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed. The surface can have any one of a number of shapes, such as strip, rod, particle, including bead, and the like.

In some embodiments, the solid surface comprises a bead or plurality of beads. The beads may be of any convenient size and fabricated from any number of known materials. Example of such materials include: inorganics, natural polymers, and synthetic polymers. Specific examples of these materials include: cellulose, cellulose derivatives, acrylic resins, glass, silica gels, polystyrene, gelatin, polyvinyl pyrrolidone, co- polymers of vinyl and acrylamide, polystyrene cross-linked with divinylbenzene or the like (as described, e.g, in Merrifield, Biochemistry 1964, 3, 1385-1390), polyacrylamides, latex gels, polystyrene, dextran, rubber, silicon, plastics, nitrocellulose, natural sponges, silica gels, control pore glass, metals, cross-linked dextrans (e.g., Sephadex) agarose gel (Sepharose™), polystyrene and other solid phase supports known to those of skill in the art. The beads are generally about 2 to about 100 um in diameter, or about 5 to about 80 pm in diameter, in some cases, about 10 to about 40, um in diameter. In some embodiments the beads can be magnetic. Having magnetic beads can be useful for isolation and purification of the beads comprising nucleic acids described herein. Other methods to separate beads can also be used. For example, the capture beads may be labeled with a fluorescent moiety which would make the nucleic acid-bead complex fluorescent. The target capture bead complex may be separated, for example, by flow cytometry or fluorescence cell sorter.

Attachment of Oligonucleotides to Solid Surfaces

One aspect of the invention involves attaching oligonucleotides to solid surfaces such that the oligonucleotides can hybridize with polynucleotides produced by the methods of the invention. Many methods of attaching oligonucleotides to surfaces are known. In some embodiments, the oligonucleotide is attached covalently to the solid surface. In some embodiments such attached oligonucleotides act to capture nucleic acids such as amplification products, and in some cases such attached oligonucleotides also act as primers. Methods of attaching oligonucleotides and primers to a surface are known in the art (see, e.g., Beier et al., 1999, Nucleic Acids Res. 27(9):1970-1977; Brison et al., 1982, Molecular and Cellular Biology 2:578 587; Cheung et al., 1999, Nat. Genet. 21(1 Suppl):15-19; Chrisey et al., 1996, Nucleic Acids Res. 24(15):3031-3039; Cohen et. al., 1997, Nucleic Acids Res. 1997 Feb. 15; 25(4):911-912; Devivar et al., 1999, Bioorg. Med. Chem. Lett. 9(9):1239-1242; Heme et al., 1997. J. Am. Chem. Soc. 119:8916-8920; Kumar et al., 2000, Nucleic Acis Res. 28(14):e71; Lipshutz et al., 1999, Nat. Genet. 21(1 Suppl):20-24; Milner et al., 1997, Nat. Biotechnol. June; 15(6):537-541; Morozov et al., 1999, Anal. Chem. 71(15):3110-3117; Proudnikov et al., 1998, Anal Biochem. 259(1):34-41; Rasmussen et al., 1991, Anal Biochem. 198(1): 138-142; Rogers et al., 1999, Anal. Biochem. 266(1):23-30; Salo et al., 1999, Bioconjug Chem. 10(5):815-823; Singh-Gasson et al., 1999, Nat. Biotechnol. 17(10):974-978, and Pierce Chemical Company Catalog 1994, pp. 155-200), incorporated herein by reference). Attached oligonucleotides may also be synthesized directly on the solid surface.

Uses of the Present Invention

Multiplex Amplification of Desired Nucleic Acid Targets from a Complex Sample

The methods of the present invention are useful for amplification of multiple different nucleic acid targets from a complex sample. The amplification of multiple different nucleic acid targets from a sample may be referred to as multiplex amplification. In some embodiments, multiplex amplification may be carried out by the methods of the present invention by the use of a set of first primers with different annealing sequences each of which is specific for a different nucleic acid target. In some cases, the template may be removed or degraded after the first primer extension product has been formed by the methods of the present invention. The multiple first primer extension products may then be contacted with a second primer with a random, degenerate, or specific annealing sequence. In other embodiments, the annealing sequence of the first primer may be random or degenerate, while a set of second primers may be used with different annealing sequences each of which is specific for a different nucleic acid target. Multiplex amplified products of the present invention may be detected by sequencing, nucleic acid array hybridization, electrophoresis, capture on solid phase (e.g. beads), or chromatography.

In a particular embodiment, multiplex amplification of a set of targets in a nucleic acid sample may be carried out to reduce the complexity in that sample. For example, the nucleic acid sample may be a whole genome or whole transcriptome. In some embodiments of the present invention it may be desirable to amplify only a set of the sequences in the whole genome or whole transcriptome such a set may include for example, the exons in a genome, the set of kinases, the set of protein kinases, the set of lipid kinases, proteases, serine proteases, cysteine proteases, oncogenes, transcription factors, polymorphic regions related to a particular disease or condition such as single nucleotide polymorphisms, or any set or subset of target sequences within a sample. In some cases, multiplex amplification may be used to amplify 5 or more sequences from a complex sample, 10 or more sequences, 25 or more, 50 or more, 100 or more sequences, 200 or more sequences, 300 or more sequences, 500 or more sequences, 1000 or more sequences, 2000 or more sequences, 5000 or more sequences, 10,000 or more sequences, 25,000 or more sequences, 50,000 or more sequences, or 100,000 or more sequences. In some cases, the methods of the present invention provide for improved multiplex amplification of target sequences as compared to other methods known in the art such as for example PCR because the linear amplification methods provided herein do not substantially alter the relative abundance of different sequences in a sample by preferentially amplifying some sequences over others. In some cases, the methods of the present invention are useful for processing nucleic acid samples by reducing their complexity by amplifying sequences of interest and/or removing sequences that are not of interest and preparing a sample for downstream processing such as sequencing, quantifying, and array hybridization.

Capture and Amplification of Single or Multiple Nucleic Acid Target or Targets from a Sample The methods of the present invention may be used for capture and amplification of single or multiple nucleic acid targets from a sample. In some embodiments, the first primer of the present invention may be attached to a solid phase such as a bead for example and used to capture a nucleic acid target from a sample such as a complex sample by hybridization. In some cases, un-captured nucleic acid may then be removed by washing way the nucleic acid not bound to the solid phase or by removing the solid phase from the nucleic acid that is not bound to the bead, or by a combination thereof. Methods and compositions for hybridization of specific sequences are provided herein. In some embodiments, the first primer and the target nucleic acid may hybridize in solution and the resulting hybridized product may then be captured. In some cases, the capture step may include the use of a solid phase that hybridizes to or has an affinity for a ligand that is bound to, or covalently bound to, the first primer. For example, the first primer may include a tail sequence that is complementary to a sequence bound to a bead. For another example, the first primer may include a ligand such as biotin that may bind to a solid phase (e.g. a bead) derivatized with streptavidin. In still another example, the first primer may include a streptavidin molecule and the solid phase may comprise biotin. In some embodiments the first primer has a specific annealing sequence for capture and amplification of a specific target nucleic acid. In other cases, the first primer may provide a degenerate annealing sequence for capture and amplification of multiple target nucleic acids. In some cases, the first primer may be provided as a set of first primers each with a different specific annealing sequence for capture and amplification of multiple target nucleic acids.

The captured target nucleic acid may be amplified by the methods provided herein. In some embodiments, a first primer extension product may be formed from the first primer bound to a captured target nucleic acid using the methods of the present invention by the use of a polymerase. The first primer extension product may be contacted with a second primer and a second primer extension product may be formed using the methods of the present invention. The second primer extension product may then be amplified using an amplification primer of the present invention, a polymerase, and RNAse H as described herein. The resulting amplification product may be useful for simplifying complex nucleic acid samples, (i.e. complexity reduction) by capturing and amplifying a subset of the nucleic acid that is desired for further analysis such as sequencing, array based genome or transcriptome analysis, expression profiling and analysis, genetic analysis, SNP analysis etc.

Characterization of Nucleic Acids

The methods of the invention are amenable to quantitative analysis, as in some embodiments, amplification can yield sufficient single stranded polynucleotide (generally, DNA and RNA) products which accurately reflect the representation of the various DNA or RNA sequences (e.g. genomic DNA or mRNA) in the starting material. The amplified products can be analyzed using, for example, probe hybridization techniques known in the art, such as Northern blotting, and hybridizing to probe arrays. In addition, the single stranded polynucleotide products may serve as starting material for other starting material for other analytical and/or quantification methods known in the art, such as real time PCR, quantitative TaqMan, quantitative PCR using molecular beacons, methods described in Kurn, U.S. Pat. No. 6,251,639, etc. Thus, the invention includes those further analytical and/or quantification methods as applied to any of the products of the methods herein.

In another embodiment, the amplification methods of the invention are utilized to generate multiple copies of single stranded polynucleotide products from RNA or DNA targets that are labeled by the incorporation of labeled nucleotides during DNA polymerization. For example, amplification according to the methods of the invention can be carried out with suitable labeled dNTPs or rNTPs. These labeled nucleotides can be directly attached to a label, or can comprise a moiety which could be attached to a label. The label may be attached covalently or non-covalently to the amplification products. Suitable labels are known in the art, and include, for example, a ligand which is a member of a specific binding pair which can be detected/quantified using a detectable second member of the binding pair. Thus, amplification of total RNA or mRNA according to the methods of the invention in the presence of, for example, Cy3-dUTP or Cy5-dUTP results in the incorporation of these nucleotides into the amplification products. Labeling can also be accomplished by random priming of amplification products with the incorporation of labeled dNTPs. Other methods for labeling and or fragmenting of the amplification products of the invention are known in the art, for example the methods provided by U.S. patent application Ser. Nos. 10/304,035 filed Nov. 22, 2002, and 10/441,663 filed May 19, 2003 which are herby incorporated by reference in their entirety and which are useful for the generation of products suitable for analysis using various designs of microarrays, such as for example high density oligonucleotides microarrays.

The labeled amplified products are suitable for analysis (for example, detection and/or quantification) by contacting them with, for example, microarrays (of any suitable surface, which includes glass, chips, plastic), beads, or particles, that comprise suitable probes such as cDNA and/or oligonucleotide probes. Thus, the invention provides methods to characterize (for example, detect and/or quantify) a DNA or RNA sequence of interest by generating labeled polynucleotide (generally, DNA) products using amplification methods of the invention, and analyzing the labeled products. Analysis of labeled products can be performed by, for example, hybridization of the labeled amplification products to, for example, probes immobilized at, for example, specific locations on a solid or semi-solid substrate, probes immobilized on defined particles, or probes immobilized on blots (such as a membrane), for example arrays. Other methods of analyzing labeled products are known in the art, such as, for example, by contacting them with a solution comprising probes, followed by extraction of complexes comprising the labeled amplification products and probes from solution. The identity of the probes provides characterization of the sequence identity of the amplified products, and thus by extrapolation the identity of the target DNA or target RNA present in a sample. Hybridization of the labeled products is detectable, and the amount of specific labels that are detected is proportional to the amount of the labeled amplification products of a specific DNA or RNA sequence of interest. This measurement is useful for, for example, measuring the relative amounts of the various RNA species in a sample, which are related to the relative levels of gene expression, as described herein or to detect the presence or absence of defined target DNA or RNA in a sample. The measurement is also useful for measuring the relative amounts of various DNA sequences corresponding, for example, to genetic regions in the sample. The amount of labeled products (as indicated by, for example, detectable signal associated with the label) hybridized at defined locations on an array can be indicative of the detection and/or quantification of the corresponding target DNA or target RNA species in the sample.

Sequencing of the Polynucleotide Products of the Invention

As described above, the methods can be used to obtain sequence information about a target RNA or target DNA of interest. The sequencing can be carried out on the primer extension products or amplification products produced by the methods herein. In some embodiments the sequencing is performed on the polynucleotides attached to solid surfaces as described herein. In one embodiment sequencing is performed on polynucleotides that are attached to the beads through oligonucleotides attached to the beads which capture amplified product, and are extended to produce a polynucleotide attached to the surface comprising a defined sequence at its 3' end.

The methods of the invention are useful, for example, for sequencing of a polynucleotide sequence of interest. The sequencing process may be carried out as described for the methods described herein. In some cases, the methods of the invention are useful for providing amplified products having defined 3' and 5' ends that are useful for further analysis such as for example for sequencing, array hybridization, or quantitative PCR. In some cases, the methods provide for multiplex amplification such as from complex mixtures such as whole genome or whole transcriptome or a portion thereof, or multiple whole genomes or whole transcriptomes or portions thereof.

Known methods for sequencing include, for example, those described in: Sanger, F. et al., Proc. Natl. Acad. Sci. U.S.A. 75, 5463-5467 (1977); Maxam, A. M. & Gilbert, W. Proc Natl Acad Sci USA 74, 560-564 (1977); Ronaghi, M. et al., Science 281, 363,365 (1998); Lysov, I. et al., Dokl Akad Nauk SSSR 303, 1508-1511 (1988); Bains W. & Smith G. C. J. Theor Biol 135, 303-307 (1988); Dmanac, R. et al., Genomics 4, 114-128 (1989); Khrapko, K. R. et al., FEBS Lett 256.118-122 (1989); Pevzner P. A. J Biomol Struct Dyn 7, 63-73 (1989); and Southern, E. M. et al., Genomics 13, 1008-1017 (1992). Pyrophosphate-based sequencing reaction as described, e.g., in U.S. Pat. Nos. 6,274,320; 6,258,568 and 6,210,891), may also be used.

In some cases, the methods and compositions of the present invention may be useful for capture and amplification of a plurality of target sequences from a complex sample, such as for example a whole genome or genomes, or a whole transcriptome or transcriptomes. The capture and amplification of target sequences from a complex sample may be desirable for complexity reduction. For example, complexity reduction may be advantageous for further use of the amplified products in highly parallel analytical techniques such as the use of high density microarrays, or high throughput sequencing methods including for example the use of the methods and instrumentation developed by Roche 454 Life Sciences, Illumina, Sequenom, ABI, or any of the sequencing methods described herein such as those described in U.S. Pat. Nos. 7,211,390; 6,355,431; 5,750,341; 5,969,119; 6,274,320; 6,258,568; 6,210,891; and 6,306,597. In some embodiments, this complexity reduction may be used to capture and in some cases amplify a single RNA or DNA sequence of interest from a complex sample.

The methods of the invention are useful, for example, for sequencing of an RNA sequence of interest. The sequencing process can be carried out by processing and amplifying a target RNA containing the sequence of interest by any of the methods described herein. Addition of nucleotides during primer extension can be analyzed using methods known in the art, for example, incorporation of a terminator nucleotide or sequencing by synthesis (e.g. pyrosequencing).

In embodiments wherein the end product is in the form of DNA primer extension products, in addition to the nucleotides, such as natural deoxyribonucleotide triphosphates (dNTPs), that are used in the amplification methods, appropriate nucleotide triphosphate analogs, which may be labeled or unlabeled, that upon incorporation into a primer extension product effect termination of primer extension, may be added to the reaction mixture. Preferably, the dNTP analogs are added after a sufficient amount of reaction time has elapsed since the initiation of the amplification reaction such that a desired amount of second primer extension product or fragment extension product has been generated. The amount of time can be determined empirically by one skilled in the art.

Suitable dNTP analogs include those commonly used in other sequencing methods and are well known in the art. Examples of dNTP analogs include dideoxyribonucleotides. Examples of rNTP analogs (such as RNA polymerase terminators) include 3'-dNTP. Sasaki et al., Biochemistry (1998) 95:3455-3460. These analogs may be labeled, for example, with fluorochromes or radioisotopes. The labels may also be labels which are suitable for mass spectroscopy. The label may also be a small molecule which is a member of a specific binding pair, and can be detected following binding of the other member of the specific binding pair, such as biotin and streptavidin, respectively, with the last member of the binding pair conjugated to an enzyme that catalyzes the generation of a detectable signal that could be detected by methods such as colorimetry, fluorometry or chemiluminescence. All of the above examples are well known in the art. These are incorporated into the primer extension product or RNA transcripts by the polymerase and serve to stop further extension along a template sequence. The resulting truncated polymerization products are labeled. The accumulated truncated products vary in length, according to the site of incorporation of each of the analogs, which represent the various sequence locations of a complementary nucleotide on the template sequence.

Analysis of the reaction products for elucidation of sequence information can be carried out using any of various methods known in the art. Such methods include gel electrophoresis and detection of the labeled bands using appropriate scanner, sequencing gel electrophoresis and detection of the radiolabeled band directly by phosphorescence, capillary electrophoresis adapted with a detector specific for the labels used in the reaction, and the like. The label can also be a ligand for a binding protein which is used for detection of the label in combination with an enzyme conjugated to the binding protein, such as biotin-labeled chain terminator and streptavidin conjugated to an enzyme. The label is detected by the enzymatic activity of the enzyme, which generates a detectable signal. As with other sequencing methods known in the art, the sequencing reactions for the various nucleotide types (A, C, G, T or U) are carried out either in a single reaction vessel, or in separate reaction vessels (each representing one of the various nucleotide types). The choice of method to be used is dependent on practical considerations readily apparent to one skilled in the art, such as the nucleotide tri phosphate analogs and/or label used. Thus, for example, when each of the analogs is differentially labeled, the sequencing reaction can be carried out in a single vessel. The considerations for choice of reagent and reaction conditions for optimal performance of sequencing analysis according to the methods of the invention are similar to those for other previously described sequencing methods. The reagent and reaction conditions should be as described above for the nucleic acid amplification methods of the invention.

In other embodiments, the methods of the present invention may be useful for sequencing by synthesis methods such as pyrosequencing. In some cases, high throughput pyrosequencing may be carried out by the methods described in Margulies et al. 2005 Nature 437, 376-380. In this method, target nucleic acid such as genomic DNA is fragmented and oligonucleotide linkers are attached. Adapters are ligated to the fragments and the fragments are bound to beads. These immobilized fragments are then amplified. Amplification results in a large number of copies of each immobilized fragment. The amplified immobilized fragments are then sequenced by pyrosequencing as outlined in Ronaghi et al. 1996 Analytical Biochemistry 242, 84-89. Ronaghi describes combining a template, a sequencing primer, dNTPs, an ATP sulfurylase, a DNA polymerase, and a luciferase. Addition of dNTPs to the 3' end of the sequencing primer by the DNA polymerase results in the release of pyrophosphate. Pyrophosphate is used as a substrate by ATP sulfurylase to create ATP. ATP is then used as a substrate by luciferase to generate light which is detected by a sensor. The sequence is then determined by correlating the generation of light by luciferase with the identity of the dNTP added to the reaction. For example, if a dCTP is added to the reaction, and light is generated then the sequenced strand comprises the complement guanosine at that position. The methods of the present invention may also be useful for high throughput sequencing by ligation, sequencing by hybridization and sequencing by synthesis using reversible dyes. Such sequencing methods are well known in the art and have been described in the literature such as for example in *Nature Biotechnology* 26, 1135-1145 (2008).

In some cases, the amplification step may be performed by the methods of the present invention. In other cases, the methods of the present invention are used to immobilize the target nucleic acid onto the beads as depicted in FIG. 4 for example. In some cases, the methods of the present invention may be used to immobilize a sequence specific subset of the target nucleic acid onto beads for high throughput sequencing. Sequence specific immobilization may be particularly useful for reducing the number of different sequences to be examined in a single sequencing run. In some cases, this may be advantageous for increasing the redundancy of the sequences obtained, or increasing the number of overlapping sequences.

Determination of Gene Expression Profile

The amplification methods of the invention can be used for use in determining the levels of expression of multiple genes in a sample since the methods described herein are capable of amplifying multiple target RNAs in the same sample. As described above, amplification products can be detected and quantified by various methods, as described herein and/or known in the art. Since RNA is a product of gene expression, the levels of the various RNA species, such as whole transcriptome or total RNAs, in a sample is indicative of the relative expression levels of the various genes (gene expression profile). Thus, determination of the amount of RNA sequences of interest present in a sample, as determined by quantifying amplification products of the sequences, provides for determination of the gene expression profile of the sample source.

In some embodiments, the methods of the present invention allow for the storage and subsequent analysis of samples, allowing for a sample to be bound to a solid substrate for archiving, then later to be analyzed by the methods described herein to determine a gene expression profile. In some embodiments, the sample can be analyzed multiple times, and stored between analyses.

Accordingly, the invention provides methods of determining gene expression profile in a sample, the method comprising: amplifying single stranded product from at least one RNA sequence of interest in the sample, using any of the methods described herein; and determining amount of amplification products of each RNA sequence of interest, wherein each amount is indicative of the amount of each RNA sequence of interest in the sample, whereby the expression profile in the sample is determined. Generally, labeled products are generated. In one embodiment, the target RNA is mRNA. It is understood that amount of amplification product may be determined using quantitative and/or qualitative methods. Determining amount of amplification product includes determining whether amplification product is present or absent. Thus, an expression profile can includes information about presence or absence of one or more RNA sequence of interest. "Absent" or "absence" of product, and "lack of detection of product" as used herein includes insignificant, or de minimus levels.

The methods of expression profiling are useful in a wide variety of molecular diagnostic, and especially in the study of gene expression in essentially any mammalian cell (including a single cell) or cell population. A cell or cell population (e.g. a tissue) may be from, for example, blood, brain, spleen, bone, heart, vascular, lung, kidney, pituitary, endocrine gland, embryonic cells, tumors, or the like. Expression profiling is also useful for comparing a control (normal) sample to a test sample, including test samples collected at different times, including before, after, and/or during development, a treatment, and the like.

Libraries

In another embodiment, the invention encompasses a library comprising a plurality of nucleic acid molecules. In some cases, each nucleic acid molecule is separately immobilized to a different bead. In another embodiment, the invention encompasses a library comprising a plurality of nucleic acid molecules, wherein each nucleic acid molecule is separately immobilized to a different bead and wherein each bead comprises over 100,000 conal amplification copies of each nucleic acid molecule, wherein the library is contained in a single vessel. As examples, the nucleic acid molecules may be genomic DNA, cDNA, episomal DNA, BAC DNA, or YAC DNA. The genomic DNA may be animal, plant, viral, bacterial, or fungal genomic DNA. Preferably, the genomic DNA is human genomic DNA or human cDNA.

Genetic Analysis

The methods of the present invention may be used in the analysis of genetic information. Amplification methods as disclosed herein may be used in the devices, kits, and methods known to the art for genetic analysis such as but not limited to those found in U.S. Pat. Nos. 6,449,562, 6,287,766, 7,361,468, 7,414,117, 6,225,109, 6,110,709. In some cases, amplification methods of the present invention may be used to amplify target nucleic acid for DNA hybridization studies to determine the presence or absence of polymorphisms. The polymorphisms, or alleles, may be associated with diseases or conditions such as genetic disease. In other cases the polymorphisms may be associated with susceptibility to diseases or conditions, for example polymorphisms associated with addiction, degenerative and age related conditions, cancer, and the like. In other cases, the polymorphisms may be associated with beneficial traits such as increased coronary health, or resistance to diseases such as HIV or malaria, or resistance to degenerative diseases such as osteoporosis, Alzheimer's or dementia.

Kits

One aspect of the invention comprises kits useful for carrying out the methods of the invention.

The kits of the invention can comprise the components described for the methods disclosed herein. The components can be packaged in a manner that allows for efficiently carrying out the methods of the invention.

In one aspect, the kit comprises (a) a first primer comprising a 3'-DNA portion and a 5'-DNA portion, wherein the 3'-DNA portion comprises a random sequence or a specific sequence, and the 5' DNA portion further comprises sequence (A), and (b) a second primer comprising a 5'-RNA portion and a 3' DNA portion, wherein the 3' DNA portion comprises a random sequence or a specific sequence and the 5' RNA portion further comprises sequence (A) or (B). In some embodiments the kit may further comprise (c) an RNA dependent DNA polymerase, (d) a DNA dependent DNA polymerase with strand displacement activity, (e) RNase H, (f) an amplification chimeric primer comprising a 3'-DNA portion and a 5'-RNA portion wherein the sequence of the amplification primer is the substantial the same sequence as the (A) or (B) sequence, or a combination thereof. In some embodiments of this kit the RNA dependent DNA polymerase of component (c) possesses substantial strand displacement activity. In other embodiments, the RNA dependent DNA polymerase of kit component (c) does not possess substantial strand displacement activity. In some cases, component (d) consists of two separate DNA dependent DNA polymerases (d1) and (d2) one of which possesses substantial strand displacement activity and one of which does not possess substantial strand displacement activity. In some cases, the kit does not contain an RNA dependent DNA polymerase.

In some cases, a kit provided by the present invention may comprise an RNA-dependent DNA polymerase and a DNA-dependent DNA polymerase with and without strand displacement activity as described above. In some cases, the kit further comprises single strand specific 3' exonuclease. In some cases, the kit further comprises an RNase that is specific for single or double-stranded RNA and devoid of RNase H activity (i.e. does not substantially degrade the RNA portion in an RNA-DNA heteroduplex).

In one embodiment, the second primer comprises the tail sequence (A), and the amplification primer is substantially the same sequence as sequence (A). These kits are useful for the formation and purification of stem loop structures as described herein. In some embodiments, these kits comprise the enzymes that degrade single stranded DNA and RNA as described herein for clean-up of reaction mixtures comprising the stem loop structures. In some cases, the kit further contains instructions for the use of the kit.

In one aspect, the kit comprises (a) a chimeric oligonucleotide comprising a 3'-DNA portion substantially comprising sequence (A) or (B) and a 5'-RNA sequence (C), and (b) a first primer comprising a 3'-DNA portion and a 5'-DNA portion, wherein the 3'-DNA portion comprises a random or a specific sequence, and the 5' DNA portion comprises sequence (A). In some embodiments, the kit may further comprise a second primer, such as for example an RNA-DNA chimeric second primer, a polymerase having substantial strand displacement activity, RNase H, or a combination thereof.

In one aspect, the kit comprises (a) a chimeric oligonucleotide comprising a 3'-DNA portion substantially comprising sequence (A) or (B) and a 5'-RNA sequence (C), (b) a first primer comprising a 3'-DNA portion and a 5'-DNA portion, wherein the 3'-DNA portion comprises a random or a specific sequence, the 5' DNA portion comprises sequence (A), and the 5' DNA portion further comprises a ligand, and (c) a second primer comprising a 5'-RNA portion and a 3' DNA portion, wherein the 3' DNA portion comprises a random sequence or a specific sequence and the 5' RNA portion further comprises sequence (A) or (B). In some embodiments, the kit may further comprise (e) an RNA dependent DNA polymerase, (d) a DNA dependent DNA polymerase with strand displacement activity, (f) RNase H, (g) a chimeric amplification primer comprising a 3'-DNA portion and a 5'-RNA portion, wherein the chimeric amplification primer comprises a sequence which is substantially the same as sequence (C), or a combination thereof. In some embodiments of this kit the RNA dependent DNA polymerase of component (c) possesses substantial strand displacement activity. In other embodiments, the RNA dependent DNA polymerase of kit component (c) does not possess substantial strand displacement activity. In some cases, component (d) consists of two separate DNA dependent DNA polymerases (d1) and (d2) one of which possesses substantial strand displacement activity and one of which does not possess substantial strand displacement activity. In some cases, the kit does not contain an RNA dependent DNA polymerase. In some cases, the kit further contains instructions for the use of the kit.

In some embodiments the kit further comprises solid surface with an oligonucleotide attached to the surface by the 5'-end comprising a sequence (A) or (B) and further comprising a random or specific annealing sequence (P). In another embodiment the oligonucleotide attached to the solid surface comprises a sequence hybridizable to sequence (A) and the oligonucleotide is attached by the 5'-end.

In one aspect, the kit comprises (a) a first primer comprising a 3'-DNA portion and a 5'-DNA portion, wherein the 3'-DNA portion comprises a random sequence or a specific sequence, and the 5' DNA portion further comprises sequence (A), (b) a second primer comprising a 5'-RNA portion and a 3' DNA portion, wherein the 3' DNA portion comprises a random sequence or a specific sequence and the 5' RNA portion further comprises sequence (A) or (B), (c) a DNA dependent DNA polymerase, (d) a DNA dependent DNA polymerase with strand displacement activity, (e) RNase H, and (f) an amplification chimeric primer comprising a 3'-DNA portion and a 5'-RNA portion wherein the sequence of the amplification primer is substantially the same sequence as the (A) or (B) sequence. In some cases, the kit further contains instructions for the use of the kit.

In some cases, a kit provided by the present invention may comprise (a) a first primer comprising a 3'-DNA portion and a 5'-DNA portion, wherein the 3'-DNA portion comprises a random sequence or a specific sequence, and the 5'-DNA portion further comprises sequence (A) or (B). In some cases, the kit further comprises a ligand attached to the 5'-end of the first primer. The kit may further include (b) a tailed DNA-RNA chimeric second primer as described previously. In some cases, the kit may further include (c) a DNA or RNA dependent DNA polymerase, as described previously. In some cases, the kit may further include (d) a DNA dependent DNA polymerase with strand displacement activity. In some cases, the kit may further include (e) RNase H, and (f) an amplification chimeric primer comprising a 3'-DNA portion and a 5'-RNA portion wherein the sequence of the amplification primer is substantially the same as the (A) or (B) sequence.

In some embodiments, the kits useful for carrying out the methods of the invention may comprise (a) non-tailed DNA first primers comprising a specific or random annealing sequence, (b) tailed DNA-RNA chimeric second primers with specific or random annealing sequence and a tail sequence (A) or (B), (c) a DNA or RNA dependent DNA polymerase, (d) a DNA dependent DNA polymerase with strand displacement activity, (e) RNase H, and (f) an amplification chimeric primer comprising a 3' DNA portion and a 5' RNA portion wherein the sequence of the amplification primer is substantially the same sequence as the (A) or (B) sequence.

In some embodiments the kits useful for carrying out the methods of the invention may further comprise an inhibitor of the DNA dependent DNA polymerase, such as Actinomycin. In some embodiments the kits useful for carrying out the methods of the invention may further comprise a single stranded DNA specific 3' exonuclease such as exonuclease 1, and or a single or double stranded RNA specific RNase such as RNase 1.

In one aspect, the kit comprises (a) reagents for forming an emulsion and (b) a DNA polymerase with substantial strand displacement activity. Reagents for forming a suitable water in oil emulsion are known and commercially available for example in emPCR kits II and III (454/Roche LifeSciences). Said emulsion forming reagents may include for example decamethylcyclopentasiloxane, polyphenylmethylsiloxane, water and/or buffer. In some cases, the kit may further comprise (c) one or more RNA-DNA chimeric primers, (d) an all DNA primer, (e) a solid surface such as a bead or set of beads, a substantially planar array, a well or wells in a plate, or an isolated surface or set of isolated surfaces, (f) RNase H, (g) a chimeric oligonucleotide, or a combination thereof. In some cases, the kit may further comprise instructions for the use of said kit.

The components of the kits may comprise the same aspects and embodiments as described above for the components in the description of methods. For example, the ligands and receptors, the primers, the enzymes and the oligonucleotides can be those described herein to carry out the methods of the invention.

The kits and methods herein can be used for preparing DNA and/or RNA samples for massively parallel sequencing, e.g., of whole genomes or parts of genomes as well as RNA expression analysis for whole transcriptome or parts of a transcriptome. Such kits and methods can be used to diagnosis, prognosis and/or theranostics of conditions including but not limited to cancer, inflammation, fetal abnormality, cardiovascular conditions, etc.

EXAMPLES

Example 1

Target Specific Amplification of Multiple Genomic Sequences on E. coli Genomic DNA All-DNA Tailed First Primer All DNA tailed first primers comprising 3'-end sequence complementary to defined E. coli genomic DNA sequence, and a tailed 5'-end which is not hybridizable to E. coli DNA, and is common to all tailed first primers are used in this example. Four different first all DNA tailed primers are used for this example, as listed in Table 1. The tail sequence of the first primer is the same sequence as that used for the 5'-end tail of the second chimeric primer. The second chimeric DNA-RNA primer comprises a 3'-end random DNA sequence which is hybridizable at random sites on the target DNA, and a 5'-RNA tail which is not hybridizable to the target DNA and is the same sequence as the 5'-tail of the all DNA first primer. Target specific amplification is carried out using the following protocol:

1. First Primer Extension Reaction Mixture:
 1 µl of 1 ng E. coli genomic DNA
 1 µl of 1 µM all DNA first primer
 1 µl of 10× standard Taq polymerase buffer (NEB)
 0.2 µl 10 mM dNTPs (each)
 0.2 µl Taq DNA polymerase (NEB, 5 Units/µl)
 Water to a total of 10 µl The reaction mixtures are incubated under the following temperature and durations in a thermocycler (MJ): 94° C. for 2 min, 50° C. for 30 sec, 72° C. for 5 min, and cooled down to 4° C.

2. Second Chimeric Primer Annealing and Extension:
 2 µl of second tailed chimeric primer (50 µM stock-solution) is added to the first reaction mixtures and the mixtures are incubated in a thermocycler and heated to 98° C. for 3 min (Denaturation) and cooled to 4° C.
 8 µl of the following master mixture (T4 polymerase reaction mixtures) is added to each reaction mixture (above):
 2 µl 10×NEB Buffer 2
 0.1 µl dNTPs
 0.2 µl 100×BSA (NEB)
 0.2 µl T4 DNA polymerase (NEB, 3U/µl)
 5.5 µl water The reaction mixtures are incubated in a thermocycler at the following temperatures and durations: 25° C. for 5 min, 37° C. for 30 min, 95° C. for 5 min (inactivation of T4 DNA polymerase) and slowly cooled down to 4° C.

3. Digestion with Exo 1:
0.5 µl of Exo 1 (NEB, 20 U/µl) are added to each reaction mixture followed by incubation in a thermocycler at the following temperature and durations:
25° C. for 10 min, 37° C. for 30 min, 80° C. for 5 min (inactivation of Exo 1) and cooled down to 4° C.

4. Purification of the Reaction Products Using Agencourt Magnetic Beads

Reaction products are purified using an Agencourt® AMPure® kit according to the manufacturer's protocol.

5. SPIA Amplification

Figure 20:
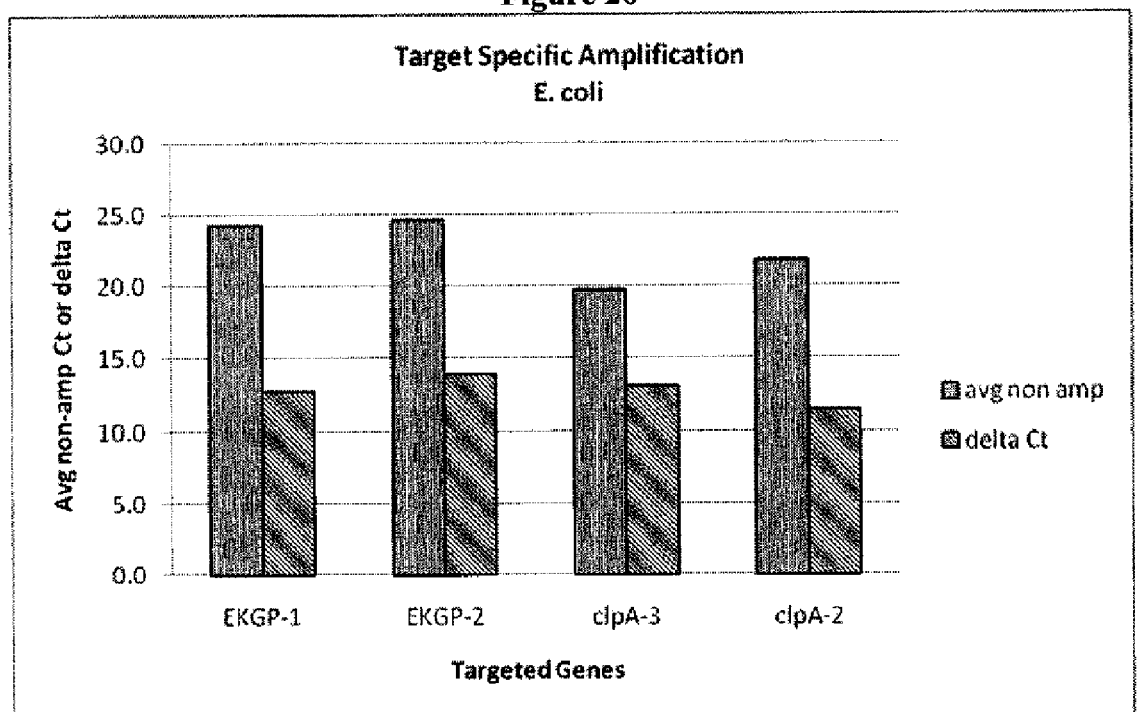
FIG. 20 illustrates normalized results of SPIA-based target specific amplification of DNA using a tailed all-DNA target specific first primer.

SPIA amplification is carried out using buffer and enzyme mixtures from NuGEN's WT-Ovation Pico RNA amplification system (NuGen Technologies Inc, San Carlos Calif., http://www.nugeninc.com/nugen/index.cfm/products/amplification-systems/wt-ovation-pico/):

The amplification amplitude of the targeted genes in the various reactions is indicated by delta Ct. The quantification of each of the non-targeted genes is calculated by the Avg Ct of the specific qPCR reaction of the reactions which do not target the specific gene. Delta Ct is the difference of the avg. Ct of the gene in the non targeted reactions and the Avg Ct for the specified gene in the targeted amplification reactions. Non-amplified Ct values and the delta Ct of the targeted genes are shown in FIG. 20. The delta Ct values for the four *E. coli* genes is very similar, 11.5 to 14 cycles corresponding to 2823-15654 fold amplification.

TABLE 1

Non-amplified Ct values and the delta Ct of the targeted genes are shown in FIG. 20.

| Target gene | Tailed, all DNA first primer sequence | PCR primer | PCR primer sequence |
|---|---|---|---|
| *E. coli* K12 dnaJ gene encoding a heat shock protein M12565 | *GGTAATACGACTCACTATAGGCAGA*CACTGT CAGGGCCGCGGTACG* (SEQ ID NO: 1) | EKGPF1<br><br>EKGPR1 | GGGATTTTAACGGACAGC (SEQ ID NO: 5)<br>CTGATCAAAGATCCGTGC (SEQ ID NO: 6) |
| *E. coli* K12 dnaJ gene encoding a heat shock protein M12565 | *GGTAATACGACTCACTATAGGCAGA*CGTACC GCGGCCCTGACAGTG* (SEQ ID NO: 2) | EKGPF2<br><br>EKGPR2 | TGGTTTTGCACCGCTAC (SEQ ID NO: 7)<br>GCTGTACGTGGCGTGAC (SEQ ID NO: 8) |
| *E. coli* ATP-dependent Clp protease (clpA) gene M31045 | *GGTAATACGACTCACTATAGGCAGA*GGCGACGG CAGAGAACCTGAATAGC* (SEQ ID NO: 3) | clpA-F1<br><br>clpA-R1 | CTGCTGTTTGGTTCGCTGGT (SEQ ID NO: 9)<br>GCTGCTTCCGCCTTGTGCT (SEQ ID NO: 10) |
| *E. coli* ATP-dependent Clp protease (clpA) gene M31045 | *GGTAATACGACTCACTATAGGCAGA*GCTATTCA GGTTCTCTGCCGTCGCC* (SEQ ID NO: 4) | clpA-F2<br><br>clpA-R2 | CTCGATGTGGTGAACTTTATCT (SEQ ID NO: 11)<br>CTTGTTCTTCGCTGTTTGGCT (SEQ ID NO: 12) |

The delta Ct values for the four *E. coli* genes is very similar, 11.5 to 14 cycles corresponding to 2823-15654 fold amplification.
*the 5'-tailed sequence is denoted by the underlined italic letters.

3 μl chimeric amplification primer (50 μM stock; see sequence information below)

17 μl water

40 μl amplification buffer (WT-Ovation Pico System)

20 μl Amplification Enzyme Mix (WT-Ovation Pico System)

The reactions are incubated in a thermocycler at 50° C. for 60 min, followed by 95° C. for 5 min, and cooled down.

Results:

Quantification of amplification products is carried out by Real Time qPCR with SYBR Green, using MJ Opticon. Amplification reactions are diluted 1:100 in Tris-EDTA and 2 μl of the diluted DNA are analyzed by Real Time qPCR, with the corresponding forward and reverse PCR primer pairs as detailed in Table 1.

Figure 19:
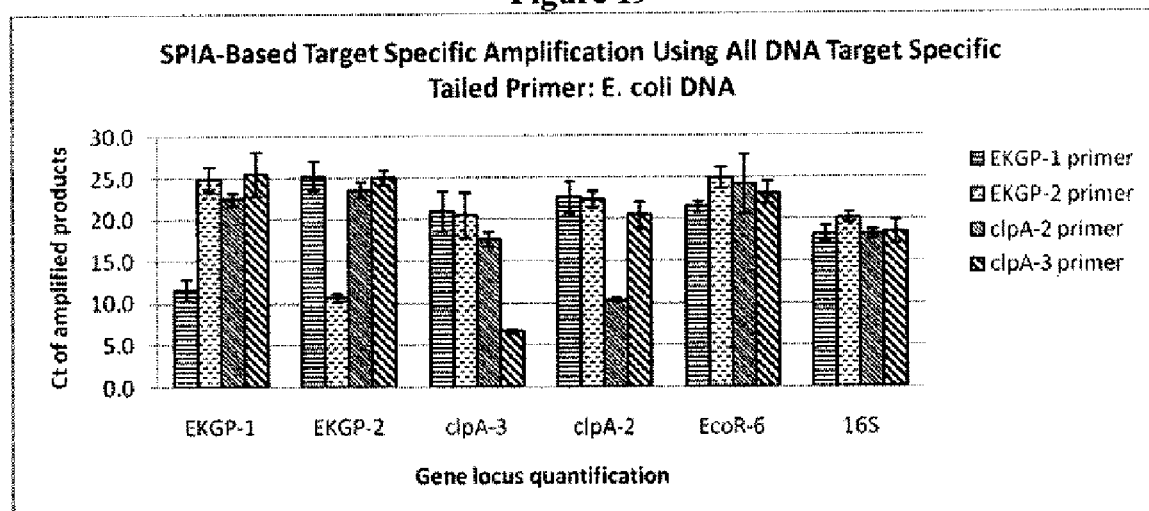
FIG. 19 illustrates the results of SPIA-based target specific amplification of DNA using a tailed all-DNA target specific first primer.

Quantification of the various *E. coli* genes is given as Ct value (inversely related to concentration of the interrogated sequence). The results as summarized in FIG. 19 demonstrate specific amplification of the sequence targeted by the first all DNA tailed primer, with minimal amplification of other genes. The Ct value for the other genes, not targeted for amplification, reflects the input genomic DNA (input into the amplification reaction according to the method of the invention).

TABLE 2

Chimeric Primers

| Chimeric Primer | Chimeric Primer Sequence |
|---|---|
| Second tailed chimeric primer | gguaauacgacucacuauaggcagaNNNNNN* (SEQ ID NO: 13) |
| Chimeric amplification primer | gguaauacgacucacuauAGGCAGA* (SEQ ID NO: 14) |

*Lower case letters denotes ribonucleotides; Upper case letters denote deoxynucleotides Example 2

Single and Multiplex Sequence Specific Amplification

All DNA sequence specific tailed first primer

Single and multiplexed target specific amplification utilizing the methods of the invention is demonstrated in this example. Four specific gene sequences on genomic yeast DNA are targeted.

Target specific tailed all DNA first primers used for this example as well as the qPCR primer pairs utilized for quantification of the amplification products are described in Table 3. The input for all amplification reactions is 1 ng genomic yeast DNA. Two experiments employing different enzymes and buffer system in the first and second primer extension reactions, prior to the linear isothermal amplification steps are described below.

I. The first set of reactions described herein, for single and multiplexed amplification of specific genomic sequences, are carried out as follows:
  a. Genomic yeast DNA, 1 ng/µl (1 µl) is mixed with 1 µl of 10× Standard Taq buffer (NEB), 0.2 µl dNTPs (10 mM each), 0.2 µl Taq DNA polymerase (NEB) 1 µl of the specified tailed target specific first primer (one each or a combination of primers), and 6.6 µl water, on ice. The reaction mixtures are incubated in a thermocycler at the following temperatures and durations: 94° C. for 2 min., 50° C. for 1 min., 72° C. for 5 min., and cooled down to 4° C.
  b. 2 µl of a 50 µM stock solution of a chimeric second primer (the same sequence as that used in the E. coli example above), is added to each reaction mixture and the reactions are subjected to heat Denaturation (98° C. for 3' min.) and cooled to 4° C.
  c. Second primer extension is carried out using T4 DNA polymerase (NEB) following the addition of the following reagents: 2 µl of 10×NEB buffer 2 (T4 polymerase buffer), 0.1 µl 10 mM dNTPs (each), 0.2 µl 100×BSA (NEB), 0.2 µl T4 DNA polymerase (NEB) and 5.5 µl water. The reactions are incubated in a thermocycler at the following temperatures and durations: 25° C. for 5 min., 37° C. for 30 min., 98° C. for 3 min., and slowly cooled to 4° C.
  d. The products of the second primer extension reactions are than digested utilizing exonuclease 1 (0.5 µl for each reaction) and RNase I (0.5 µl for each reaction). The digestion reactions are carried out at 37° C. for 30 min. in a thermocycler, followed by inactivation of the enzymes (80° C. for 20 min.).
  e. The reaction products are purified using Agencourt magnetic beads as per the manufacturer's instructions.
  f. Isothermal linear amplification (SPIA) is carried out in a reaction mixture containing the above purified reaction products (10 µl), 2 µl chimeric amplification primer (100M stock solution; as in the E. coli example), 18µ water, 40 µl Amplification Buffer and 20 µl Amplification Enzyme Mixture (from NuGEN Technologies Inc., as used in the WT-Ovation Pico RNA Amplification System). Amplification reactions are carried out as described in Example 1.

Figure 21:
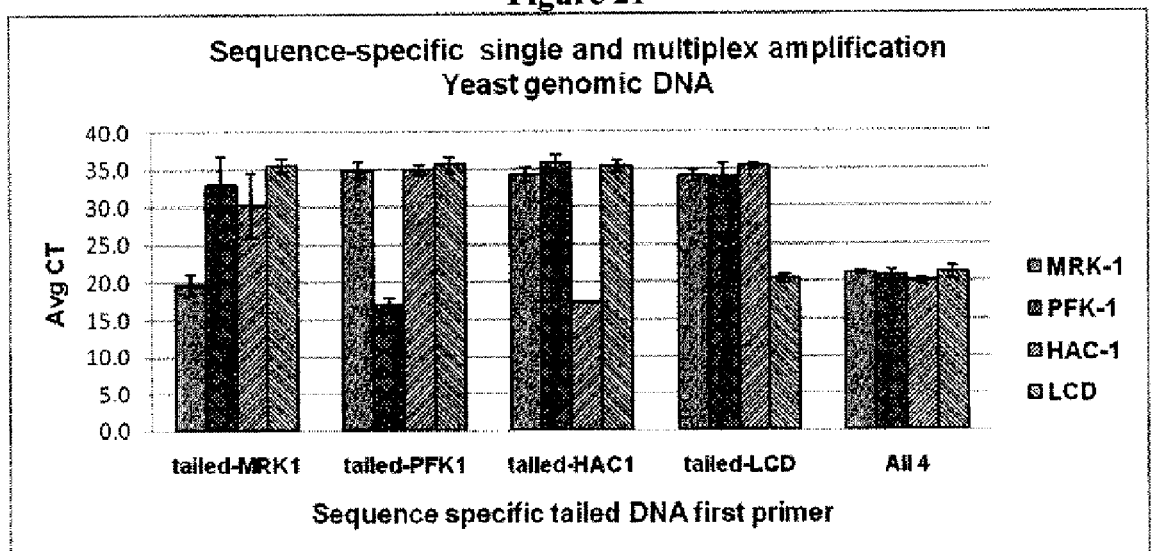
FIG. 21 illustrates results of sequence-specific single and multiplex amplification of genes from yeast genomic DNA using a tailed all-DNA target specific first primer.

Results:

Quantification of the four targeted genes, targeted or not in the amplification reactions analyzed, is carried out by real-time PCR as described in Example 1, using the PCR primer pairs specific for the targets of interest (Table 3). Average Ct values (all reactions are carried out in triplicates or duplicates) are inversely related to the concentration of the target of interest in the reactions. FIG. 21 depicts the results of Real-Time PCR quantification of the amplification products described above. The Avg Ct values for the different targets in the various reactions are grouped according to the type of tailed all DNA target specific first primer (or primers) employed. As is shown in FIG. 20, amplification of the targeted gene of interest without amplification of the non targeted genes, is achieved in reactions carried out employing a tailed all DNA first primer specific for the target of interest. Thus, for example, reactions carried out employing the tailed all DNA first primer specific for a sequence of the MRK1 gene result in amplification of the MRK1 gene but does not lead to amplification of the non targeted genes PFK1, HAC1 and LCD. The amplification reactions carried out with single tailed all DNA first primer thus results in amplification of the single sequence of interest, as shown by the first four reactions, marked on the X axis of FIG. 20 as Tailed-MRK1, Tailed-PFK1, Tailed-HAC1 and Tailed-LCD (demoting the specific tailed all DNA first primer employed in the amplification reaction according to the current invention).

The method of the invention also provide for simple and efficient multiplexed amplification of sequences of interest. As shown in FIG. 21, efficient and equal amplification of four yeast genes in a sample comprising yeast genomic DNA, is achieved in reactions employing the four specific tailed all DNA primer (marked as "all 4"). The Avg Ct values for all four genes are similar and lower than that obtained for reactions carried out without the specific tailed all DNA first primer.

II. Single and multiplexed amplification of specific targeted yeast genomic sequences using the method of the invention: Amplification reactions are carried out similarly to the reactions described in I., with the exception that Taq DNA polymerase is employed for first and second primer extension steps and the buffer used in both reactions steps is ThermoPol (NEB). The second primer extension step is carried out by incubation of the reactions mixtures in a thermocycler at the following temperatures and durations: 50° C. for 5 min., 55° C. for 1 min., 72° C. for 5 min., 98° C. for 3' and cooled slowly to 40° C.

Single sequence specific amplification is carried out using the tailed all DNA first primer specific for the amplification of MRK1 gene sequence, Tailed-MARK1 (Table 3) and multiplexed amplification reactions are carried out using all four tailed all DNA target specific first primers: Tailed-MRK1, Tailed-PFK1, Tailed-HAC1 and Tailed-LCD (Table 3).

Figure 22:
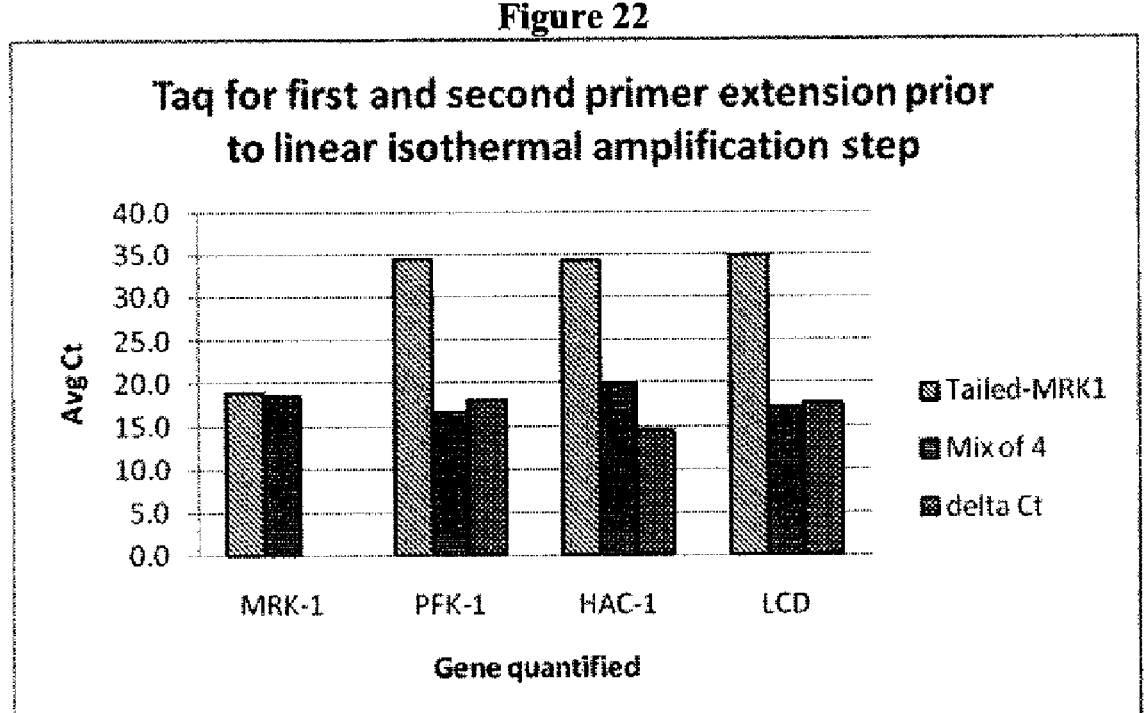
FIG. 22 illustrates results the results of using the Taq polymerase enzyme for extension of the tailed all-DNA sequence specific first primer and an RNA-DNA chimeric second primer.

Results: Single or multiplexed amplification of the sequences of interest is determined by quantification of the targeted sequence by Real-Time PCR as described above. Avg Ct values for the various targeted and non targeted gene sequences (non-targeted in the case of amplification of a single targeted sequence, MRK1) are shown in FIG. 22. Efficient and specific single and multiplexed amplification is achieved using Taq DNA polymerase, without strand displacement, for both primer extension products according to the method of the invention.

TABLE 3

| Seq name | Definition | Tailed first primer sequence *(5' to 3') | Q-PCR primers | Q-PCR primer sequences (5' to 3') |
| --- | --- | --- | --- | --- |
| MRK1 | Saccharomyces cerevisiae putative protein kinase (MRK1) gene (U22348) | GGTAATACGACTCACTATAGGC AGAaatgcttgaaaccggatcag (SEQ ID NO: 15) | Forward MRK-F<br>Reverse MRK-R | ctcccgaactcatgtttggt (SEQ ID NO: 19)<br>cccaaaagcaactcagcaat (SEQ ID NO: 20) |

TABLE 3-continued

| Seq name | Definition | Tailed first primer sequence *(5' to 3') | Q-PCR primers | | Q-PCR primer sequences (5' to 3') |
|---|---|---|---|---|---|
| PFK1 | *Saccharomyces cerevisiae* phosphofructokinase, alpha subunit (PFK1) gene (M26943) | GGTAATACGACTCACTATAGGC AGAccggtttaatcactggtgct (SEQ ID NO: 16) | Forward | PFK-F | aacttccgtcacgacaaagg (SEQ ID NO: 21) |
| | | | Reverse | PFK-R | tgatgtcagccaacaattgag (SEQ ID NO: 22) |
| HAC1 | *Saccharomyces cerevisiae* HAC1 gene for basic leucine zipper protein Hac1 (D26506) | GGTAATACGACTCACTATAGGC AGAaactggctgaccacgaagac (SEQ ID NO: 17) | Forward | HAC-F | tcgcactcgtcgtctgatac (SEQ ID NO: 23) |
| | | | Reverse | HAC-R | acaaagtcgaggctccattg (SEQ ID NO: 24) |
| LCD | Synthetic construct *Saccharomyces cerevisiae* clone FLH202554.01X LCD1 gene (DQ332471) | GGTAATACGACTCACTATAGGC AGAtcaagcaggtagaaagccaa (SEQ ID NO: 18) | Forward | LCD-F | tatgccaaaccgaaactgtg (SEQ ID NO: 25) |
| | | | Reverse | LCD-R | caaggtgtcgatgatctctca (SEQ ID NO: 26) |

* Capital underlined letter denote the 5; -end tail (all DNA tailed primer)

Example 3

Sequence Specific Multiplex Amplification of RNA Transcripts

All DNA Tailed First Primer

A subject presents to a health care provider symptoms indicative of lung cancer, including coughing up blood and shortness of breath. A chest X-ray is performed on the subject and a suspicious mass is detected in the lungs of the subject. A needle biopsy is performed on the subject to obtain tissue from the suspicious mass for further analysis. The biopsied tissue recovered from the subject is processed to extract and purify total RNA using a commercially available Qiagen RNeasy kit according to the manufacturer's instructions.

500 pg of total RNA representing at least a portion of the transcriptome of the biopsied material is amplified by the methods of the present invention as described herein using: 10 pmol of all-DNA first primers comprising a 5' segment and a 3' segment. The 3' DNA segment of these first primers further comprise an annealing sequence that is complementary to the sequence(s) of interest. In this example, three different first primers with annealing sequences specific for abl, ras, and her2 transcripts are included in a single primer extension reaction. The 5' DNA segment of the first primers comprise a tag sequence (A). Reaction mixture and reaction conditions can be those described by the protocols for the WT-Ovation Pico RNA Amplification system, the details of which are available on NuGEN's website: http://www.nugen-inc.com/tasks/sites/nugenassets/File/quickprotocols/qp_wt_ov_pico.pdf and http://www.nugeninc.com/tasks/sites/nugen/assets/File/user_guides/userguide_wt_ov_pico.pdf The reaction mixture can be heated to 75° C. for 2 minutes and cooled. 1 µl of an RNA-dependent DNA polymerase (i.e. AMV reverse transcriptase) is introduced into the reaction mixture to create a first primer extension product hybridized to the RNA by incubating the reaction mixture at 37° C. for 1 hour. The RNA is then removed from the first primer extension product by cooling the reaction mixture to 37° C., adding 2 units of RNase H and RNase I to the reaction mixture and incubating for 20 minutes at 37° C. The reaction mixture is then heated to 90° C. for 3 minutes to inactivate the enzymes. The first primer extension product can be mixed with 10 ul of the second primer extension mixture. The second strand polymerase can be one that does not have strand displacement, such as for example T4 DNA polymerase. Conditions as described in Examples 1 and 2 above may be applicable. 20 pmol of a second primer comprising a 5' segment and a 3' segment, a portion of the 5' segment comprising RNA, and a portion of the 3' segment comprising DNA. A portion of the 5' RNA segment comprises a tag sequence (B), and a portion of the 3' DNA segment comprises an annealing sequence comprising a random sequence.

The reaction mixture can be incubated for 30 minutes at 37° C., followed by addition of exonuclease 1 (0.5 µl at 37° C. for 30 min.), and finally heating to 75° C. for 5 minutes to stop the reaction by inactivating the enzymes. The products are purified and subjected to SPIA amplification. The first and second primer extension products are purified using Agencourt magnetic beads as per the manufacturer's instructions.

The first primer extension product in the partial duplex is extended by the DNA polymerase in the amplification reaction mixture comprising an DNA dependent DNA polymerase and a DNA dependent DNA polymerase, and the resulting primer extension products comprise a double stranded DNA product with a DNA/RNA heteroduplex at one end of a sequence (B')/(B). The first and second primer extension products are then purified using Agencourt magnetic beads as per the manufacturer's instructions.

Isothermal linear amplification (SPIA) is carried out in a reaction mixture containing the above purified reaction products (10 µl), 2 µl chimeric amplification primer (100 µM stock solution), 18 µl water, 40 µl amplification buffer and 20 µl amplification enzyme mixture as provided in the WT-Ovation Pico RNA Amplification System (NuGen Technologies). The amplification is carried out according to the instructions provided for the WT-Ovation Pico RNA Amplification System.

The amplified product is then analyzed and quantitated by Real Time qPCR with SYBR Green, using an MJ Opticon thermocycler. Amplification reactions are diluted 1:100 in Tris-EDTA and 2 µl of the diluted DNA are analyzed using primer pairs specific for abl, ras, and her2 in three separate reactions.

The results of the qPCR are analyzed to determine that abl is overexpressed in the cells of the suspicious mass. The results are combined with immunohistochemical and cytological analysis to determine a suggested course of therapy.

Example 4

Sequence Specific Amplification of Mammalian Genomic DNA

All DNA Tailed First Primer

An individual is tested by a personal genomics business using the methods of the present invention for single nucleotide polymorphisms (SNPs) within the BRCA1, BRCA2, p53, MPO, NAT1, NAT2, and ras coding regions that are related to increased risks for specific types of cancer.

The individual supplies a small sample of tissue (i.e. a cheek swab) to the personal genomics business. Genomic DNA from the sample of tissue is isolated using a commercially available kit (i.e. Promega's Wizard R Genomic DNA Purification Kit), according to the manufacturer's protocol.

1 ng of purified genomic DNA is used to specifically amplify the sequences corresponding to the genomic regions with known, cancer related, SNPs of the BRCA1, BRCA2, p53, MPO, NAT 1, NAT2, and ras genes from the complex mixture of sequences present in the genomic DNA in separate reactions. Double stranded DNAs, each comprising a sequence of interest, an (A)/(A') duplex at one end, and a DNA-RNA heteroduplex of sequence (B')/(B) at the other end are created using the steps outlined in FIGS. 1 and 2.

The double stranded DNAs each comprising a sequence of interest are amplified by isothermal linear amplification using the methods of the present invention to generate single stranded amplified product comprising the complement of the sequences of interest and a sequence (A') at the 3' end. The amplified product is then sequenced by dye terminator sequencing using a primer complementary to the sequence (A').

The resulting sequences are used to determine the presence or absence of SNPs related to cancer in the genes of interest. A report is generated that includes the SNPs identified, the impact of the SNPs on lifetime risk of developing specific diseases or conditions, and suggestions for prophylactic or therapeutic interventions.

Example 5

Sequence Specific Multiplex Amplification of Fetal Mammalian Genomic DNA

All DNA Tailed First Primer

A fetal sample is obtained by amniocentesis. DNA is extracted and purified from the sample using a commercially available kit (i.e. Promega's Wizard R Genomic DNA Purification Kit). 1 ng of the DNA is amplified in a multiplex fashion according to the method outlined in FIGS. 1 and 2. Twenty three sequence specific all DNA first primers are used, each complementary to a region of one the following genes:

ACADM which is present on chromosome 1;
ABCA12 which is present on chromosome 2;
ALAS1 which is present on chromosome 3;
ANK2 which is present on chromosome 4;
ADAMTS2 which is present on chromosome 5;
BCKDHB which is present on chromosome 6;
ASL which is present on chromosome 7;
FGFR1 which is present on chromosome 8;
ABO which is present on chromosome 9;
CDH23 which is present on chromosome 10;
ACAT1 which is present on chromosome 11;
ACVRL1 which is present on chromosome 12;
ATP7B which is present on chromosome 13;
COCH which is present on chromosome 14;
CAPN3 which is present on chromosome 15;
ABCC6 which is present on chromosome 16;
ACADVL which is present on chromosome 17;
FECH which is present on chromosome 18;
APOE which is present on chromosome 19;
ADA1 which is present on chromosome 20;
APP which is present on chromosome 21;
IGL which is present on chromosome 22;
pyruvate dehydrogenase E1 alpha which is present on chromosome X; and
SRY which is present on chromosome Y;

The amplified products are then analyzed and quantitated by Real Time qPCR with SYBR Green, using an MJ Opticon thermocycler. Amplification reactions are diluted 1:100 in Tris-EDTA and 2 µl of the diluted DNA are analyzed using primer pairs specific for the twenty three different genes in twenty-three separate reactions.

The results of the qPCR are analyzed to determine whether the fetus exhibits an aneuploid genotype.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

---

What is claimed is:

1. A method for creating a partial RNA-DNA heteroduplex comprising:
    a) providing a template nucleic acid in a reaction mixture;
    b) adding a first primer to said reaction mixture and generating a first primer extension product with said first primer;
    c) adding a second primer that is an RNA-DNA chimeric primer to said reaction mixture;
    d) adding a DNA polymerase to said reaction mixture, wherein said DNA polymerase comprises RNA-dependent polymerase activity; and
    e) degrading a portion of said first primer extension product that is not hybridized to a second primer extension product in a double-stranded first and second primer extension product complex by adding an exonuclease to said reaction mixture;
    whereby said partial RNA-DNA heteroduplex is created.

2. A method for producing amplified nucleic acid comprising:
    a) providing a template nucleic acid;
    b) annealing an all-DNA first primer or set of all-DNA first primers comprising a 3' end whereby a portion of the 3' end comprises a template annealing sequence and a 5' tail sequence whereby a portion of the tail sequence comprises a sequence (A);
    c) extending said first primer or set of first primers with a DNA polymerase to create a first primer extension product or first set of primer extension products;
    d) dissociating the primer extension product or products from the template nucleic acid;
    e) annealing a second primer comprising a 3' DNA sequence and a 5' RNA sequence, whereby a portion of the 3' end comprises a randomized annealing sequence and a portion of the 5' end comprises sequence (A) or a sequence (B), to said primer extension product or products, wherein sequence (B) is different from sequence (A); and
    f) extending said second primer with a DNA polymerase to create a second primer extension product or set of second primer extension products to produce a double stranded DNA product or products comprising an A-A' DNA duplex at one end, wherein (A') is the complement of (A).

3. The method of claim 2 wherein the template nucleic acid is selected from the group consisting of DNA and RNA.

4. The method of claim 2 wherein the template nucleic acid is RNA and the DNA polymerase of step (c) is an RNA dependent DNA polymerase.

5. The method of claim 4 wherein the dissociation step of step (d) is performed by degrading the RNA.

6. The method of claim 2 wherein the template nucleic acid is DNA and the DNA polymerase of step (c) is a DNA dependent DNA polymerase.

7. The method of claim 6 wherein the dissociation step of step (d) is performed by heat or chemical denaturation.

8. The method of claim 2 wherein the DNA polymerase does not exhibit substantial strand displacement activity.

9. The method of claim 2 wherein each template annealing sequence of the set of primers is specific for a target or region of template nucleic acid.

10. The method of claim 2 wherein the template annealing sequence of the first primer comprises a random sequence.

11. The method of claim 2 wherein the members of the set of first primers each comprises a distinct 3' DNA annealing sequence, each specific for a target or region of template nucleic acid.

12. The method of claim 2 wherein the first primer tail sequence is not complementary to the template nucleic acid.

13. The method of claim 2 wherein the 5' tail sequence of the second primer comprises sequence (A).

14. The method of claim 2 wherein the 5' tail sequence of the second primer does not comprise tail sequence (A).

15. The method of claim 2, wherein sequence A or B of said second primer is not hybridized to said first primer extension product, and further comprising step (g), degrading single stranded 3' end of said first primer extension product or products in the complex of first and second primer extension products with a single stranded DNA specific 3' exonuclease.

16. The method of claim 15 further comprising step (h), adding a DNA polymerase with reverse transcriptase activity to create a double stranded nucleic acid with an A-A' DNA duplex at one end and an B-B' DNA-RNA heteroduplex at the other end, wherein sequence B comprises RNA, sequence B' comprises DNA, and B' is the complement of B.

17. The method of claim 16 further comprising SPIA with a reaction mixture comprising RNase H, a composite amplification primer comprising a 3' DNA portion and a 5' end whereby a portion of the 5' end comprises RNA wherein the RNase H cleaves the RNA portion of the heteroduplex of step (h) to produce a single stranded end, and the amplification primer hybridizes to the single stranded end produced by RNase H, and a DNA polymerase with strand displacement activity.

18. The method of claim 2 wherein the first primer or set of primers comprises a ligand portion at the 5'end.

19. The method of claim 16 further comprising:
(i) cleavage of the RNA from the DNA-RNA heteroduplex with RNase H;
(j) annealing a chimeric oligonucleotide comprising a 5' end whereby the 5' end comprises RNA sequence (C) and a 3' end whereby the 3' end comprises the DNA sequence (B) to the double stranded nucleic acid product;
(k) extending the double stranded nucleic acid product with a DNA polymerase to produce a C-C' DNA-RNA heteroduplex, wherein C' is the complement of C; and
(l) amplifying the second primer extension product with a reaction mixture comprising RNase H, an amplification primer comprising a 3' DNA portion and a 5' end whereby a portion of the 5' end comprises RNA that hybridizes to a portion of the single stranded end produced by RNase H, and a DNA polymerase with strand displacement activity to produce an amplification product comprising sequence (B) near its 3' end and sequence (A') at the 5' end.

20. A method for producing amplified nucleic acid comprising:
a) providing a template nucleic acid;
b) annealing an all-DNA first primer or a set of all-DNA first primers comprising a 3' end whereby a portion of the 3' end comprises a template annealing sequence and a 5' end whereby a portion of the 5' end comprises a DNA tail sequence (A) that is complementary to a sequence (A');
c) extending said first primer or set of first primers with a DNA polymerase to create a primer extension product or set of primer extension products;
d) dissociation of the primer extension product or products from the template nucleic acid;
e) annealing a second primer comprising a 3' DNA end, whereby a portion of the 3' end comprises a random template annealing sequence, and a 5' RNA end, whereby a portion of the 5' end comprises an RNA tail sequence (A) that is complementary to the sequence (A'), to said primer extension product or products or to said template nucleic acid;
f) extending said second primer with a DNA polymerase to create a second primer extension product or set of second primer extension products, wherein a portion of the 3' end of said second primer extension product or products comprises sequence (A'), wherein (A') is the complement of (A); and
g) denaturing and annealing the second primer extension product or set of second primer extension products to form a stem loop structure comprising an A-A' RNA-DNA heteroduplex.

21. The method of claim 20 further comprising the addition of a 3' single stranded DNA specific exonuclease and single strand specific RNase to degrade unincorporated primers and template nucleic acid.

22. The method of claim 21 further comprising amplification with a reaction mixture comprising RNase H, an amplification primer comprising sequence (A'), and a DNA polymerase with strand displacement activity, wherein the amplification primer comprises a 3'-DNA sequence and a 5'-RNA sequence.

23. The method of claim 20 wherein said template nucleic acid is selected from the group consisting of RNA and DNA.

24. The method of claim 20 wherein the template nucleic acid is RNA and the DNA polymerase of step (c) is an RNA dependent DNA polymerase.

25. The method of claim 20 wherein the template nucleic acid is DNA and the DNA polymerase of step (c) is a DNA dependent DNA polymerase.

26. The method of claim 24 wherein the dissociation step of step (d) is performed by degradation of the RNA.

27. The method of claim 25 wherein the dissociation step of step (d) is performed by chemical or heat denaturation.

28. The method of claim 20 wherein the DNA polymerase does not exhibit substantial strand displacement activity.

29. The method of claim 20 wherein each DNA annealing sequence in the set of first DNA primers is specific for a target or region of the template nucleic acid.

30. The method of claim 20 wherein a portion of the 5' tail sequence of the first primer is sequence (A) and a portion of the 5' tail sequence of the second primer is sequence (A).

31. The method of claim 20 wherein the tail sequence is not complementary to the template nucleic acid.

32. The method of claim 2 wherein the first primer or set of first primers are immobilized to a solid surface.

33. The method of claim 32 wherein the surface is selected from the group consisting of a bead, a magnetic particle, a microarray, a gene chip, and an array.

34. The method of claim 32 wherein the first primer or set of first primers are attached to the solid surface at the 5' end.

35. The method of claim 2 wherein the second primer or set of second primers comprise a template annealing sequence.

36. The method of claim 33 wherein the first primer or set of first primers further comprise a spacer element between the surface and the 5' end.

37. The method of claim 36 wherein the template annealing sequence of the first primer or set of first primers are each specific to a target or region of the template nucleic acid.

38. The method of claim 36 wherein the method further comprises:
(g) cleaving the spacer element with light or chemical cleavage to release the double stranded nucleic acid from said surface; and
(h) amplifying the released double stranded nucleic acid in solution with a reaction mixture comprising RNase H, an amplification primer comprising a DNA portion and a 5' RNA portion, and a DNA polymerase with strand displacement activity to produce an amplified DNA product or products having a defined 3' sequence comprising sequence (A').

39. The method of claim 2 wherein the first primer or set of first primers are in solution.

40. The method of claim 20 wherein the first primer or set of first primers are immobilized to a solid surface.

* * * * *